(12) United States Patent
Farrell et al.

(10) Patent No.: US 8,649,997 B2
(45) Date of Patent: Feb. 11, 2014

(54) SYSTEMS AND METHODS FOR PREDICTING AMBIENT TEMPERATURE IN A FLUID ANALYTE METER

(75) Inventors: John Farrell, New York, NY (US); Harris Lieber, White Plains, NY (US); Hoi-Cheong Steve Sun, Mount Kisco, NY (US); Mu Wu, Hopewell, NY (US); Jun Chen, Warren, NJ (US); Igor Gofman, Croton-on-Hudson, NY (US); Jeffery S. Reynolds, New Fairfield, CT (US); Xin Wang, Clifton Park, NY (US); Gregory Stefkovic, Mahopac, NY (US); Bern Harrison, Granger, IL (US)

(73) Assignee: Bayer HealthCare LLC, Tarrytown, PA (US)

( * ) Notice: Subject to any disclaimer, the term of this patent is extended or adjusted under 35 U.S.C. 154(b) by 374 days.

(21) Appl. No.: 13/122,098

(22) PCT Filed: Oct. 2, 2009

(86) PCT No.: PCT/US2009/059430
§ 371 (c)(1),
(2), (4) Date: Mar. 31, 2011

(87) PCT Pub. No.: WO2010/040090
PCT Pub. Date: Apr. 8, 2010

(65) Prior Publication Data
US 2011/0191059 A1     Aug. 4, 2011

Related U.S. Application Data

(60) Provisional application No. 61/102,661, filed on Oct. 3, 2008, provisional application No. 61/200,568, filed on Nov. 28, 2008, provisional application No. 61/160,084, filed on Mar. 13, 2009, provisional application No. 61/233,372, filed on Aug. 12, 2009.

(51) Int. Cl.
*G06F 15/00*     (2006.01)

(52) U.S. Cl.
USPC .............. 702/130; 340/636.2; 340/573.1; 340/603

(58) Field of Classification Search
USPC .......... 702/130; 73/61.46, 113.34; 340/636.2, 340/573.1, 603, 636.1, 365; 600/300, 549, 600/365, 347; 128/898
See application file for complete search history.

(56) References Cited

U.S. PATENT DOCUMENTS

| | | |
|---|---|---|
| 4,741,476 A | 5/1988 | Russo et al. |
| 4,836,442 A | 6/1989 | Beckey |

(Continued)

FOREIGN PATENT DOCUMENTS

| | | |
|---|---|---|
| WO | 2005/000114 A2 | 1/2005 |
| WO | 2005/001680 A1 | 1/2005 |
| WO | 2009/119116 A1 | 10/2009 |

OTHER PUBLICATIONS

PCT/US2009/059430 International Search Report; mailed Mar. 5, 2010; 6 pages.

(Continued)

*Primary Examiner* — Carol S Tsai
(74) *Attorney, Agent, or Firm* — Nixon Peabody LLP

(57) ABSTRACT

A system for a meter configured to determine an analyte concentration of a fluid sample includes a housing and a temperature sensor disposed within the housing. The system also includes a processor configured to receive temperature data from the temperature sensor upon the meter entering one of a charge state and a discharge state. The processor is further configured to predict a temperature value that approximates the ambient temperature outside of the housing. The predicted temperature value is based on historical temperature data received from the temperature sensor such that the predicted temperature value remains constant if a recently received temperature value remains within predetermined upper and lower temperature thresholds and the recently received temperature value exceeds the at least one predicted temperature value.

22 Claims, 32 Drawing Sheets

(56) References Cited

U.S. PATENT DOCUMENTS

| | | | |
|---|---|---|---|
| 5,001,656 A | 3/1991 | Zimmerman et al. | |
| 5,199,637 A | 4/1993 | Adams | |
| 5,405,511 A * | 4/1995 | White et al. | 205/777.5 |
| 6,283,628 B1 | 9/2001 | Goodwin | |
| 6,494,090 B1 * | 12/2002 | Lösing et al. | 73/204.26 |
| 6,635,167 B1 | 10/2003 | Richards et al. | |
| 6,645,368 B1 | 11/2003 | Beaty et al. | |
| 6,787,109 B2 | 9/2004 | Haar et al. | |
| 6,821,249 B2 * | 11/2004 | Casscells, III et al. | 600/300 |
| 7,338,639 B2 | 3/2008 | Burke et al. | |
| 7,364,353 B2 | 4/2008 | Kolk | |
| 7,390,667 B2 | 6/2008 | Burke et al. | |
| 7,407,811 B2 | 8/2008 | Burke et al. | |
| 8,133,178 B2 * | 3/2012 | Brauker et al. | 600/365 |
| 8,164,468 B2 * | 4/2012 | Gofman et al. | 340/636.2 |
| 8,441,463 B2 * | 5/2013 | Harrison | 345/174 |
| 2002/0170823 A1 * | 11/2002 | Housefield et al. | 204/403.01 |
| 2003/0092975 A1 * | 5/2003 | Casscells, III et al. | 600/300 |
| 2004/0157338 A1 | 8/2004 | Burke et al. | |
| 2004/0256248 A1 | 12/2004 | Burke et al. | |
| 2004/0259180 A1 | 12/2004 | Burke et al. | |
| 2004/0260511 A1 | 12/2004 | Burke et al. | |
| 2006/0229502 A1 * | 10/2006 | Pollock et al. | 600/300 |
| 2007/0032706 A1 * | 2/2007 | Kamath et al. | 600/300 |
| 2007/0264721 A1 | 11/2007 | Buck | |
| 2008/0098802 A1 | 5/2008 | Burke et al. | |
| 2008/0300919 A1 | 12/2008 | Charlton et al. | |
| 2008/0301158 A1 | 12/2008 | Brown et al. | |
| 2009/0023222 A1 | 1/2009 | Wu et al. | |
| 2009/0146826 A1 * | 6/2009 | Gofman et al. | 340/636.2 |
| 2010/0160761 A1 * | 6/2010 | Say et al. | 600/365 |
| 2010/0268475 A1 | 10/2010 | Kusumoto | |
| 2012/0172691 A1 * | 7/2012 | Brauker et al. | 600/347 |

OTHER PUBLICATIONS

PCT/US2009/059430 Written Opinion; mailed Mar. 5, 2010; 12 pages.

* cited by examiner

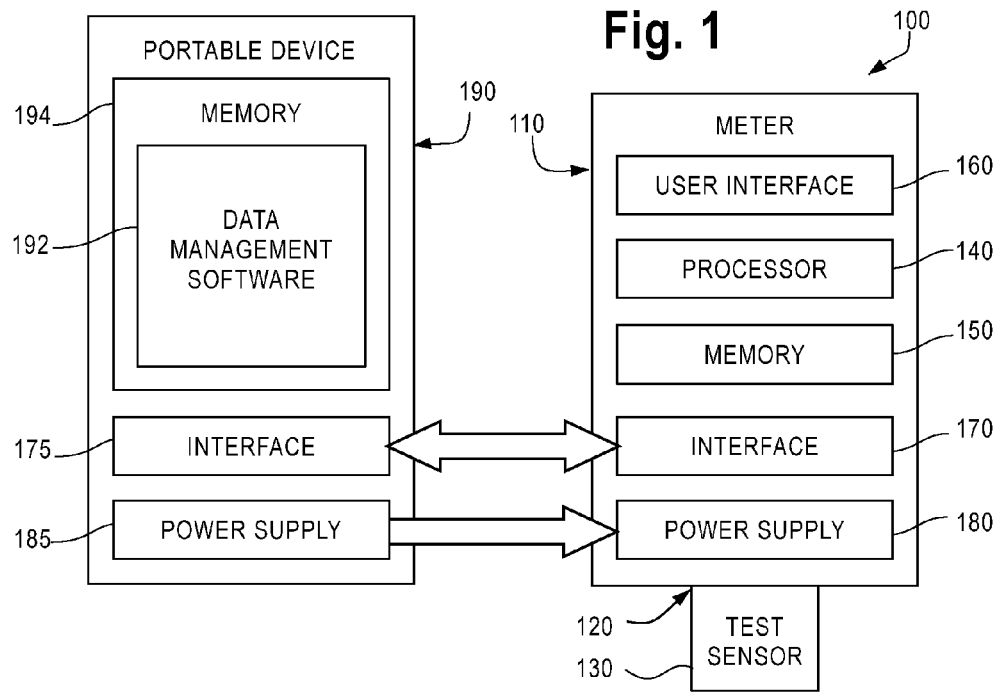
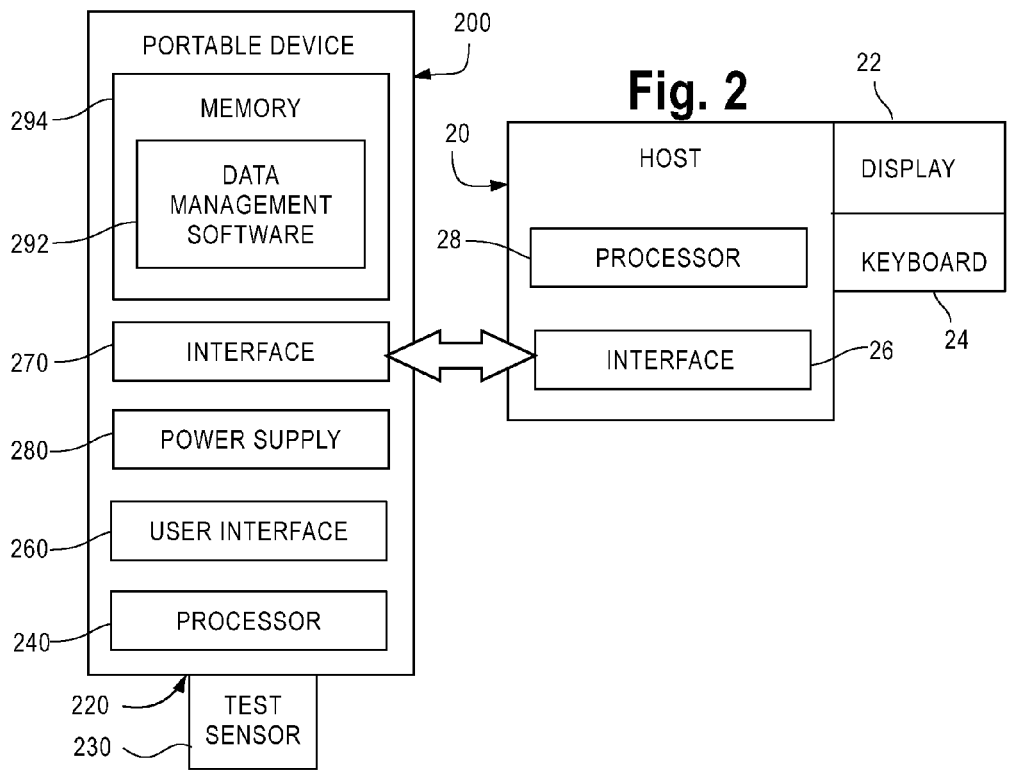

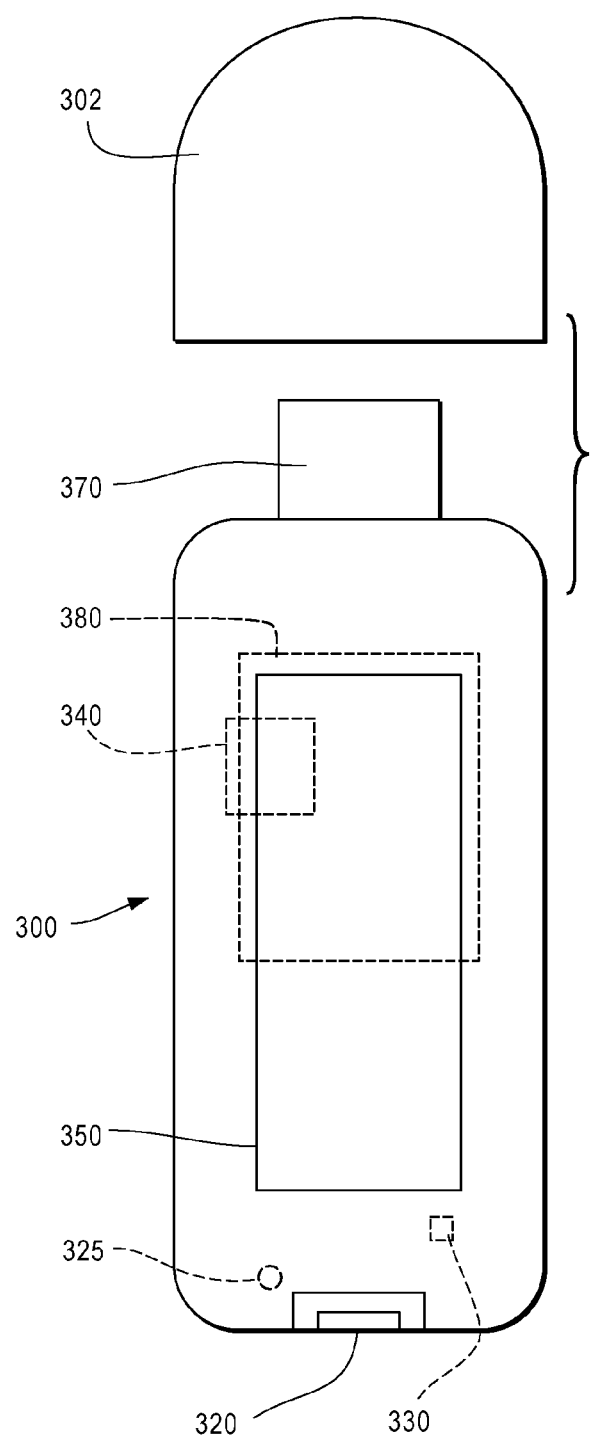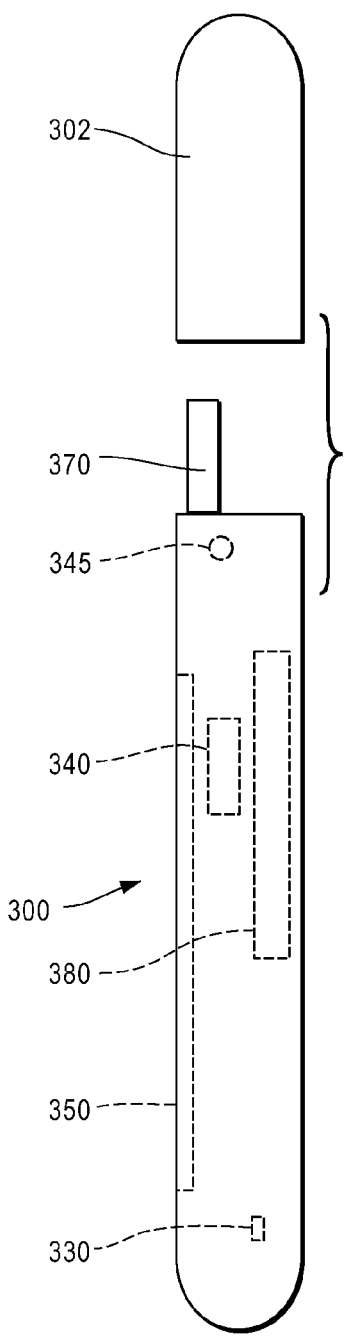

SYSTEMS AND METHODS FOR PREDICTING AMBIENT TEMPERATURE IN A FLUID ANALYTE METER

CROSS-REFERENCE TO RELATED APPLICATIONS

This application is a U.S. national stage of International Application No. PCT/US2009/059430, filed Oct. 2, 2009, which claims priority to and the benefits of U.S. Provisional Application No. 61/233,372, filed Aug. 12, 2009, U.S. Provisional Application No. 61/200,568, filed Nov. 28, 2008, U.S. Provisional Application No. 61/160,084, filed Mar. 13, 2009, and U.S. Provisional Application No. 61/102,661, filed Oct. 3, 2008, each of which are hereby incorporated by reference herein in their entireties.

FIELD OF THE INVENTION

The present invention generally relates to the prediction of ambient temperatures in fluid analyte meters powered by battery, and more particularly, to the prediction of ambient temperature readings during various states of a fluid analyte meter.

BACKGROUND OF THE INVENTION

The quantitative determination of analytes in body fluids is of great importance in the diagnoses and maintenance of certain physiological conditions. For example, lactate, cholesterol, and bilirubin should be monitored in certain individuals. In particular, determining glucose in body fluids is important to individuals with diabetes who must frequently check the glucose level in their body fluids to regulate the glucose intake in their diets. The results of such tests can be used to determine what, if any, insulin or other medication needs to be administered. In one type of testing system, test sensors are used to test a fluid such as a sample of blood.

Many individuals test their blood glucose several times per day. Thus, the individuals often must carry with them a meter for determining the glucose concentration of their blood. The individuals may also carry with them other analyte-testing instruments, including test sensors, a lancet, disposable lancets, a syringe, insulin, oral medication, tissues, or the like. Thus, the individuals are able to perform testing of their blood glucose at different locations including their homes, places of employment, places of recreation, or the like. Carrying the meter and/or other analyte-testing instruments to these various locations may be inconvenient for the individual.

Blood glucose meters can be powered using different types of powering configurations such as batteries or adapters that can be plugged into a standard outlet. The use of batteries allows the device to have a level of portability and mobility without having to be near a power outlet, such as when a user is outside.

SUMMARY OF THE INVENTION

According to one embodiment, a meter is configured to determine an analyte concentration of a fluid sample. The meter includes a housing and a temperature sensor disposed within the housing. A processor is configured to receive temperature data from the temperature sensor upon the meter entering at least one of a charge state and a discharge state. The processor is further configured to predict at least one temperature value that approximates the ambient temperature outside of the housing. The at least one predicted temperature value is based on stored historical temperature data associated with the temperature sensor such that the predicted temperature value remains constant if a recently received temperature value remains within predetermined upper and lower temperature thresholds and the recently received temperature value exceeds the at least one predicted temperature value.

According to another embodiment, a meter is configured to determine an analyte concentration of a fluid sample. The meter includes a housing having a display thereon with the display operable to display the analyte concentration of the fluid sample. A temperature sensor is disposed within the housing. A processor is configured to receive temperature data from the temperature sensor during a charge state of the meter. A prediction of the ambient temperature external to the housing is based on the received temperature data and an estimate of heating of the meter due to heat generated during the charge state of the meter. The estimate of heating includes charge current.

According to another embodiment, a meter module is configured to determine an analyte concentration of a fluid sample. The meter includes a housing, a temperature sensor disposed within the housing, and a processor configured to receive temperature data obtained from the temperature sensor upon the meter entering at least one of a charge state and a discharge state. The processor is further configured to predict at least one temperature value that approximates the ambient temperature outside of the housing. The at least one predicted temperature value is based on one or more of a first period of time associated with the meter being connected to an external charge source, a second period of time immediately after the meter is disconnected from the external charge source, a third period of time based on variable activity states associated with components within the meter; or any combination thereof.

According to another embodiment, a meter module is configured to determine an analyte concentration of a fluid sample. The meter module includes a printed circuit board having a temperature sensor disposed thereon and a processor disposed within the printed circuit board. The processor is configured to receive temperature data obtained from the temperature sensor during a charge state and a discharge state as determined by state data received by the processor. The processor is further configured to predict a temperature value that approximates an ambient temperature surrounding the meter module. The predicted temperature value is determined at least partially from the received temperature data and a temperature correction value. The temperature correction value is based on a first period of time associated with the meter being in the charge state. The first period of time has a predetermined upper time threshold such that if the first period of time exceeds the predetermined upper time threshold the temperature correction value is based on the predetermined upper time threshold and if the first period of time is less than the predetermined upper time threshold the temperature correction value is based on the first period of time.

According to another embodiment, a meter module is configured to determine an analyte concentration of a fluid sample. The meter module includes a printed circuit board having a temperature sensor disposed thereon and a processor disposed within the printed circuit board. The processor is configured to receive temperature data obtained from the temperature sensor during a charge state and a discharge state as determined by state data received by the processor. The processor is further configured to predict a temperature value that approximates an ambient temperature surrounding the meter module. The predicted temperature value is determined at least partially from the received temperature data and a temperature correction value. The temperature correction value is based on a predetermined rate of temperature decrease for the meter module such that if the received temperature data decreases at a rate similar to the predetermined rate of temperature decrease then the processor remains in a standard operating mode and if the received temperature data decreases at a rate that exceeds the predetermined rate of temperature decrease then the processor implements a suspect-value routine.

According to another embodiment, a meter module is configured to determine an analyte concentration of a fluid sample. The meter module includes a printed circuit board having a temperature sensor disposed thereon and a processor disposed within the printed circuit board. The processor is configured to receive temperature data obtained from the temperature sensor during a discharge state as determined by state data received by the processor. The processor is further configured to receive a discharge time associated with an instance at which the meter module entered the discharge state. The processor is further configured to predict a temperature value that approximates an ambient temperature surrounding the meter module. The predicted temperature value is determined at least partially from the received temperature data. The received temperature data includes a first temperature value recorded at a first time and a second temperature value recorded at a second time. The predicted temperature value is based on the second temperature value if the difference between the first time and the second time exceeds a predetermined first threshold and is further based on a temperature correction value applied to the second temperature value if the difference between the second time and the discharge time is below a predetermined second threshold.

According to another embodiment, a meter module is configured to determine an analyte concentration of a fluid sample. The meter module includes a printed circuit board having a temperature sensor disposed thereon and a processor disposed within the printed circuit board. The processor is configured to receive temperature data obtained from the temperature sensor during a discharge state as determined by state data received by the processor. The processor is further configured to receive a discharge time associated with an instance at which the meter module entered the discharge state. The processor is further configured to predict a temperature value that approximates an ambient temperature surrounding the meter module. The predicted temperature value is determined at least partially from the received temperature data. The received temperature data includes a first temperature value recorded at the discharge time and a second temperature value recorded at a second time after the first time. The processor is further configured to determine the difference between the first time and the second time, and if the difference exceeds a predetermined threshold time, a rate of temperature decrease is determined from temperature data recorded at predetermined time intervals subsequent to the second time. A first event subroutine is implemented by the processor if the rate of temperature decrease exceeds a predetermined rate threshold. The determination of the rate of temperature decrease is continued if the determined rate of temperature decrease is below the predetermined rate threshold such that the determination of the rate of temperature decrease continues until the occurrence of a predetermined event.

According to another embodiment, a meter module is configured to determine an analyte concentration of a fluid sample. The meter module includes a printed circuit board having a temperature sensor disposed thereon. A processor is disposed within the printed circuit board and is configured to receive temperature data from the temperature sensor during a charge state and a discharge state as determined by state data received by the processor. The processor is further configured to predict a temperature value that approximates an the ambient temperature surrounding the meter module. The predicted temperature value is based on a temperature value received from the temperature sensor, one or more predetermined target temperature rise values associated with power consumption data received by the processor, and a first temperature rise value associated with one of the predetermined target temperature rise values.

According to another embodiment, a meter module is configured to determine an analyte concentration of a fluid sample. The meter module includes a printed circuit board having an interface for receiving information including temperature data associated with a temperature sensor. The processor is disposed within the printed circuit board and is configured to receive the temperature data during a charge state and a discharge state as determined by state data received by the processor. The processor is further configured to predict a temperature value that approximates an the ambient temperature surrounding the meter module. The predicted temperature value is based on a temperature value associated with the received temperature data, one or more predetermined target temperature rise values associated with power consumption data received by the processor, and a first temperature rise value associated with one of the predetermined target temperature rise values.

According to another embodiment, a device is configured to determine an analyte concentration of a fluid sample. The device includes a housing, a temperature sensor disposed on or within the housing, and a processor configured to receive temperature data from the temperature sensor during a charge state and a discharge state associated with the device. The processor is further configured to predict a temperature value that approximates the ambient temperature outside of the housing. The predicted temperature value is based on a temperature value received from the temperature sensor, one or more predetermined target temperature rise values associated with power consumption data received by the processor, and a first temperature rise value associated with one of the predetermined target temperature rise values.

According to a further embodiment, a system for determining an analyte concentration in a fluid sample includes a test sensor and a meter. The test sensor includes a fluid-receiving area for receiving a fluid sample, the fluid-receiving area containing a reagent that produces a measurable reaction with an analyte in the sample, the test sensor having a test-sensor reaction temperature corresponding to the reaction between the reagent and the analyte. The meter includes an opening configured to receive the test sensor and a measurement system configured to determine a measurement of the reaction between the reagent and the analyte. The meter also includes a temperature-measuring system configured to determine the test-sensor reaction temperature by taking a plurality of temperature measurements after the test sensor is received into the opening and fitting the plurality of temperature measurements to a model that accounts for heat transfer between the meter and the test sensor. The meter then determines a concentration of the analyte in the sample using the measurement of the reaction and the measurement of the test-sensor reaction temperature.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 1 illustrates a fluid analyte system including a device and a meter module according to one embodiment.

FIG. 2 illustrates a fluid analyte system including an integrated device that provides a measurement system and a user interface according to another embodiment.

FIG. 3a illustrates a portable fluid analyte device with a USB interface according to another embodiment.

FIG. 3b illustrates a side view of the portable device of FIG. 3a.

FIG. 4b illustrates a side view of the portable device from FIG. 4a.

Figure 4A:
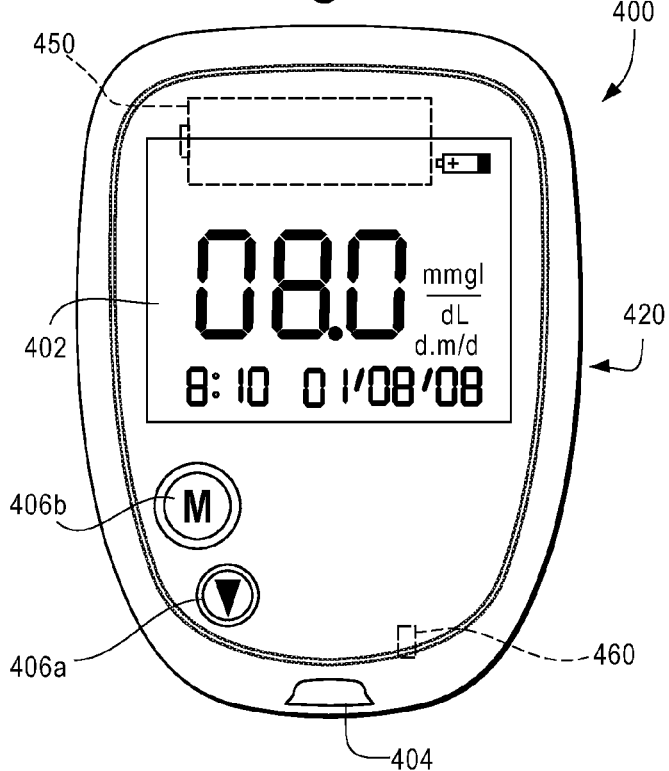
FIG. 4a illustrates a front view of a portable device with a display and a battery according to another embodiment.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention.

DETAILED DESCRIPTION

Measurement of blood glucose concentration is typically based on a chemical reaction between blood glucose and a reagent. The chemical reaction and the resulting blood glucose reading as determined by a blood glucose meter is temperature sensitive. Therefore, a temperature sensor is typically placed inside a blood glucose meter. The calculation for blood glucose concentration in such meters typically assumes that the temperature of the reagent is the same as the temperature reading from a sensor placed inside the meter. However, if the actual temperature of the reagent and the sensor are different, the calculated blood glucose concentration will not be accurate. An increase in temperature or the presence of a heat source within or near a blood glucose meter will generally result in erroneous blood glucose measurements.

Batteries available for use in blood glucose meters can include rechargeable batteries. The use of a rechargeable battery for a blood glucose meter requires the battery to have a charge for the meter to function.

A system and method for predicting an ambient temperature for use in a fluid analyte meter, such as a meter for testing blood glucose concentrations, is disclosed herein. A temperature sensor internal or embedded in the housing of a fluid analyte meter can provide an estimate of the ambient temperature in or surrounding a fluid analyte meter. In certain embodiments, the temperature measured by the temperature sensor is adopted as the temperature of a fluid sample placed into the meter for analysis. The measured temperature value from the temperature sensor is then used in the determination of the analyte concentration of the fluid sample. The temperature of the fluid sample is assumed to be the same as the ambient temperature of the surrounding air prior to sample being placed in or near the fluid analyte device. It is therefore desirable that the temperature measured by the temperature sensor correctly estimate the ambient temperature. Otherwise, inaccuracies will be introduced into the determination of the analyte concentration of the sample.

A fluid analyte device may include various heat-generating elements such as a rechargeable battery, a screen that may also include a backlight or other form of illumination, a port light, a processor, a microcontroller, or a charger integrated circuit. It is also contemplated that a fluid analyte device may be plugged into a heat-generating device such as a battery charger, a port on a computer, or a portable device. The generation of heat within or through a connection to the fluid analyte device can cause temperature monitoring element(s) in the fluid analyte device to differ from the ambient temperature outside of the device. It is contemplated that certain embodiments within a fluid analyte device include methods that compensate for temperature changes due to heat generated internal to a fluid analyte device, such as, for example, heat generated by charging a battery associated with the device, heat generated from an external device interfaced with the fluid analyte device, or heat generated during various power consumption activities or states of the fluid analyte device.

The present disclosures can be useful in temperature-sensitive health monitoring systems including monitoring systems based on a modular architecture such as the systems disclosed in U.S. patent application Ser. No. 12/129,555, filed May 29, 2008, entitled, "Architecture For Health Monitoring Systems", the contents of which is hereby incorporated by reference herein in its entirety.

FIGS. 1 to 4a-b and 25 illustrate certain embodiments of fluid analyte systems, such as blood glucose meters. The systems can include electrochemical test-sensors that are used to determine concentrations of at least one analyte in a fluid. Analytes that may be determined using the device include glucose, lipid profiles (for example, cholesterol, triglycerides, LDL and HDL), microalbumin, hemoglobin $Al_C$, fructose, lactate, or bilirubin. The present invention is not limited, however, to devices for determining these specific analytes and it is contemplated that other analyte concentrations may be determined. The analytes may be in, for example, a whole blood sample, a blood serum sample, a blood plasma sample, or other body fluids like ISF (interstitial fluid) and urine.

Although the meters of the illustrated embodiments are generally rectangular, it should be noted that the cross section of the meters used herein may be other shapes such as circular, square, hexagonal, octagonal, other polygonal shapes, or oval. A meter is typically made of a polymeric material. Non-limiting examples of polymeric materials that may be used in forming the meter include polycarbonate, ABS, nylon, polypropylene, or combinations thereof. It is contemplated that the meter may be made using non-polymeric materials.

According to certain embodiments, test-sensors for the systems are typically provided with a capillary channel that extends from the front or testing end of the sensors to biosensing or reagent material disposed in the sensor. When the testing end of the sensor is placed into fluid (for example, blood that is accumulated on a person's finger after the finger has been pricked), a portion of the fluid is drawn into the capillary channel by capillary action. The fluid then chemically reacts with the reagent material in the sensor so that an electrical signal indicative of the analyte (for example, glucose) concentration in the fluid being tested is supplied and subsequently transmitted to an electrical assembly.

Other examples of fluid analyte systems are discussed in U.S. application Ser. No. 12/129,547, filed May 29, 2008, entitled, "System and Method for Managing Health Data", and U.S. application Ser. No. 12/129,185, filed May 29, 2008, entitled, "Rapid Charging and Power Management of a Battery-Powered Fluid Analyte Meter", the contents of which are each incorporated by reference herein in their entireties.

FIG. 1 illustrates an exemplary fluid analyte measurement system 100 including a meter module 110 with a port 120 for receiving and analyzing a fluid sample on a test sensor 130. The fluid analyte measurement system 100 is generally surrounded by air that is at an ambient temperature that may fluctuate in response to various environmental conditions. The test sensor 130 is configured to receive a fluid sample that is subsequently analyzed using the meter module 110. The test sensor 130 includes a fluid-receiving area (not shown) for receiving the fluid sample. A user may employ a lancet or a lancing device to pierce a finger or other area of the body to produce a fluid sample at the skin surface. The user may then collect this sample (for example, a blood sample) by placing the test sensor 130 in contact with the sample. In certain embodiments, the fluid-receiving area contains a reagent that reacts with the sample to indicate the information related to an analyte in the sample, such as analyte concentration.

In one embodiment, the test sensor 130 is an electrochemical test sensor. An electrochemical test sensor typically includes a plurality of electrodes and a fluid-receiving area that contains an enzyme. The fluid-receiving area includes a reagent for converting an analyte of interest—for example, glucose—in a fluid sample—for example, blood—into a chemical species that is electrochemically measurable. The reagent typically contains an enzyme, such as glucose oxidase, which reacts with the analyte and with an electron acceptor such as a ferricyanide salt to produce an electrochemically measurable species that can be detected by the electrodes. Other enzymes may be used to react with glucose such as glucose dehydrogenase. In general, the enzyme is selected to react with the desired analyte or analytes to be tested so as to assist in determining an analyte concentration of a fluid sample. If the concentration of another analyte is to be determined, an appropriate enzyme is selected to react with the analyte.

In another embodiment, the test sensor 130 is an optical test sensor. Optical test sensor systems may use techniques such as transmission spectroscopy, absorption spectroscopy, diffuse reflectance, fluorescence spectroscopy, fluorescence resonance energy transfer, combinations thereof, and others for measuring the analyte concentration. An indicator reagent system and an analyte in a sample of body fluid react to alter light that is directed to the sensor 130. The degree of light alteration is indicative of the analyte concentration in the body fluid.

In FIG. 1, the meter module 110 receives and engages the test sensor 130. The meter module 110 measures the concentration of analyte for the sample collected by the test sensor 130. The meter module 110 can include contacts for the electrodes to detect the electrochemical reaction of an electrochemical test sensor. Alternatively, the meter module 110 can include an optical detector to detect the degree of light alteration for an optical test sensor. To calculate the actual concentration of analyte from the electrochemical or optical reaction measured by the meter module 110 and to generally control the procedure for testing the sample, the meter module 110 employs at least one processor 140, which may execute programmed instructions according to a measurement algorithm. Data processed by the processor 140 can be stored in memory 150. The meter module 110 may also use the same or a different processor for various operations, such as, for example, power management or temperature functions, including executing routines for temperature prediction of ambient temperature. Furthermore, the meter can include a user interface 160 having a display—for example, a liquid-crystal display, light-emitting diode display, or the like. Pushbuttons, a scroll wheel, touch screens, or a combination thereof, can also be provided as a part of the user interface 160 to allow a user to interact with the meter module 110. The display typically shows information regarding the test results, the testing procedure and/or information in response to signals input by the user.

The meter module 110 and/or the portable device 190 can include a processor and an interface 160, 175 to assist with the downloading and/or analysis of data, for example, blood glucose readings and time-stamp information, retrieved or stored on the respective devices.

Although the meter module 110 can store test results and provide the user interface 160 to display test results, it is contemplated that certain embodiments include a data-management software 192 operating on a portable device 190 to provide more advanced functionality for managing, processing, and displaying test results and related information. The portable device 190 can be sized to be easily carried, transported, and stored by an individual. The portable device 190 can include a memory, or data storage, 194, such as flash memory, Electrically Erasable Programmable Read-Only Memory (EEPROM), or the like. The memory 194 can be configured to include a combination of storage technologies. The test-related data collected by the meter module 110 can be downloaded to the portable device 190 for use with a data-management software 192 stored in memory 194. In certain embodiments, the meter module 110 includes an interface element 170 that enables the meter module 110 to connect with the portable device 190 through interface element 175. Examples of connections between the interface elements 170, 175 may include USB- or RFID-related elements.

The meter module 110 can have a power supply such as a rechargeable battery 180, which may be recharged via the connection of the meter module 110 with the portable device 190 or connections to another power source. The portable device 190 can also have a power supply such as a rechargeable battery 185, which can be recharged using a connection to an external device having a power source. For example, power can be transferred using a USB connection between the external device and the portable device 190. When the portable device 190 and the meter module 110 are connected, the battery 185 can be used to recharge the rechargeable battery 180 which powers the meter module 110, or vice versa. The meter module 110 may also be powered via the portable device 190.

It is contemplated that other devices or methods can be used to recharge a battery as are known in the field of the present disclosure. It is further contemplated that a meter module, portable meter, or a non-portable meter can be operated with a non-rechargeable battery or other known power sources appropriate for the size of the fluid-analyte meter or module.

It is contemplated that in certain embodiments an integrated fluid analyte device 200, as illustrated in FIG. 2, can incorporate the components and functions of the portable device 190 with the components and functions of the meter module 110. Accordingly, the integrated device 200 can receive an analyte-test sensor 230 via a port 220. The integrated device 200 can also include a processor 240 that calculates the concentration of analyte in the sample collected by the test sensor 230. The processor 240 in the integrated device 200 can also process information from the detection of a reaction between the sample and a reagent on the test sensor 230. The test results are stored in a memory 294 of the integrated device 200. The memory 294 may have a capacity in the range of about 500 MB to about 2 GB. The integrated fluid analyte device 200 can also include a user interface 260 that is used to display the test results and to enter input for various display options.

In certain embodiments, the integrated device 200 can be a portable blood glucose meter that provides data processing and display features. Users can employ the integrated device 200 to provide a blood sample via the test sensor 230 and can further access more sophisticated presentations of blood glucose test data from the integrated device 200 without launching data-management application on a separate processing device 20. However, as hardware limitations or the size of the device and associated elements may still prevent all desired functionality to be incorporated into the integrated device 200, the integrated device 200 retains the ability to launch the data-management application on a larger processing device 20 and to provide the user with functionality not available on the integrated device.

It is contemplated that the integrated device 200 can connect wirelessly to more than one type of processing device 20, including a laptop PC and mobile communication devices. In certain embodiments, interface element 270 associated with the integrated device 200 connects with interface element 26 of the processing device 20 to allow data transfer from the integrated device 200 to the processing device 20. The processing device 20 may already include data management software or the data management software 292 from the integrated device 200 can be used to analyze collected data. The processing device 20 can further include a processor, a user input device 24, and a display 22 to assist with the downloading and/or analysis of data, for example, blood glucose readings and time-stamp information, retrieved from the integrated device 200. In general, the portable device 200 may be integrated with varying levels of functionalities, such as user interface features and measurement system capabilities. However, any device employing components and functions of the portable device 200 may include a user interface, even if it does not incorporate components and functions of the meter module 110.

FIGS. 3a and 3b illustrate an exemplary embodiment of a fluid analyte meter. Fluid analyte meter 300 can include some or all of the functionalities and components discussed for the embodiments described in FIGS. 1 and 2. For example, the fluid analyte meter 300 can be a portable blood glucose meter that is an integrated device with certain data processing and display features. A user can employ the fluid analyte meter 300 to analyze a blood sample by inserting a test sensor into port 320. A port light, such as, a port light emitting diode 325 may be disposed near the port 320 to illuminate the port area and assist the user with inserting the test sensor. The fluid analyte meter 300 can also include a battery 380 that may be recharged by a connection via a USB interface element 370 to either a processing device 20 (FIG. 2), such as a PC, or other external power supply. If a rechargeable battery is used, a charging integrated circuit 345 may be included in meter 300 for recharging the battery 380. In certain embodiments, a battery may be disposed in a cap 302, which fits over the USB interface element 370. The meter 300 can also include a display 350 that provides information to a user of the meter 300. For example, the display 350 can include information on the battery strength, a calculated analyte concentration, historical analyte concentrations, date and time data, and power on/off information.

The fluid analyte meter 300 can also include one or more thermistors or other types of temperature sensing devices. For example, a thermistor 330 can be disposed near the port 302 where the test sensor is inserted. A microcontroller with an embedded temperature sensor 340 can also be disposed within the meter 300. The thermistor 330 and/or temperature sensor 340 are connected to a processor or a microcontroller of the meter 300 to allow temperature readings to be collected. The meter 300 may also use the same or a different microcontroller or processor for power management, temperature prediction operations, data transfer operation, or to execute other routines associated with the meter 300. For example, temperature prediction algorithms can be implemented on the microcontroller or processor to determine an accurate ambient temperature for use in calculating an analyte concentration.

Figure 4B:
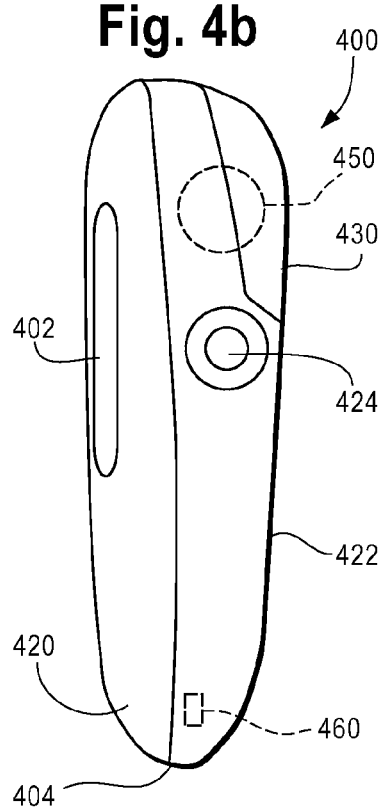

Referring to FIGS. 4a and 4b, another exemplary embodiment of a fluid analyte meter 400 is illustrated according to an embodiment of the present disclosure. The meter 400 can include some or all of the elements discussed for the embodiments described in FIGS. 1-3. The meter 400 is desirably sized so that it may fit generally within a user's purse or pocket. Thus, it is desirable, though not necessary, that the meter 400 have a long-dimension of less than approximately 2 to 3 inches to enhance portability. It is also desirable that the meter 100 have a footprint area of less than about 6 to 9 in$^2$. The meter 400 may even have a footprint area in the range of about 3 in$^2$. It is contemplated that in certain embodiments the meter 400 or the other meters described herein may be configured with different dimensions. It is further contemplated that in certain embodiments a meter may or may not be portable.

As shown in FIGS. 4a and 4b, the meter 400 includes a display 402 visible through a front portion 420, a test-sensor dispensing port 404, and a plurality of buttons 406a, 406b. After a user places a fluid—for example, his or her blood—on a test-sensor, the glucose level is determined by the meter 400, which displays the glucose reading on the display 402. The display 402 may display other information besides the analyte concentration. The user may then press user-interface buttons 406a, 406b to mark the reading accordingly, based on, for example, whether the reading was taken before or after eating. The glucose reading is then stored in the meter's memory device. The user may then go back at a later time to review and compare glucose readings.

The meter 400 typically includes a microprocessor or the like for processing and/or storing data generated during the testing procedure. The meter 400 may also use the same or a different microprocessor for power management or temperature operations, including executing routines to control recharging operations of the meter 400 for battery-operated devices and for implementing temperature prediction algorithms in assessing ambient temperatures.

The test sensor dispensing port 404 is adapted to receive and/or hold a test sensor and assist in determining the analyte concentration of a fluid sample. The display 402 can include, for example, light emitting diode (LED), organic light emitting diode (OLED), liquid-crystal display (LCD) with backlight, thin film transistor (TFT), a segmented display, or other types of displays. The type of display can have minimal or significant effects on the amount of energy used by a meter.

The display 402 may generally span a significant portion of the surface of the meter 400, which is especially desirable for a meter 400 that is relatively small and compact. For example, the display area may cover up to or more than 50 percent of the surface area of the front portion 420. A relatively large display 402 assists in the readability of the information displayed on the display 402.

The meter 400 may be powered by a main power supply, a battery, or any other suitable power source. The main power supply may include internally operated AC and/or DC power supplies. It may be desirable that the meter 400 be powered by a battery 450 due to the portable nature of the meter 400. A battery housing 430 may be located in a back portion 422 or within the front portion 420 of a meter 400.

In certain embodiments, the battery for the meter 400 is rechargeable via a main power source that can be connected to the meter 400 through a power adapter receptacle 424. Different types of rechargeable battery configurations may be used to power the meter 400 including, for example, lithium ion (Li-Ion), lithium polymer (Li—Po), nickel cadmium (NiCd) or nickel metal hydride (NiMH).

For certain battery-powered meter 400 configurations, the battery 450 remains within the battery housing 430 during charging. For example, the meter 400 can be charged by plugging one end of a special adapter into the power adapter receptacle 424 of the meter 400 while the battery remains in the battery housing 430. A second end of the special adapter is then plugged into the AC power outlet to charge the battery. In certain embodiments, the meter 400 may be powered by connecting one end of the special adapter to a source on a computer, such as a Universal Serial Bus (USB) port, and the second end to the power adapter receptacle 424. It is further contemplated that in certain embodiments, a meter 300, 400 or other meter embodiments can include an single interface or adapter configured for handling both power and data transfer operations.

Battery chargers are capable of providing a fast or rapid charge to a rechargeable battery by using a higher charging current than would be typically used to charge the battery, with minimal degradation of the battery. This principal of rapid charge of a battery also applies to battery charger integrated circuits. In certain embodiments, a very short charge time for a battery at a high charging rate can provide sufficient energy to a meter battery to allow for several blood glucose concentration tests. However, the use of rapid charging for a blood glucose meter battery can lead to an increase in the temperature of the meter and change the resulting blood glucose concentration reading that is output by the meter. Also, any prolonged charging of a battery located within a meter can lead to an increase in the ambient temperature within and surrounding the meter.

It would be understood within the field of the present disclosures that elements and/or components of the meter modules and/or portable devices described herein can be embodied in a single device or in multiple devices in various configurations of elements and/or components. Furthermore, it would be understood that the devices described herein can be used in both portable or non-portable fluid analyte meters. Thus, while the meter modules or portable devices described herein may be portable, the present disclosures can also be applied to non-portable fluid analyte meters.

Figure 5:
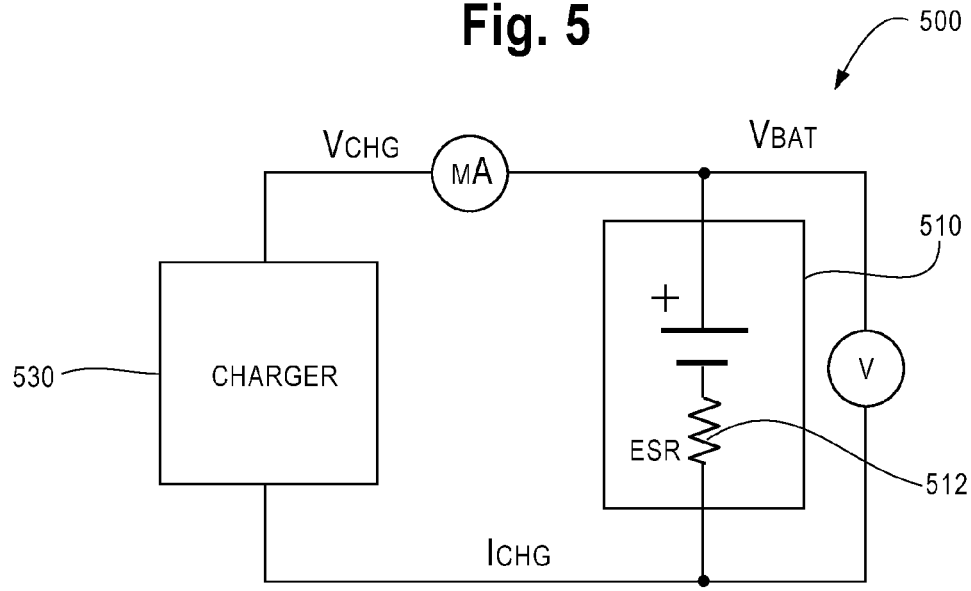
FIG. 5 illustrates a charging circuit for a rechargeable battery according to another embodiment.

Referring now to FIG. 5, a schematic of a charging circuit 500 for a rechargeable battery 510 is illustrated according to certain embodiments. The illustrated charging circuit 500 demonstrates battery temperature rise during the charging of the battery 510, such as may be experienced during the charging of a blood glucose meter battery. A temperature rise in the battery 510 is proportional to the charge current and the charge time. Furthermore, the battery 510 has an internal equivalent series resistance (ESR) 512 that causes the heat dissipation of the battery. ESR varies according to the type of battery. The charging circuit 500 further includes a charger 530, such as an external power source, connected to the battery 510.

Figure 6:
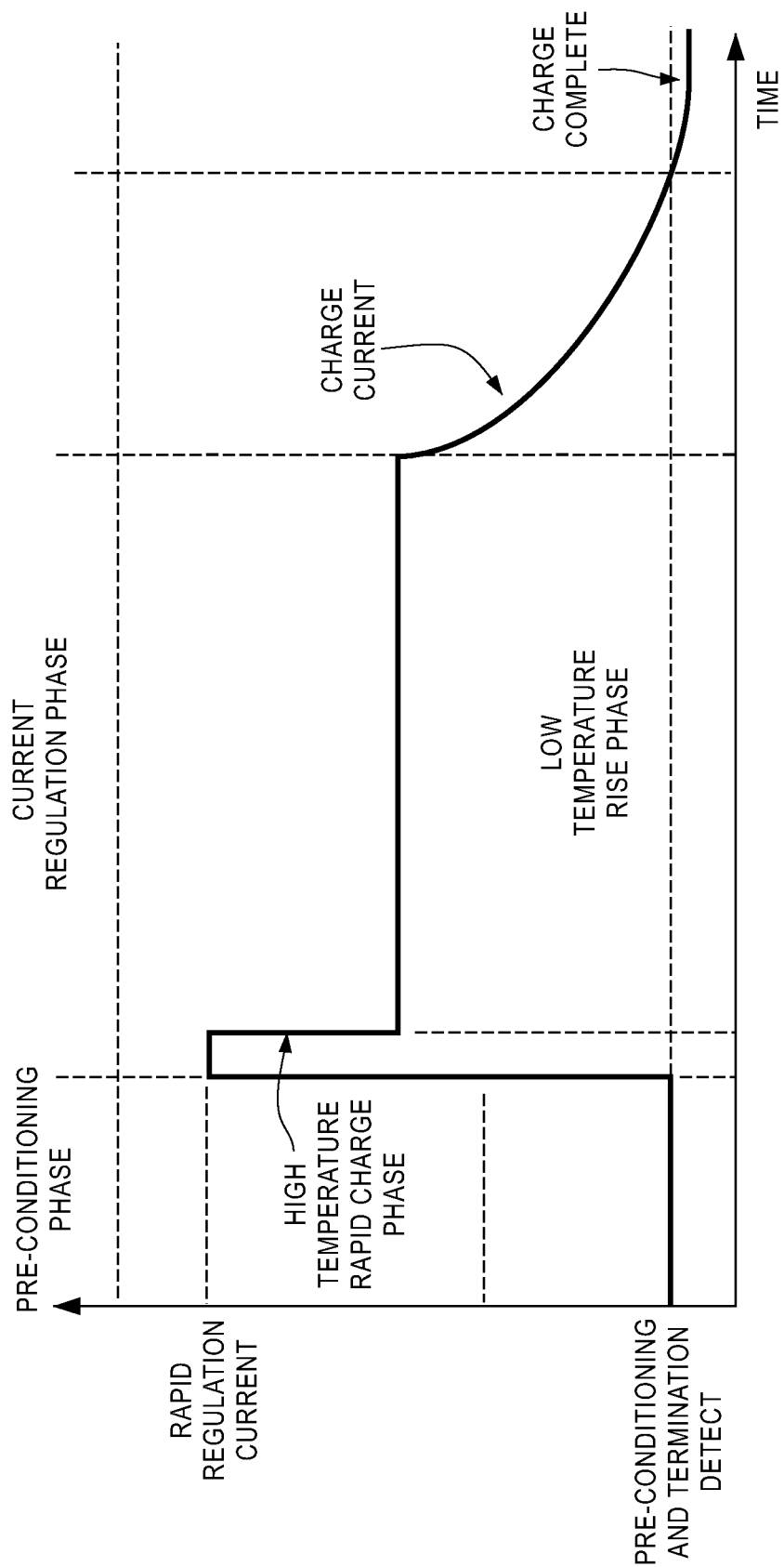
FIG. 6 illustrates a charging algorithm having a high temperature-rise phase used to charge a battery according to another embodiment.

Referring now to FIG. 6, a standard charging algorithm is illustrated that begins with a pre-conditioning phase, followed by a current regulation phase that may include a rapid charge mode or high current regulation phase and/or a low or standard current regulation phase. As long as the battery receives energy from an external power source, such as, for example, a battery charger 530 or portable device 190, the battery can continue charging until the battery reaches a regulation voltage at which point the charge current decreases until the charge is considered complete. During the preconditioning and current regulation phase(s) the battery is generating heat within the fluid analyte meter that increases the temperature measured by temperature sensor(s) or thermistor(s) located inside or near the surface the fluid analyte meter.

As previously discussed and illustrated, a fluid analyte meter can include several exemplary heat-generating elements, such as, for example, a rechargeable battery, a charger integrated circuit, an illuminated display, a display backlight, a port LED, a processor, and/or a microcontroller. The influence of these elements can cause variations between actual ambient temperature and measurements of temperature from temperature sensing devices associated with a meter. However, the determination of an analyte concentration for a fluid sample, such as, glucose, is temperature sensitive. Therefore, temperature readings that are not representative of the actual ambient temperature—and thus, the fluid sample temperature—can cause inaccuracies in the determination of analyte concentration. The exemplary embodiments illustrated in FIGS. 3a, 3b, 4a, and 4b represent fluid analyte meter arrangements in which a heat-generating element may lead to inaccuracies for raw temperature readings taken to represent the ambient temperature. For example, the close proximity of the batteries 380, 450 and display 350, 402 to the thermistors 330, 460 and temperature sensor 340 can lead to increases in the measured temperature despite there being no increase in the actual ambient temperature. The variations between the measured and actual ambient temperature can further vary depending on the meter element that is operating and generating the heat. For example, varying amounts of heat—and potential error—will be introduced depending on whether the battery is being charged or discharged, the display is being lit, data is being transferred to a portable device, or any combinations thereof. Further examples that affect heat generation include size of a battery, the type of display, or the type of processor or microcontroller.

In certain embodiments, predicting ambient temperature for subsequent input into the determination of a fluid analyte concentration is completed using historical temperature data (e.g., data collected from a sensor) that is stored in a memory. For example, historical temperature data may be collected by making temperature measurements at periodic intervals while the fluid analyte meter in an ON mode and the measurements can be stored in a memory (e.g., in an array). The temperature measurements can be made using a thermistor or temperature sensor similar to those described in FIGS. 3a-b and 4a-b.

Figure 7:
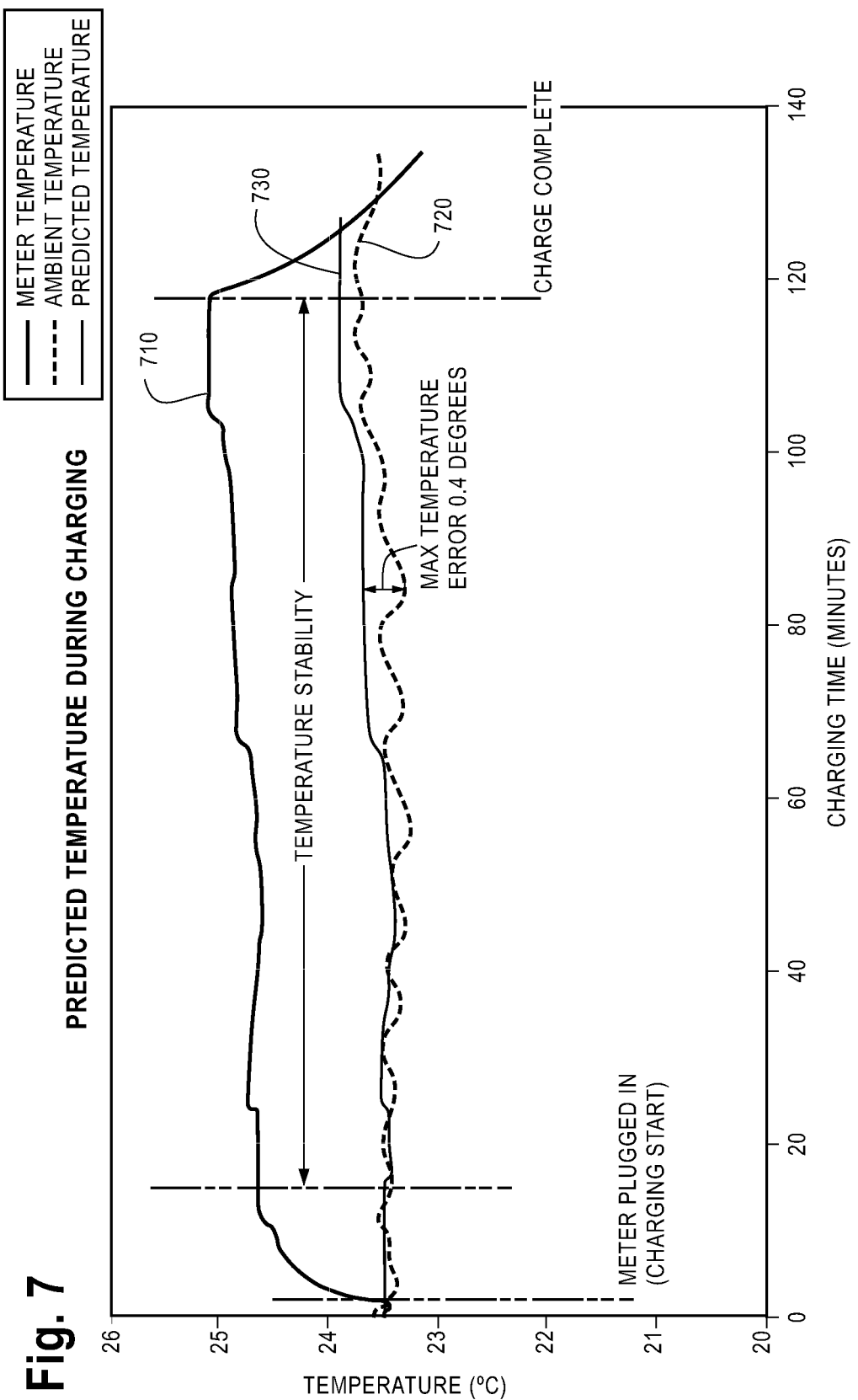
FIG. 7 illustrates a temperature prediction during charging of a battery according to another embodiment.
Figure 8:
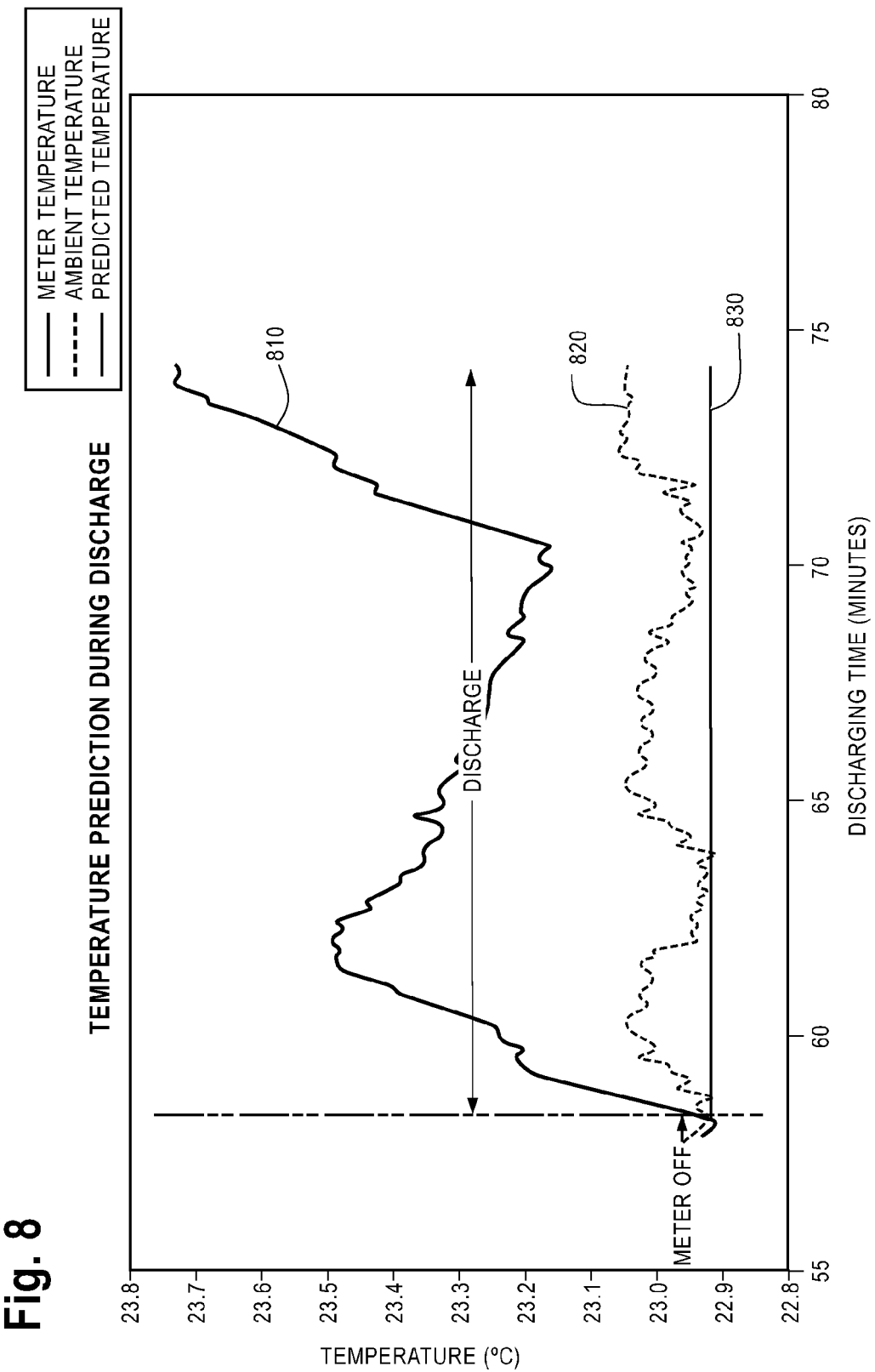
FIG. 8 illustrates a temperature prediction during discharge of a battery according to another embodiment.

FIGS. 7 and 8 illustrate temperature predictions for use in determining temperature-sensitive fluid analyte concentration. FIG. 7 illustrates examples of temperature predictions during the charging of a rechargeable battery. The thick solid line represents periodic temperature readings that are taken by a thermistor or temperature sensor within the fluid analyte meter—that is, meter temperature 710. A rate of change of the periodic meter temperature readings can be determined using the most recent temperature measurement and the temperature measurement just before the most recent measurement. Rate of change of the meter temperature can also be calculated using different combinations of recent temperature readings. For example, the rate of change could include the most recent temperature readings and the second or third prior temperature measurement. The meter temperature measurements can be made throughout the charging cycle including at the beginning of the charge through the completion of the charge and can also continue through the return of the meter to a stable temperature.

As illustrated in FIG. 7, at the beginning of a charge cycle (that is, charging time=0 minutes), the meter can measure and "lock in" the meter temperature and assign that value as an initial predicted temperature, $T_{PREDICTED}$. The value of the initial $T_{PREDICTED}$ remains the same until meter thermal stability is achieved—that is, $T_{PREDICTED}$ is not changed until the rate of change of the measured temperature stays below a threshold value after a series of consecutive temperature measurements, such as, for example, after three consecutive measurements. In the example of FIG. 7, the predicted temperature 730 is illustrated to remain constant until the charging time is approximately equal to fifteen minutes.

The various phases of meter temperature (e.g., meter plugged in, temperature stability, charge complete) illustrated in FIG. 7 correlate with the charge phases illustrated in FIG. 6. For example, the initial state of temperature rise in FIG. 7 correlates with the pre-conditioning phase and may also correlate with the rapid charge phase in FIG. 6. The temperature stability phase of FIG. 7 correlates with the low-temperature rise phase of FIG. 6. The charge complete phases of FIGS. 6 and 7 correlate with each other, as well, and represent a low current or no-charging phase, and thus, a decreasing measured meter temperature 710.

In certain embodiments, the meter can take periodic meter temperature measurements every ten seconds during the rapid charge phase while monitoring for meter thermal stability. Periodic intervals either greater than or less than ten seconds can be used, as well. Following rapid charge, the meter may then enter into the low-temperature rise phase that is more commonly referred to as a regular charge phase. During the regular charge phase, the meter can take meter temperature readings over a longer interval than the rapid charge phase—for example, every thirty seconds instead of every ten seconds. The meter temperature measurements during the regular charge phase can continue at the regular interval until, similar to the rapid charge phase, meter thermal stability is established—for example, when a threshold rate of change is not exceeded for three or five consecutive measurements. Once a determination is made that meter thermal stability has been reached, the difference between the last measured meter temperature and the initial predicted temperature, initial $T_{PREDICTED}$, is calculated and this difference is assumed to be a constant $\Delta T$ as long as meter thermal stability is maintained. During the period of meter thermal stability, the predicted temperature 730 corresponding to each subsequent measured meter temperature is calculated as the measured meter temperature 710 minus the constant $\Delta T$. If the threshold rate of change of measured meter temperature is exceeded, and thus, meter thermal stability is compromised, the meter can terminate subtracting the constant $\Delta T$ from subsequent measured meter temperatures and instead "lock in" the last predicted temperature value—that is, the last measured meter temperature minus the constant $\Delta T$ before meter thermal stability was compromised—as the present $T_{PREDICTED}$. A constant predicted temperature 730 is then maintained until meter thermal stability is again achieved.

Referring again to FIG. 7, a method of temperature prediction is illustrated for an embodiment similar to the fluid analyte device described in FIG. 3. To illustrate the accuracy of the temperature predictions, ambient temperature 720 was experimentally determined using a temperature sensor separate from that used to measure meter temperature. Over an approximately two-hour charge time, the difference between the predicted temperature 710 and the ambient temperature did not exceed 0.4 degrees Celsius, which is within acceptable ranges for temperature error for determining fluid analyte concentration for analytes, such as, for example, glucose.

Once charging is complete, the meter enters into a cool down phase. During the cool down phase, the meter can lock in the last value of predicted temperature as the predicted temperature value. Meter temperature measurements can continue to be made at a similar interval as the regular charge phase to monitor for meter thermal stability. The interval for meter temperature measurements can also be increased or decreased depending on the expected behavior of the meter following charging and the type of monitoring that is desired. If the meter temperature 710 goes below locked in value of predicted temperature, the predicted temperature 730 is updated for the next series of meter temperature measurement to be the same as the measured temperature. When meter thermal stability is again achieved, the meter can then set the most recent meter temperature measurement to be the predicted temperature.

Following a charging phase or after a meter is turned on, the meter enters into a discharge phase. It is contemplated that in certain embodiments the meter will measure the meter temperature upon the meter being turned on. The temperature measurement can be made using a thermistor or temperature sensor, similar to those described in FIGS. 3a-4b, or other types of temperature sensing devices. Similar to the charging phase, the meter can continue taking periodic meter temperature measurements at intervals of, for example, thirty seconds.

FIG. 8 illustrates an example of predicting temperature during the discharge mode of a meter based on measurements from a fluid analyte device similar to the device shown in FIG. 3. In the illustrated embodiment, the predicted temperature 830 remains constant during the entire illustrated discharge phase from the approximate discharge times of 58 minutes to 74 minutes. Predicted temperature 830 is set equal to the measured temperature at the time when the meter goes from being in a OFF state to being turned ON—that is, at discharge time 58 minutes. During the period of discharge, the meter continues to measure the meter temperature 810. To illustrate the accuracy of the predicted temperature, an actual ambient temperature 820 was measured. The temperature plots on FIG. 8 show that predicted temperature 830 is within approximately 0.2 degrees Celsius of the actual ambient temperature.

For an actual meter, the only measurement typically made is the meter temperature 810. During the discharge phase, if the meter measures a temperature lower than the most recent predicted temperature value, the predicted temperature is set to equal the recently measured lower meter temperature. Otherwise, the meter maintains a constant predicted temperature, similar to the illustration of FIG. 8.

It is contemplated that in certain embodiments that predicted temperature during charging can be determined based on charge current and estimated heat dissipation. For example, an estimate can be made of the heating of a fluid analyte meter while the meter is charging. The heating can be determined using the following equation that accounts for the heating due to the charging current and heat dissipation:

$$\Delta T = \sum_{t_0}^{t_f} (K_1 i dt - K_2(T - T_0)dt) \quad \text{(Equation 1)}$$

where $\Delta T$=estimated temperature change
$t_0$=time at beginning of charging
$t_f$=time at end of charging because battery is full or power is removed
$T_0$=temperature measurement taken at beginning of charging, $t_0$
T=instantaneous temperature measurement
i=instantaneous charge current measurement
$K_1$=charge current heating constant
$K_2$=heat dissipation constant At the end of charging, the meter stores the $\Delta T$ determined using Equation 1 and the time at the end of charging. Fluid analyte concentration can then be determined for a fluid sample while the meter is in the discharge phase using a predicted temperature based on the temperature measurement taken at the beginning of charging, $T_0$, plus the estimated temperature increase, $\Delta T$. The estimated temperature increase, $\Delta T$, can be ignored once a certain time has lapsed after the end of charging. The amount of time lapsed can be determined experimentally and will be based on the heat dissipation characteristics of a meter. Otherwise, the heat dissipation immediately after charging but before the experimentally determined lapsed time has passed can be calculated using the second part of Equation 1 to estimate the temperature difference from the last measured meter temperature. The constants $K_1$ and $K_2$ are meter-specific constants for heating due to charge current and heat dissipation. $K_1$ and $K_2$ will vary depending on the heating of a meter due to charge current and the meter's heat dissipation characteristics. $K_1$ and $K_2$ can be readily determined experimentally for a given meter.

It is contemplated that in certain embodiments the temperature influence during discharge of a fluid analyte meter has minimal effects on the determination of analyte concentration. For example, it has been determined for a device similar to the one illustrated in FIG. 3 that the temperature increase over ambient temperature is less than about one or two degrees Celsius during discharge and charging without any connection of the meter to a portable device, such as a personal computer.

It is contemplated that in certain fluid analyte meters, heat-generating elements within the fluid analyte device, such as those used during analyte concentration tests, can cause the meter temperature to rise more than one degree Celsius above an ambient temperature measurement taken prior to the influence of the heat-generating element. To control the effects of temperature rise in determining an analyte concentration, the algorithm illustrated in FIG. 9 can be implemented on a processor or microcontroller within the fluid analyte device when a user is performing an analyte concentration test. The algorithm periodically measures and records the meter temperature in a memory for subsequent analysis to determine if the ambient temperature has changed and whether an acceptable predicted temperature is being used to determine analyte concentration.

Figure 9:
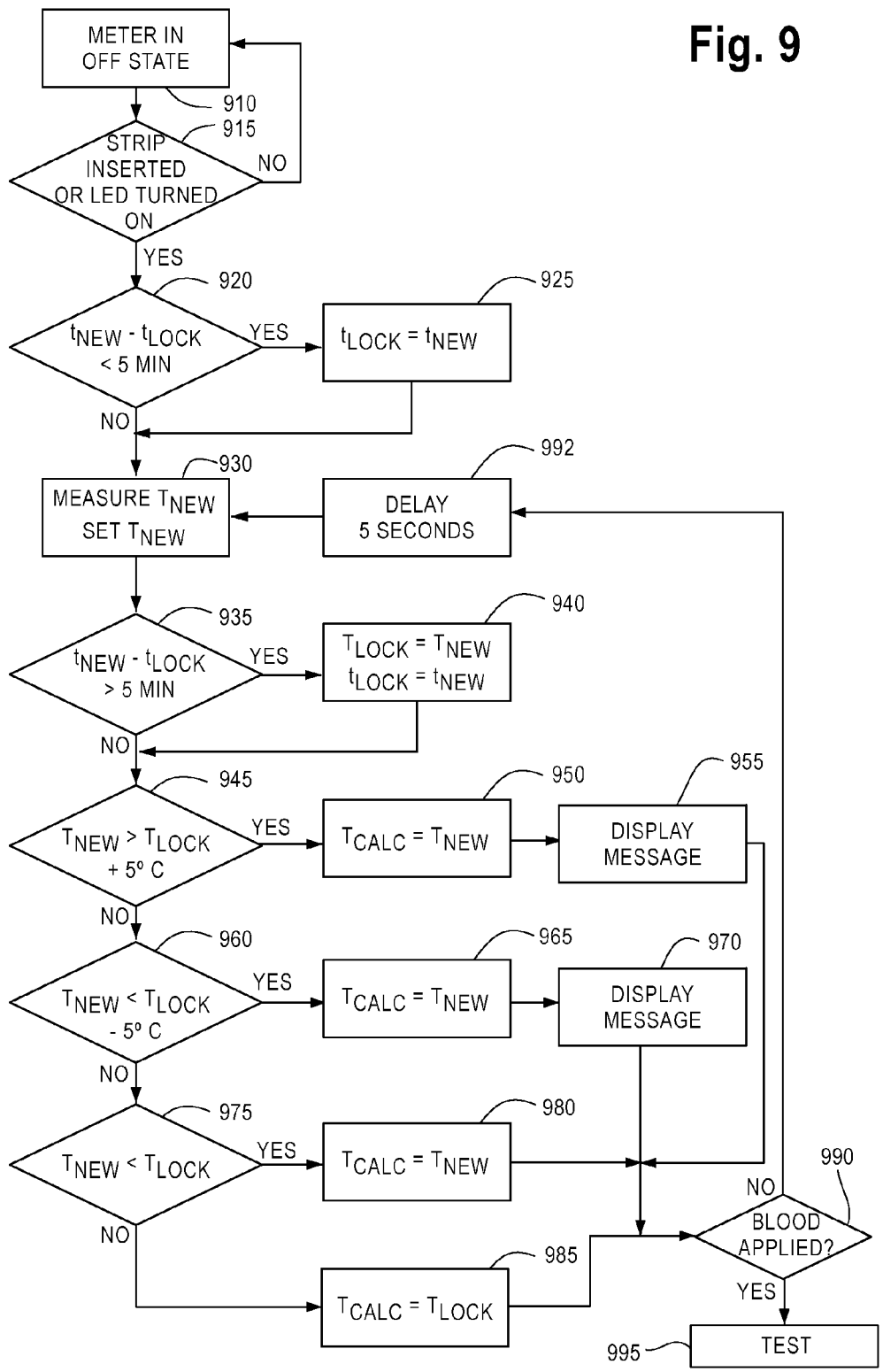
FIG. 9 illustrates a logical flow diagram of one method for predicting temperature during a battery discharge mode according to another embodiment.

Referring now to FIG. 9, a fluid analyte meter is initially in an OFF state 910. Prior to entering an OFF state, the meter can record and store into memory a temperature value, $T_{LOCK}$, which represents the last predicted temperature value for the meter. $T_{LOCK}$ is measured at time, $t_{LOCK}$, both of which can be recorded and stored into memory. The value of $T_{LOCK}$ taken at the time the meter is turned off will also be the initial value of predicted temperature upon the meter being turned ON. The term, $T_{LOCK}$, is a stored temperature value that is retained and represents the current predicted value of ambient temperature to be used in determining a fluid analyte concentration, such as, for example, blood glucose concentration. $T_{LOCK}$ is also compared to subsequent temperature sensor measurements to track temperature changes and check if there has been an environmental change for the meter. The term, $t_{LOCK}$, can represent a stored time value of the most recent time to which $T_{LOCK}$ is set, and can also represent a new time value when the meter enters into a test mode within a predetermined time period after the most recent recording of $t_{LOCK}$, as illustrated, for example, in steps 920 and 925.

At step 915, the logic flow of FIG. 9 proceeds to determine whether the meter has been turned ON. A test strip inserted into the meter, the use of lighting associated with the test port, the use of lighting elements associated with the display, or other heat-generating events associated with the meter could trigger the meter into an ON state. In certain embodiments, the meter does not enter into an OFF state, such as step 910, but rather may switch between different meter ON states. For example, after operating in a certain ON state, the meter may enter into a different ON state, such as a test mode, with the insertion of a test strip into the test port or the turning on of a port LED. If the meter has been turned ON, the algorithm proceeds to step 920. Otherwise, the algorithm loops back through steps 910 and 915 until a determination has been made that the meter is turned ON or has switch to a different ON state, such as the test mode. At step 920, a determination of whether the time from $t_{LOCK}$—that is, the time when the meter was turned off and the temperature, $T_{LOCK}$, was recorded—to the time the meter is turned ON is greater than or less than a predetermined period of time. In certain embodiments, if the difference between $t_{LOCK}$ and the time the meter is turned ON is less than five minutes the algorithm proceeds to step 925 and establishes a new value for $t_{LOCK}$ that is equal to the time at which the meter was turned ON. Otherwise, the value for $T_{LOCK}$ is maintained at the temperature value recorded at the time the meter was turned off. Steps 920 and 925 cover the scenario where a user performs two analyte concentration tests close to each other, for example, within five minutes, and it is desired to maintain the same value for $T_{LOCK}$ in both tests. If more than a predetermined period of time lapses since $t_{LOCK}$ (for example, more than five minutes), the time between the meter being last turned off and subsequently turned ON, then the algorithm proceeds to step 930 to measure a new temperature and eventually establish a new locked-in temperature. The predetermined period can vary depending on the physical properties of the meter, such as heat dissipation properties. In certain embodiments, the predetermined period will be greater than or less than five minutes. Furthermore, as explained above, rather than the meter cycling from an OFF state to an ON state, the meter can also proceed from one ON state to another ON state. For example, the meter could switch from a charge state to test mode or test state when a test strip is inserted into a test port.

At step 930, the meter measures and records a new temperature value, $T_{NEW}$, which is the most recent measured temperature value. $T_{NEW}$ is recorded at time, $t_{NEW}$, and will subsequently be compared to $T_{LOCK}$. Generally, whenever a new temperature value is recorded from a temperature sensor, the time of the temperature measurement is also recorded. At step 935, the difference between $t_{LOCK}$ and $t_{NEW}$ is determined. For the embodiment illustrated in FIG. 9, the locked temperatures are valid for five minutes, so if the difference between $t_{LOCK}$ and $t_{NEW}$ is over 5 minutes, a new lock is set by setting $T_{LOCK}$ equal to $T_{NEW}$ and $t_{LOCK}$ equal to $t_{NEW}$ in step 940. Again, it is contemplated that different time periods both greater than or less than five minutes can be used.

The value of $T_{LOCK}$ and $T_{NEW}$ is now compared with upper and lower temperature thresholds to determine a predicted temperature value to be used in the determination of analyte concentration, such as blood glucose concentration, and to determine whether the ambient temperature has changed. If the difference between $t_{LOCK}$ and $t_{NEW}$ is not greater than five minutes, then the meter proceeds to step 945 where $T_{NEW}$ is compared to an upper temperature threshold based on a predetermined temperature increase that is added to $T_{LOCK}$. If the most recent value of $T_{NEW}$ exceeds a predetermined upper temperature threshold, such as, the most recent value of $T_{LOCK}$ plus a predetermined temperature increase, the meter proceeds to step 950 where a term $T_{CALC}$ is set equal to $T_{NEW}$. From there the meter proceeds to step 955 where a message can be displayed to the user, such as, for example, a "READY" or a "CHANGE IN TEMPERATURE" message. If the most recent value of $T_{NEW}$ is not greater than the upper threshold, the meter proceeds from step 945 to step 960 where a determination is made of whether the most recent value of $T_{NEW}$ is less than a lower threshold, such as, the most recent value of $T_{LOCK}$ minus a predetermined temperature decrease. If the most recent value of $T_{NEW}$ is less than a lower temperature threshold, then the meter proceeds to step 965 where the term $T_{CALC}$ is set equal to $T_{NEW}$. The meter can then proceed to step 970 where a message can be displayed to the user, such as, for example, a "READY" message or a "CHANGE IN TEMPERATURE" message.

After displaying a message in steps 955 and 970, the meter can then proceed to step 990 where the meter checks to see if a fluid sample, such as, for example, blood was applied to the meter. In the embodiment illustrated in FIG. 9, the predetermined temperature increase and decrease are five degrees Celsius. In certain embodiments, the predetermined temperature increase or decrease can vary and can also be greater than or less than five degrees Celsius. In establishing upper and lower thresholds to apply to the decision steps 945 and 960, the predetermined temperature increase and decrease values can be selected to reflect a temperature change known to be due to environmental factor(s). For example, it may be known that the heat generated by a fluid analyte meter cannot increase the temperature of the device more than five degrees Celsius, and thus, when the temperature difference exceeds five degrees Celsius, the meter knows that the change in measured temperature is a change in the ambient temperature. The meter can then assign a new predicted temperature value.

At step 975, if the most recent value of $T_{NEW}$ is less than $T_{LOCK}$, the meter will proceed to step 980 where the term $T_{CALC}$ is set equal to $T_{NEW}$. From there the meter can proceed to step 990 where the meter checks to see if a fluid sample, such as, for example, blood was applied to the meter. At step 975, if the most recent value of $T_{NEW}$ is not less than $T_{LOCK}$, the meter then proceeds to step 985 where the term $T_{CALC}$ is set equal to $T_{LOCK}$. From step 985, the process then proceeds to step 990 to check if a fluid sample was applied to the meter, and then to step 995 where an analyte concentration test is conducted using the value determined for the term $T_{CALC}$.

As previously discussed, at step 990, a determination is made whether a fluid analyte sample (for example, blood sample) has been applied to the meter. If the determination is negative, the meter can proceed to step 992, where the algorithm is set for a predetermined delay period, such as, five seconds, before proceeding back to step 930 and going through another cycle of the algorithmic loop. In certain preferred embodiments of step 990, an analog engine signals a digital engine that a fluid analyte sample has been applied to the meter. For example, an analog signal can be generated from a fluid analyte sample, such as, for example, a blood sample, being placed in a port of a fluid analyte meter. The analog signal is sent to the digital engine that further processes information following receipt of the analog signal. The analog engine can also wait for the digital engine to report the most recent value for $T_{CALC}$, such as the values established at steps 950, 965, 980, and 985, before assessing whether a fluid analyte sample has been applied to the meter.

It is contemplated that in certain embodiments a temperature offset can be applied to the predicted temperature, $T_{CALC}$, before the value is used to determine analyte concentration. For example, in certain blood glucose meters or in embodiments similar to those illustrated in FIG. 3, it has been experimentally determined that heat generated by the meter during charge or discharge influences the temperature increase in the meter by a limited upper bound. Discharge is a state where the meter is turned on, but is not being charged. Charge is a state where the meter battery is being recharged by an external power source. In the exemplary device illustrated in FIG. 3, the heat generated through charge and discharge operations ranges consistently from zero to less than approximately one degree Celsius. To compensate for this known upper bound of temperature increase, an offset of 0.5 degrees Celsius can be subtracted from $T_{CALC}$ after any of steps 950, 965, 980, or 985, but before testing step 995. The offset can be desirable to at least partially account for bias associated with a known quantity of temperature increase due to heat-generating elements.

It is further contemplated that in certain embodiments, a user may change the time setting on the fluid analyte meter. In the event of a change in the time setting, the meter can account for the difference between the meter time after the change and the meter time before the change. The difference in time can then be reflected in the time recordings, such as, $t_{LOCK}$, so that certain predetermined time periods are not affected by the time change.

It is also contemplated that in certain embodiments temperature predictions can be made to correct for heat generation when a meter is operating in a data transfer mode. For example, the meter illustrated in FIG. 3 includes a USB port that allows direct connection of the meter to a personal computer or other computing device that allows a USB connection. It is contemplated that other types of direct connections can be incorporated into a meter, such as connections made by flash-memory type devices similar to a USB connection.

During the data transfer mode, the meter is transferring and/or receiving data from an external portable device. This operation leads to heat generation in the meter itself and generated heat from the portable device, such as a PC, being transferred to the meter. In certain embodiments, it is contemplated that two temperature sensors within the meter are monitored to determine a good prediction of the ambient temperature.

Figure 10:
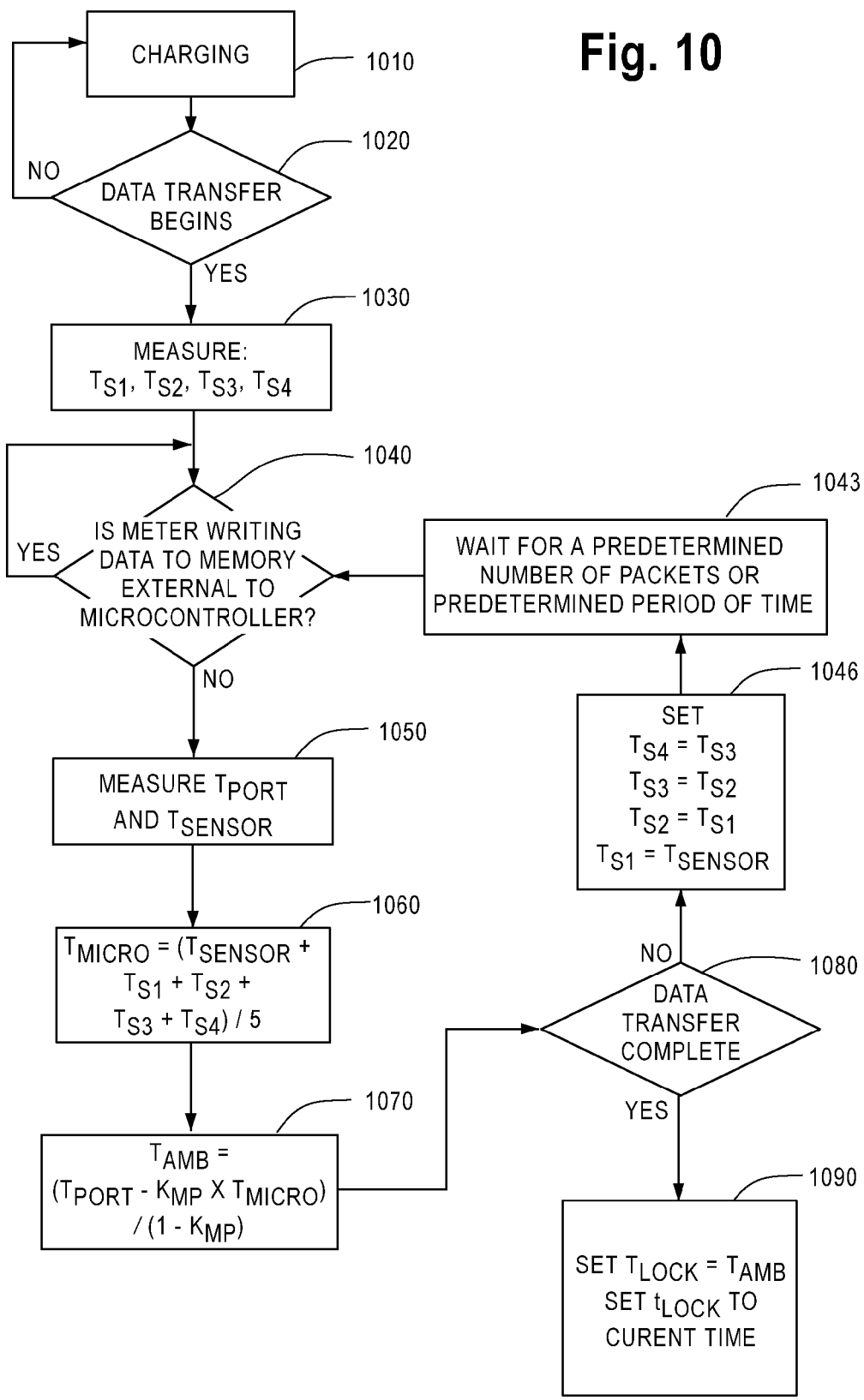
FIG. 10 illustrates a logical flow diagram of a method for predicting temperature during a data transfer mode according to another embodiment.

Referring now to FIG. 10, a meter state is illustrated for predicting ambient temperature for a fluid analyte meter in a data transfer mode, such as, for example, where data is modified on a mass storage device external to, but at least temporarily connected, to the meter. In certain embodiments, the meter can charge its battery while connected to a portable device containing the mass storage device. Charging can occur directly from power obtained from a number of source, such as, for example, a PC or a wall-type charger. FIG. 10 starts out at step 1010 in a charging mode and loops through decision step 1020 to determine if data transfer has been started. If data transfer has not begun, the meter loops from step 1020 back to charging step 1010.

If data transfer has started, the decision loop at step 1020 is exited and the logic flow moves to step 1030 where temperature measurements are made for the temperature sensing devices within the fluid analyte meter. At step 1030, up to four temperature measurements are taken for a temperature sensor over a period of time. Multiple temperature measurements over a short period of time (for example, in less than one minute) from a single sensor, while not necessary, may be desirable for certain sensing device that have more erratic or less consistent temperature measurements. For example, in the embodiment illustrated in FIG. 3, the temperature sensor 340 is inside the microcontroller or microprocessor and can have slightly erratic temperature measurements. To compensate for erratic temperature measure, step 1060 can be implemented in which the multiple temperature sensor readings for the microcontroller are later averaged into a single temperature value, $T_{MICRO}$.

In certain embodiments, two temperature sensing devices can be used, similar to the exemplary embodiment illustrated in FIG. 3. It is further contemplated that more than two temperature sensing devices can be used in a fluid analyte meter or meter module as described elsewhere herein and as would be understood by one skilled in the field of the present disclosure. At step 1040, the meter enters into a loop that continues until the data transfer is complete. For example, the meter will continue to loop until it completes writing data to the memory external to the microcontroller of the meter. If the data transfer is complete, a temperature measurement is made in step 1050 for a temperature sensing device at the port (see, for example, ports 320 or 404 in FIGS. 3 and 4) and a second temperature sensing device within the meter (see, for example, the location of temperature sensor 340 in FIG. 3). The value for the temperature measurement at the port can be referred to as $T_{PORT}$. In the embodiment illustrated in FIGS. 3 and 4, the temperature sensing device can be the thermistor 330, 460 located near the strip ports. In certain embodiments, a reading is taken from $T_{PORT}$ each time a prediction of the ambient temperature is being made for incorporation into the analyte concentration calculation.

As discussed above, at step 1060 the meter determines $T_{MICRO}$, which is an average of several temperature measurements taken from the same temperature sensor within the meter including the most recent temperature measurement made at the second temperature sensing device. At step 1070, a prediction is then made of the value of the ambient temperature using the following equation:

$$T_{AMB} = \frac{T_{Port} - K_{MP}T_{Micro}}{1 - K_{MP}} \quad \text{(Equation 2)}$$

where $T_{AMB}$=predicted ambient temperature $T_{PORT}$=temperature measured at meter port $T_{MICRO}$=average temperature measured at microcontroller $K_{MP}$=experimentally derived constant for the influence of a heat source within the meter on the temperature near the sample port After the predicted ambient temperature is determined, the logic progresses to decision step 1080 determining whether the data transfer is complete. If the data transfer is complete, then the predicted ambient temperature value, $T_{AMB}$, will be locked into the term, $T_{LOCK}$, and the time, $t_{LOCK}$, is recorded, as well. If the data transfer is not complete, the multiple sensor measurements for the temperature sensing device within the microcontroller will be reset at step 1046 to reflect the four most recent temperature measurements. Then, at step 1043, the logic process waits for a predetermined number of data packets to be transferred or for a predetermined period of time before making another prediction of ambient temperature.

The value for $K_{MP}$ used in Equation 2 is based on the temperature rise in a strip port (e.g., port 320 of FIG. 3) being proportional to the temperature rise at a source of heat within the meter. In simplified terms, it is known that the temperature at the microcontroller, $T_{MICRO}$, is equal to the ambient temperature, $T_{AMB}$, plus the temperature increase from heat generated due to activity of the microprocessor, C. It is also known that $T_{PORT}$ is equal to the ambient temperature, $T_{AMB}$, plus a proportion of the heat influence of the microprocessor or other heat-generating source on the temperature near the port. Equation 3 shows the following relationship:

$$T_{Port}=T_{AMB}+K_{MP}C \qquad \text{(Equation 3)}$$

In certain embodiments, $T_{AMB}$ is calculated every ten seconds using Equation 2. Periodic determinations of $T_{AMB}$ can be made at higher or lower frequencies than every ten seconds. When the date transfer is complete (see step 1080), the value of $T_{AMB}$ can be retained until $T_{PORT}$ decreases below a certain threshold value. In certain embodiments, the value of $T_{AMB}$ is retained until $T_{PORT}$ is less than $T_{AMB}$ plus 1.5 degrees Celsius. Following the completion of data transfer, the temperature value for $T_{PORT}$ can be periodically updated at similar frequencies as $T_{AMB}$.

It is contemplated that in certain embodiments at least two temperature sensors are used to make ambient temperature prediction while the meter is in the data transfer mode. Ambient temperature calculations can occur at regular intervals (such as every 5 seconds), throughout the data transfer mode. After the data transfer is complete, or if the data transfer unexpectedly ends, the most recent value of ambient temperature is set as $T_{LOCK}$ and the time, $t_{LOCK}$, is set to the time that the file transfer ended. The values of $T_{LOCK}$ and $t_{LOCK}$ can then be used to predict ambient temperature during a discharge state, such as, for example, illustrated in FIG. 9.

Figure 11:
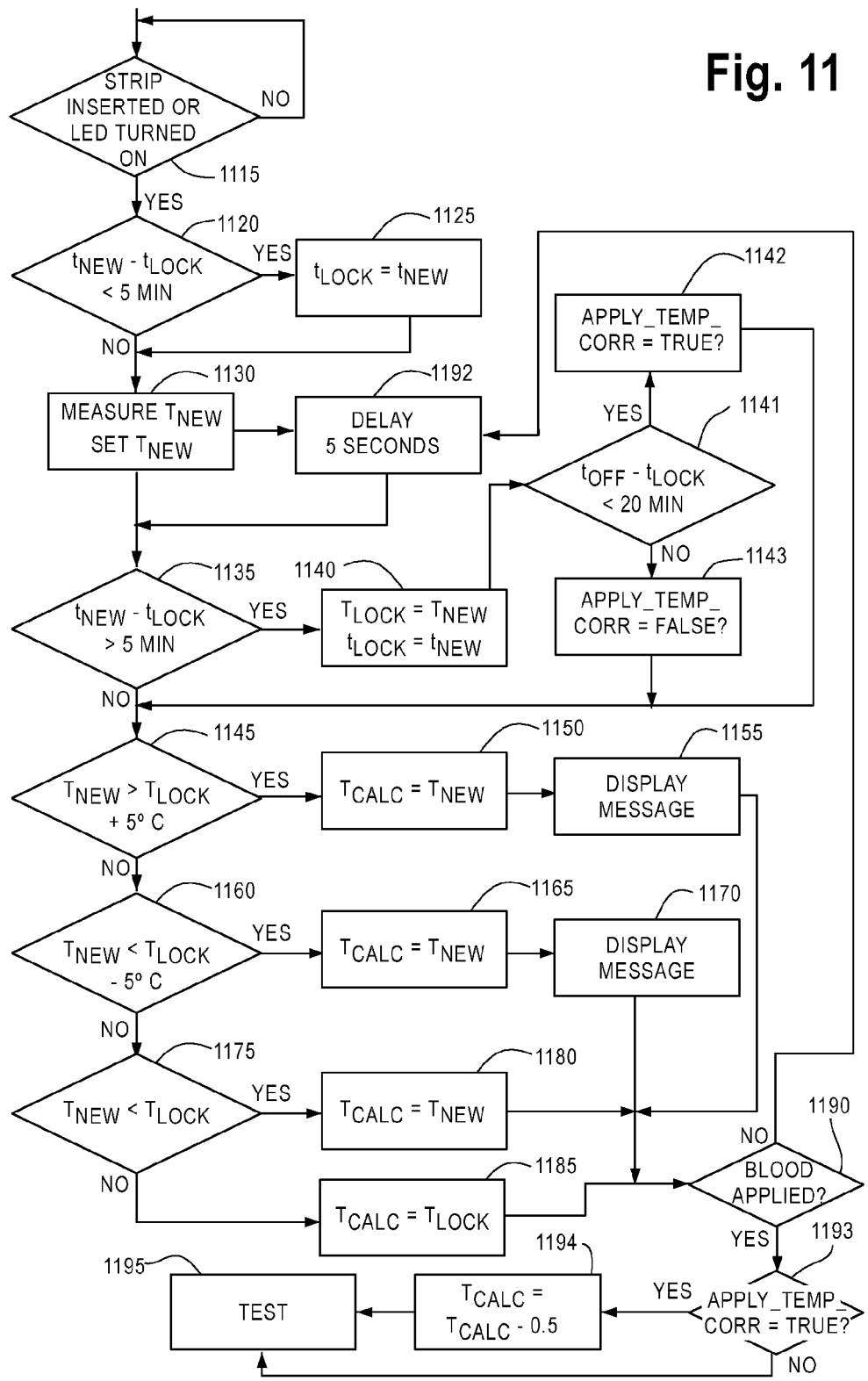
FIG. 11 illustrates a logical flow diagram of another method for predicting temperature during a battery discharge mode according to another embodiment.

Referring now to FIG. 11, a fluid analyte meter determines at step 1115 whether a certain event occurs that may generate heat within the meter. The event can include a test strip being inserted into the meter, the use of lighting associated with a test port, the use of lighting elements associated with a display, or other heat-generating events associated with a fluid analyte meter. Prior to step 1115, the meter may have recorded and stored into memory a temperature value, $T_{LOCK}$, which represents the last predicted temperature value for the meter. $T_{LOCK}$ is measured at time, $t_{LOCK}$, both of which can be recorded and stored into memory. The term, $T_{LOCK}$, is a stored temperature value that is retained and represents the current predicted value of ambient temperature to be used in determining a fluid analyte concentration, such as, for example, blood glucose concentration. $T_{LOCK}$ is also compared to subsequent temperature sensor measurements to track temperature changes and check if there has been an environmental change for the meter. The term, $t_{LOCK}$, can represent a stored time value for most the recent time that $T_{LOCK}$ (is set, and can also represent a new time value when the meter enters into a test mode within a predetermined time period after the most recent recording of $t_{LOCK}$, as illustrated, for example, in steps 1120 and 1125.

At step 1120, a determination of whether the time from $t_{LOCK}$ to the time the meter enters step 1115 is greater than or less than a predetermined period of time. In certain embodiments, if the difference between $t_{LOCK}$ and the time to step 1115 is less than five minutes, the algorithm proceeds to step 1125 and establishes a new value for $t_{LOCK}$ equal to the approximate time the meter enters step 1115. Otherwise, the value for $T_{LOCK}$ is maintained at the temperature value recorded prior to step 1115. Steps 1120 and 1125 cover the scenario where a user performs two analyte concentration tests close to each other, for example, within five minutes, and it is desired to maintain the same value for $T_{LOCK}$ in both tests. If more than a predetermined period of time lapses (for example, more than five minutes), the algorithm proceeds to step 1130 to measure a new temperature and eventually establish a new locked-in temperature. The predetermined period can vary depending on the physical properties of the meter, such as heat dissipation properties. In certain embodiments, the predetermined period will be greater than or less than five minutes.

At step 1130, the meter measures and records a new temperature value, $T_{NEW}$, which is the most recent measured temperature value. $T_{NEW}$ is recorded at time, $t_{NEW}$, and will subsequently be compared to $T_{LOCK}$. Generally, whenever a new temperature value is recorded from a temperature sensor, the time of the temperature measurement is also recorded. At step 1135, the difference between $t_{LOCK}$ and $t_{NEW}$ is determined. For the embodiment illustrated in FIG. 11, the locked temperatures are valid for five minutes, so if the difference between $t_{LOCK}$ and $t_{NEW}$ is over 5 minutes, a new lock is set by setting $T_{LOCK}$ equal to $T_{NEW}$ and $t_{LOCK}$ equal to $t_{NEW}$ in step 1140. Again, it is contemplated that different time periods both greater than or less than five minutes can be used.

The meter can also track a term, $t_{OFF}$, which retains the times at which the meter may go, for example, into an OFF state or from a menu mode to a test mode or from a reminder mode to a test mode. The menu mode, reminder mode, and test mode, represent examples of different ON states of the meter. At step 1141, a determination is made of whether $t_{OFF}$ minus $t_{LOCK}$ is less than a predetermined time period, such as, for example, twenty minutes. If $t_{OFF}$ minus $t_{LOCK}$ is less than twenty minutes, a flag, APPLY_TEMP_CORR, is set equal to TRUE at step 1142. If $t_{OFF}$ minus $t_{LOCK}$ is not less than twenty minutes, the flag, APPLY_TEMP_CORR, is set equal to FALSE at step 1143. It is contemplated that time periods greater than or less than twenty minutes can be used in step 1141.

The value of $T_{LOCK}$ and $T_{NEW}$ is now compared with upper and lower temperature thresholds to determine a predicted temperature value to be used in the determination of analyte concentration, such as blood glucose concentration, and to determine whether the ambient temperature has changed. If the difference between $t_{LOCK}$ and $t_{NEW}$ is not greater than five minutes, then the meter proceeds to step 1145 where $T_{NEW}$ is compared to an upper temperature threshold based on a predetermined temperature increase that is added to $T_{LOCK}$. If the most recent value of $T_{NEW}$ exceeds a predetermined upper temperature threshold, such as, the most recent value of $T_{LOCK}$ plus a predetermined temperature increase, the meter proceeds to step 1150 where a term $T_{CALC}$ is set equal to $T_{NEW}$. From there the meter proceeds to step 1155 where a message can be displayed to the user, such as, for example, a "READY" or a "CHANGE IN TEMPERATURE" message. If the most recent value of $T_{NEW}$ is not greater than the upper threshold, the meter proceeds from step 1145 to step 1160 where a determination is made of whether the most recent value of $T_{NEW}$ is less than a lower threshold, such as, the most recent value of $T_{LOCK}$ minus a predetermined temperature decrease. If the most recent value of $T_{NEW}$ is less than a lower temperature threshold, then the meter proceeds to step 1165 where the term $T_{CALC}$ is set equal to $T_{NEW}$. The meter can then proceed to step 1170 where a message can be displayed to the user, such as, for example, a "READY" message or a "CHANGE IN TEMPERATURE" message.

After displaying a message in steps 1155 and 1170, the meter can then proceed to step 1190 where the meter checks to see if a fluid sample, such as, for example, blood was applied to the meter. Similar to FIG. 9, the embodiment illustrated in FIG. 11 has a predetermined temperature increase and decrease of five degrees Celsius. In certain embodiments, the predetermined temperature increase or decrease can vary and can also be greater than or less than five degrees Celsius. In establishing upper and lower thresholds to apply to the decision steps 1145 and 1160, the predetermined temperature increase and decrease values can be selected to reflect a temperature change known to be due to environmental factor(s). For example, it may be known that the heat generated by a fluid analyte meter cannot increase the temperature of the device more than five degrees Celsius, and thus, when the temperature difference exceeds five degrees Celsius, the meter knows that the change in measured temperature is a change in the ambient temperature. The meter can then assign a new predicted temperature value.

At step 1175, if the most recent value of $T_{NEW}$ is less than $T_{LOCK}$, the meter will proceed to step 1180 where the term $T_{CALC}$ is set equal to $T_{NEW}$. From there the meter can proceed to step 1190 where the meter checks to see if a fluid sample, such as, for example, blood was applied to the meter. At step 1175, if the most recent value of $T_{NEW}$ is not less than $T_{LOCK}$, the meter then proceeds to step 1185 where the term $T_{CALC}$ is set equal to $T_{LOCK}$.

From step 1185, the process proceeds to step 1190 to check if a fluid sample (for example, a blood sample) was applied to the meter. If the determination is negative, the meter can proceed to step 1192, where the algorithm is set for a predetermined delay period, such as, five seconds, before proceeding back to step 1130 and going through another cycle of the algorithmic loop. If the determination is positive, the meter can proceed to step 1193 to check if the flag, APPLY_TEMP_CORR, equals TRUE or FALSE. If the flag is TRUE, $T_{CALC}$ is set equal to its most recent value minus 0.5 degrees Celsius at step 1194. If the flag is FALSE, no offset is applied to $T_{CALC}$ and the meter proceeds to step 1195 to conduct a test for fluid analyte concentration. As illustrated in steps 1141, 1142, 1143, 1193, and 1194, it is contemplated that in certain embodiments a predetermined temperature offset (for example, 0.5 degrees Celsius) can be applied to the predicted temperature, $T_{CALC}$, before the value is used to determine analyte concentration. The offset can be desirable to at least partially account for bias associated with a known quantity of temperature increase due to heat-generating elements.

In certain embodiments of step 1190, an analog engine signals a digital engine that a fluid analyte sample has been applied to the meter. For example, an analog signal can be generated from a fluid analyte sample, such as, for example, a blood sample, being placed in a port of a fluid analyte meter. The analog signal is sent to the digital engine that further processes information following receipt of the analog signal. The analog engine can also wait for the digital engine to report the most recent value for $T_{CALC}$, such as the values established at steps 1150, 1165, 1180, and 1185, before assessing whether a fluid analyte sample has been applied to the meter.

It is contemplated that in certain embodiments it would be desirable to have systems and methods for predicting ambient temperature using temperature correction values based on the length of time a meter is in a charge state, a discharge state, a data transfer states, or combinations thereof. Furthermore, various temperature thresholds or time thresholds may be established, as well, in predicting an ambient temperature value. The temperature correction values are used to account for heat generation or heat loss internal to the meter. For example, an algorithm in a meter can be implemented via a processor to evaluate temperature rise in the meter associated with heat generated during the connection of the meter to an external heat generation source such as a USB interface, mass storage elements, display elements, wireless interfaces, or other electronic components in the meter. Temperature rise may also be assessed in a meter due to the effects of the meter being connected to a charge source or a data transfer port, such as an external charge device or a USB port on a computer. Other non-limiting examples of heat sources may include a microprocessor or elements that are a part of a microprocessor such as a USB clock. In certain embodiments, it may be desirable for a USB clock to be active to receive USB interrupts. Such non-limiting examples of heat sources may be located within the meter itself or may be associated with devices with which the meter may come into contact. It is contemplated that the ambient temperature prediction embodiments described herein can be used in various fluid analyte meter embodiments including those embodiments illustrated and described in FIGS. 1-4 and elsewhere herein.

For each of the various meter states described herein (e.g., charge state, discharge state, data transfer state, combinations of states), it is contemplated that the meter will eventually reach a state of temperature stability or temperature equilibrium from which, external environmental factors aside, a determination can be made of upper and lower thresholds of temperature rise or fall. For example, in one non-limiting embodiment of the present disclosure, the concept of temperature stability was evaluated for the Contour® USB blood glucose meter by Bayer HealthCare LLC Diabetes Care of Tarrytown, N.Y., USA. In the example of Contour® USB meter, after the meter was allowed to remain in any one condition or state for approximately twenty minutes, the meter would settle on a stable temperature regardless of the power consumption or temperature rise (e.g., the meter will go from any initial condition at the point the meter is turned off to ambient in approximately twenty minutes or less). Assuming states of temperature stability in a meter can be particularly useful for making accurate calculations of fluid analyte concentration, such as the concentration of glucose in a blood sample, because such states of temperature stability can be desirable for predicting ambient temperatures to use in a fluid analyte concentration calculation. As discussed elsewhere herein, fluid analyte concentration calculations are typically prone to error due to the presence of a heat source within or near a fluid analyte meter. However, the application of various temperature states via algorithmic operations allows for the determination of correction factors that can be applied to more accurately assess an ambient temperature, and thus allow for an accurate assessment of fluid analyte concentration.

It will be recognized within the art that temperature stability applications can also be used in other temperature sensitive systems. The determination of temperature stability can be done through analysis of the heat dissipation and the heat generation properties of the system including analysis of the housing or shell material properties and heat generating elements. It will further be recognized that as these properties vary for different device configurations. For example, the Contour® USB meter described above may have different temperature stability values than another fluid analyte meter. Thus, devices of different configuration can have different times for reaching a state of temperature stability. It is therefore contemplated that in certain embodiments a meter may settle on a stable temperature in less than approximately twenty minutes or in more than approximately twenty minutes, depending on the heat generation and dissipation parameter associated with the meter.

During a charge state, a meter having a rechargeable element will generally experience a temperature rise. For example, when charging a meter such as the Contour® USB directly from a personal computer (e.g., the meter is directly connected to computer USB port), the hardware used to support the USB causes a temperature rise in the meter. Temperature rise in a meter can also occur during charging of a meter that is not USB enabled or where charging is completed with a wall charger (e.g., the meter is indirectly connected to the charger). It is contemplated that in certain embodiments, a meter such as the Contour® USB when charged directly from a USB port on a personal computer can experience a temperature rise of approximately two degrees Celsius after approximately twenty minutes of charge time. It is further contemplated that when the meter is charged through an indirect connection to the charger a temperature rise of approximately one degree Celsius will be observed after approximately twenty minutes of charge time. So, for example, when the meter is plugged into a computer or set up for charging (e.g., wall charger), the meter records the amount of time that it remains in the charge state up until the time that it is known that the meter has achieved temperature stability. In the example of the Contour® USB, an upper threshold of the amount of time that can be recorded varies including eleven minutes and twenty minutes in certain embodiments and variations thereof because at that point the temperature in the meter due to temperature rise associated with the charging is expected to have stabilized. This known upper temperature stability threshold temperature can then be subsequently used to determine the amount of temperature recovery or decrease when the meter is disconnected from the charge source (e.g., personal computer) and enters into a discharge state. The described embodiments are merely illustrative and it would be understood within the art that fluid analyte meters of having different configurations may experience similar trends of charging temperature rise and time to temperature stability, though the actual time to reach temperature stability may vary.

Figure 12:
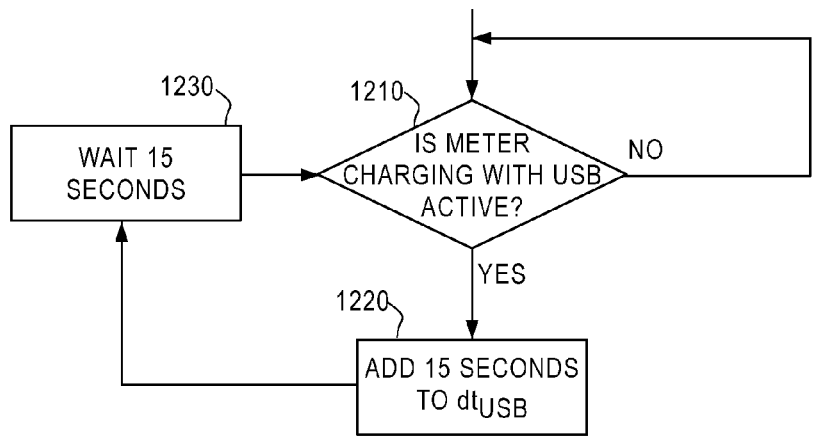
FIG. 12 illustrates a logical flow diagram of a method for monitoring USB activity time according to an embodiment.

Referring now to FIG. 12, a flowchart is illustrated for an exemplary embodiment of an method for monitoring whether the meter is in an active or charge state. At step 1210, the decision box makes a determination whether the battery in the meter is charging, or in the context of a USB-based meter, if the USB active. If the decision is no, the decision box cycles back to step 1210. If the decision is yes, at step 1220, the method adds fifteen seconds (e.g., a predetermined time interval) to a time tracking variable, $dt_{USB}$ (e.g., $\Delta t_{USB}$) which stores the length of time for which the meter is in an active state (e.g., also a charge state). The method then proceeds to step 1230 and waits for fifteen seconds (e.g., a predetermined time interval) and then cycles back to step 1210 to check again whether the meter is charging with the USB active. The cycle and wait times in FIG. 12 can be increased or decreased as appropriate for assessing a fluid-analyte concentration.

When the USB-based meter is unplugged from the personal computer or charging is stopped, the method can further include monitoring time associated with temperature recovery. A variable, $t_{OFF}$, can be used to store the time at which the meter was last turned off, or the time at which the meter goes from a menu mode to a test mode. The meter can further store a temperature value, $T_{OFF}$, which is the temperature at the time the meter is removed from the personal computer or from the charge source (e.g., turned off). When the meter is turned back on for a test or otherwise, the value of the active time of the meter (e.g., $dt_{USB}$) can be modified to reflect the amount of time that the meter has been turned off. The modification includes determining another variable, $t_{NEW}$, which represents the current time as understood by the system. In certain embodiments, the meter may use a real-time clock (RTC) with a crystal having a low power consumption introducing negligible temperature effects into the fluid analyte meter. The following relationship shows the modified determination of $dt_{USB}$ following the meter exiting the active mode and then returning after the meter is turned back on:

$$dt'_{USB} = dt_{USB} - (t_{OFF} - t_{NEW}) \quad \text{(Equation 4)}$$

where
$dt'_{USB}$=modified period of time for which a USB-based meter has been active
$dt_{USB}$=period of time for which a USB-based meter has been active prior to being turned back on
$t_{OFF}$=time at which the USB-based meter was last turned off or exited an active state
$t_{NEW}$=current time at which the USB-based meter is turned on or returned to an active state After the time for the temperature rise and/or recovery determination (e.g., $dt_{USB}$, $dt'_{USB}$), a temperature correction can be calculated using correction factors determined for an individual meter based on assessment of heat generation and heat dissipation. The relationship between time and the expected temperature correction may be generally linear. In the exemplary embodiment of the Contour® USB meter the following approximately linear relationship can be plotted based off the correction data in the following table:

TABLE 1

| Temperature Correction Values Based on USB Meter Active Time | |
|---|---|
| $dt_{USB}$ (minutes) | USB_CORR (Degrees Celsius) |
| 11 | 1.7 |
| 6 | 0.9 |
| 1 | 0.2 |

Figure 13:
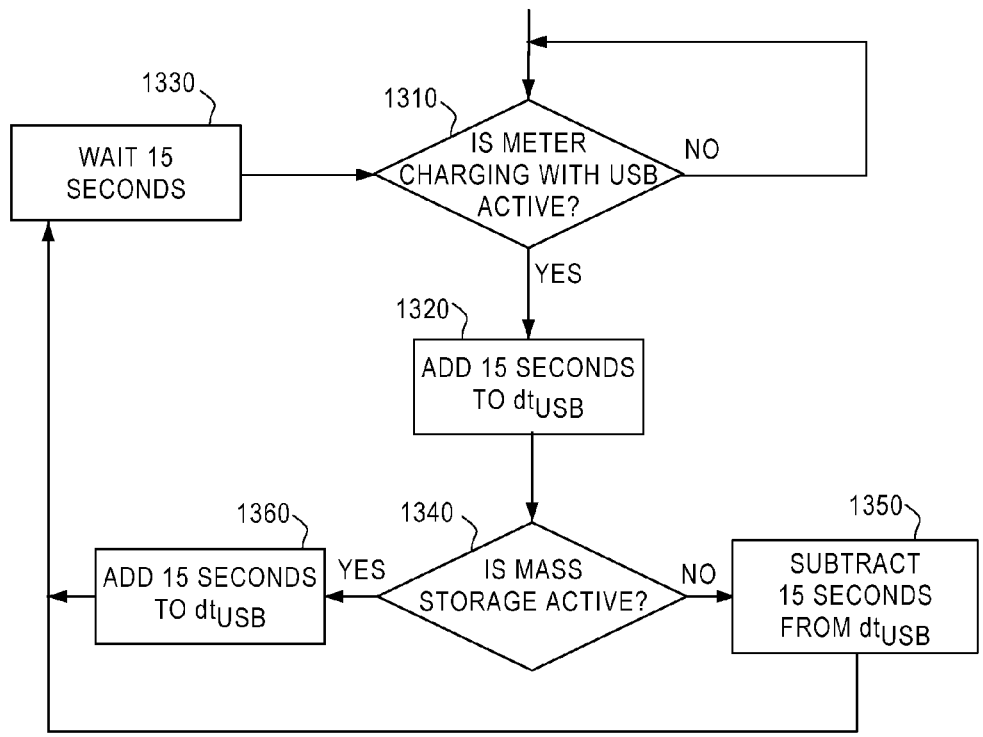
FIG. 13 illustrates a logical flow diagram of a method for monitoring mass storage activity time according to an embodiment.

Referring now to FIG. 13, another flowchart is illustrated for an exemplary embodiment of an method for monitoring whether the meter is in an active/charge state and if mass storage (e.g., data transfer) for the meter is active. The meter state of reading or writing to mass storage, similar to the charge/active state, is another point of temperature stability in a meter for which a correction factor can be determined. The mass storage state typically raises temperature concerns when a meter is active, and thus, the mass storage state is additive to the temperature rise caused by USB activity or general charge activity. Therefore, it can be handled independently, and have a separate correction factor. Similar to the USB-based activity monitoring illustrated in FIG. 12, a record for the length of Mass Storage Activity time, of up to, for example, twenty minutes is contemplated in certain embodiments. In certain embodiments, the record for the length of Mass Storage Activity time may be eleven minutes. $dt_{MS}$ (e.g., $\Delta t_{MS}$) can be updated every fifteen seconds—or otherwise as appropriate for assessing the fluid analyte concentration. At step 1310, the decision box makes a determination whether the battery in the meter is charging, or in the context of a USB-based meter, if the USB is active. If the decision is no, the decision box cycles back to step 1310. If the decision is yes, at step 1320, the method adds fifteen seconds to a time tracking variable, $dt_{USB}$, which stores the length of time for which the meter is in an active state (e.g., also a charge state). The method then proceeds to decision box 1340 to make a determination if mass storage or data transfer is active. If the decision is no, the flow proceeds to step 1350 which subtracts fifteen seconds (or otherwise) from time tracking variable, $dt_{MS}$, and then proceeds to step 1330 to wait for fifteen seconds (or otherwise) before cycling back to step 1310 to make another check of whether the meter is in a charge or active state. If the decision is yes, the flow proceeds to step 1360 which adds fifteen seconds (or otherwise) to time tracking variable, $dt_{MS}$, and then proceeds to step 1330 to wait for fifteen seconds (or otherwise) before cycling back to step 1310 to make another check of whether the meter is in a charge or active state. It will be understood in the art of the present disclosure that these concepts as illustrated for charge or mass storage activity can be applied to any significant heat-generating activity within a fluid analyte meter including, for example, display devices, wireless interfaces, or other heat-generating electrical elements.

When the USB-based meter is unplugged from the personal computer or charging is stopped, the method can further include monitoring time associated with temperature recovery from the heat generated as a result of the mass storage activity. Similar to Equation 4, a variable, $t_{OFF}$, can be used to store the time at which the meter was last turned off. When the meter is turned back on for a test or otherwise, the value of the mass storage time (e.g., $dt_{MS}$) can be modified to reflect the amount of time that the meter has been turned off The following relationship shows the modified determination of $dt_{MS}$ following the meter exiting the mass storage state (or otherwise) and the meter then being turned back on:

$$dt'_{MS}=dt_{MS}-(t_{OFF}-t_{NEW}) \quad \text{(Equation 5)}$$

where
$dt'_{MS}$=modified period of time for which mass storage has been active for a meter
$dt_{MS}$=period of time for which mass storage has been active for a meter prior to being turned back on
$t_{OFF}$=time at which the meter was last turned off or exited an active state
$t_{NEW}$=current time at which the meter is turned on or returned to an active state After the time for the temperature rise and/or recovery determination (e.g., $dt_{MS}$, $dt'_{MS}$), a temperature correction can be calculated using correction factors determined for an individual meter based on assessment of heat generation and heat dissipation due to data transfer or other heat-generating activities. Similar to the charging/active states, the relationship between time and the expected temperature correction for data transfer activities can be approximated to be linear, too. In the exemplary embodiment of the Contour® USB meter the following approximately linear relationship can be plotted based off the correction data in the following table:

TABLE 2

Temperature Correction Values
Based on USB Data Transfer Time

| $dt_{MS}$ (minutes) | MS_CORR (Degrees Celsius) |
|---|---|
| 11 | 1.9 |
| 6 | 1.0 |
| 1 | 0.2 |

As discussed previously, the temperature correction for mass storage (e.g., data transfer) activities is additive to the temperature correction for USB activity or general charging activities.

Figure 14:
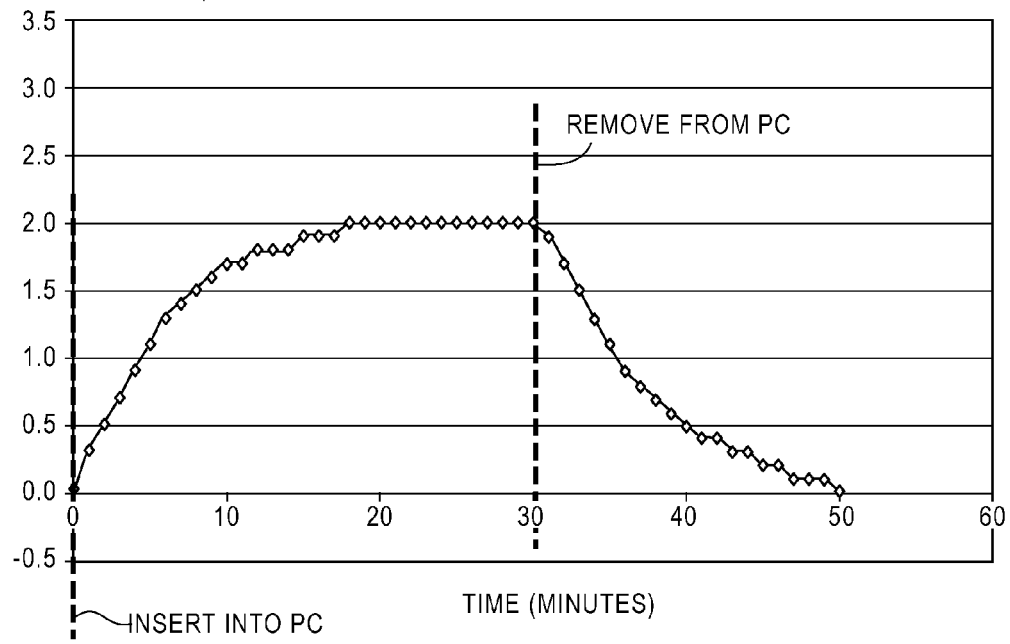
FIG. 14 illustrates temperature rise in a meter associated with USB activity according to an embodiment.

FIGS. 14 and 15 are instructive, exemplary plots of temperature rise or temperature changes observed in certain embodiments of the present disclosure, such as a device similar to the Contour® USB meter. The shapes or general trends of the plots would be expected to be generally similar for different configurations of fluid analyte devices.

FIG. 14 illustrates temperature rise or temperature influence in a USB-based meter (e.g. Contour® USB) due to USB activity from being plugged into a personal computer. Similar trends would be expected for general charging of a fluid analyte meter. The temperature stabilizes after approximately twenty minutes of activity and a two degree Celsius rise in temperature. After the USB meter is removed from the PC, the temperature again stabilizes after approximately twenty minutes back to a zero temperature rise.

Figure 15A:
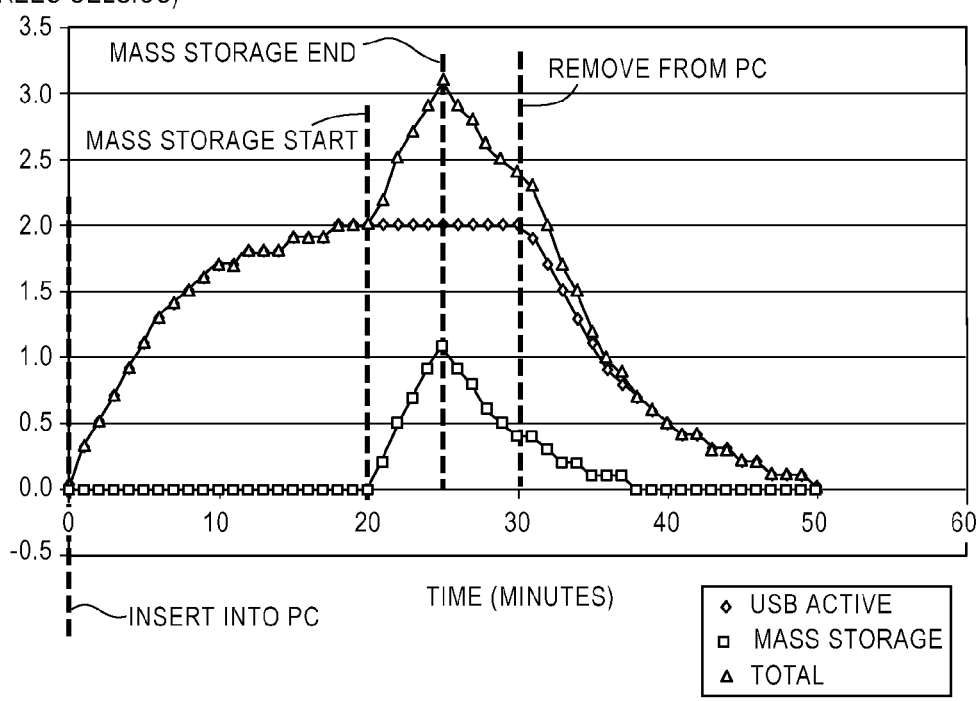
FIGS. 15a and 15b illustrates temperature rise in a meter associated with USB activity and mass storage activity, according to an embodiment.
Figure 15B:
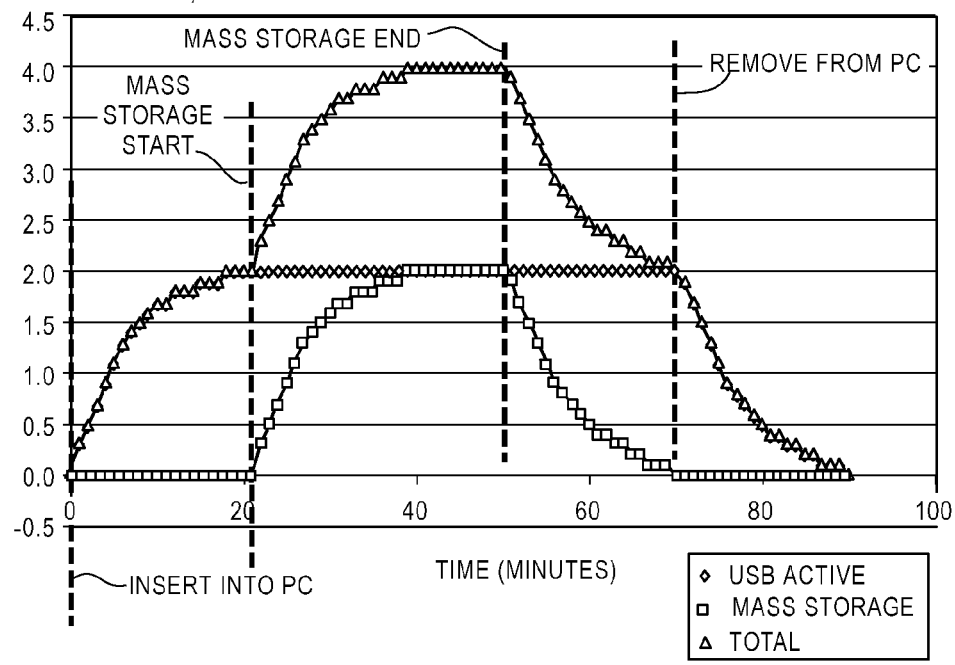

FIGS. 15a and 15b illustrate temperature influence due to both an active USB-based meter and active mass storage operations. The temperature rise for the mass storage activity in FIG. 15b is approximately double the temperature rise in FIG. 15a. It is observed from FIG. 15a that the mass storage element has an approximately linear temperature rise and recovery during the time period of the commencement of mass storage activity through the removal of the USB-based meter from the PC (e.g., between the twenty and thirty minute time periods). It is further observed that the temperature recovery from mass storage activity continues to decrease after the removal of the USB meter from the PC until the temperature rise returns back to zero. The temperature rise due to USB activity is also observed in FIG. 15a that steadily rises until temperature stability is reached after approximately twenty minutes. FIG. 15a further illustrates that temperature rise due to the mass storage activity and USB activity are additive and following the end of both the USB activity and the mass storage activity, the temperature rise in the meter returned to zero after approximately twenty minutes. Similar trends are observed in FIG. 15b, except that for longer periods of mass storage activity, the temperature rise also reaches temperature stability similar to the expected temperature rise due to USB activity.

It is contemplated that in certain embodiments it would be desirable to have system and methods for determining if a fluid analyte meter is being operated in an elevated temperature environment and for correcting for such an elevated temperature environment. For example, if the meter is configured to connect directly into a USB port on a PC, additional heat could be transferred from the PC to the meter resulting in decreased accuracy in determining a fluid analyte concentration. The male end of the USB meter may be connected to the PC for various reasons such as charging, saving personal files, backing up fluid analyte data, or running software that resides on the meter. These capabilities provide convenience to the user while also presenting a source of error if the meter is plugged directly into a PC or other device that transfers heat to the meter rather than using a USB cable. It would therefore be desirable to have a system and method that uses temperature data to assess whether a meter is being operated in an elevated temperature environment, such as the situation of a meter plugged directly into a heat source.

It is contemplated that in certain embodiments a method is implemented upon a sample strip being inserted into a meter for a determination of analyte concentration. As discussed above for the charge/active state and mass storage activity state scenarios, a temperature value, $T_{OFF}$, may be saved or stored at the end of the charge or data transfer state. Similarly, when the meter is later connected to a PC or placed into an active state, the method can correct for any temperature build-up or rise in the meter due to external heat sources, such as the PC. Furthermore, when the meter is later disconnected from the PC, a temperature correction can be applied to account for the temperature drop in the meter due to the heat source removal. In certain embodiments, it is contemplated that the rate of temperature rise is similar to the rate of temperature drop.

Figure 16:
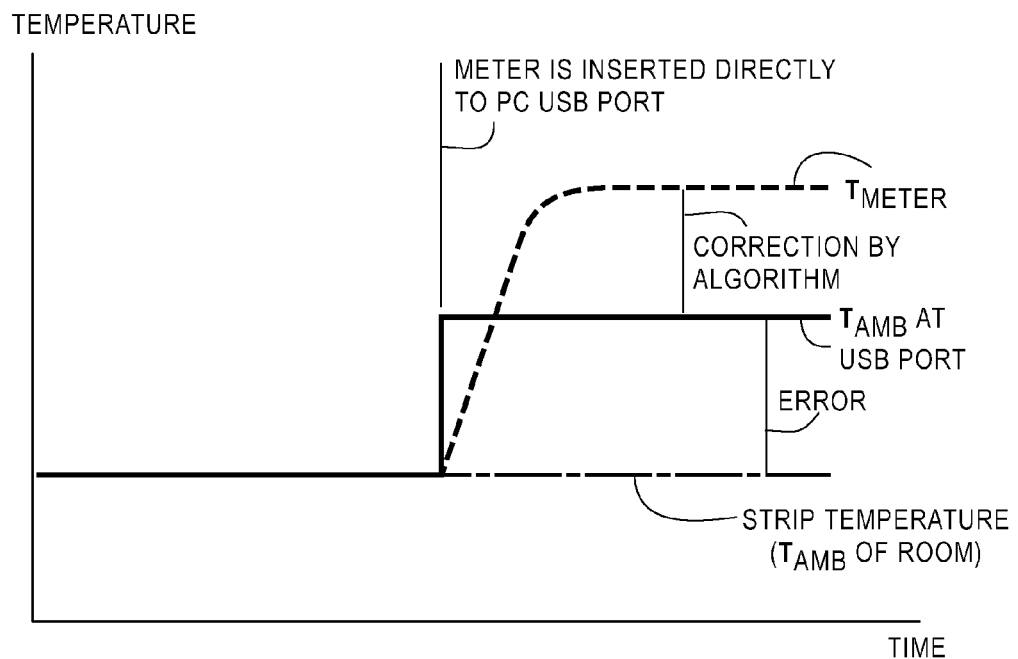
FIG. 16 illustrates temperature changes due to charging of a meter directly connected to a power source, according to an embodiment.

FIG. 16 illustrates a plot of temperature changes for a meter charged via a direct connection to a power source, such as a USB-meter plugged into a USB port on a PC. The meter temperature, $T_{METER}$, starts out initially at the same temperature as the sample strip, which is assumed to be the same as the actual ambient temperature, $T_{AMBIENT\ OF\ ROOM}$, at the location of the meter (e.g., a room). After the meter is inserted into the power source (e.g., a PC USB port), $T_{METER}$ increases due to the temperature rise associated with the heat generated in the meter from the PC and heat generated due to meter activity and/or mass storage activity. The methods illustrated above in the context of FIGS. 12-15 and elsewhere herein may not account for the heat generated in the meter associated with the PC, and thus, temperature correction using, for example Equations 4 and/or 5 can still result in error (see FIG. 16) in the prediction of ambient temperature.

Figure 17:
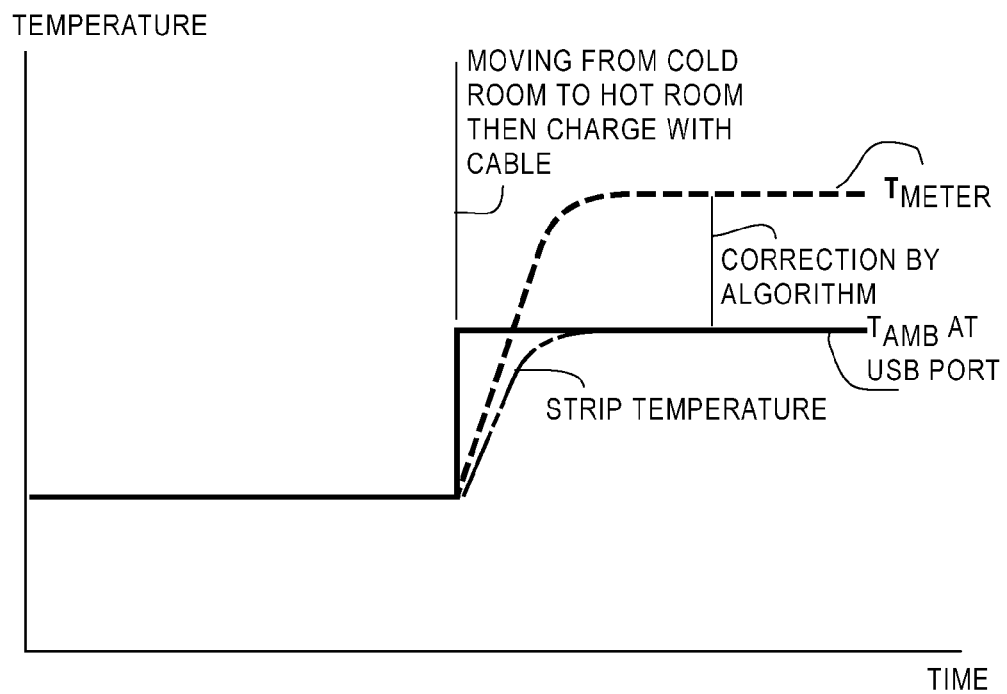
FIG. 17 illustrates temperature changes due to a change in the medium surrounding the meter followed by charging of a meter indirectly connected to a power source, according to an embodiment.

In addition, the detection of and correction for temperature rise using temperature data obtained while a USB meter is directly plugged into a USB port on a PC can be further complicated by situations that produce the same or similar effects, such as a meter user moving from a cold room to a hot room (e.g., $T_{AMBIENT\ OF\ ROOM}$ increases) and immediately switching the power source for charging the meter from a direct connection to the USB port on the computer to an indirect connection through a USB cable. FIG. 16 in view of FIG. 17 illustrates the different effects on the prediction of $T_{AMBIENT}$ in the situation where a meter is inserted directly into a PC USB port (FIG. 16) and then moving from a cold room to a warm room along with indirectly charging via a cable. While the temperature data suggests an increase in temperature due to an external heat source, temperature rise is actually due to a rise in the $T_{AMBIENT}$ of the room, and thus, should not be corrected. A method accounting for the situation of FIG. 16, but that does not account for the situation of FIG. 17, may lead to an overcorrection for the ambient temperature prediction.

Figure 18:
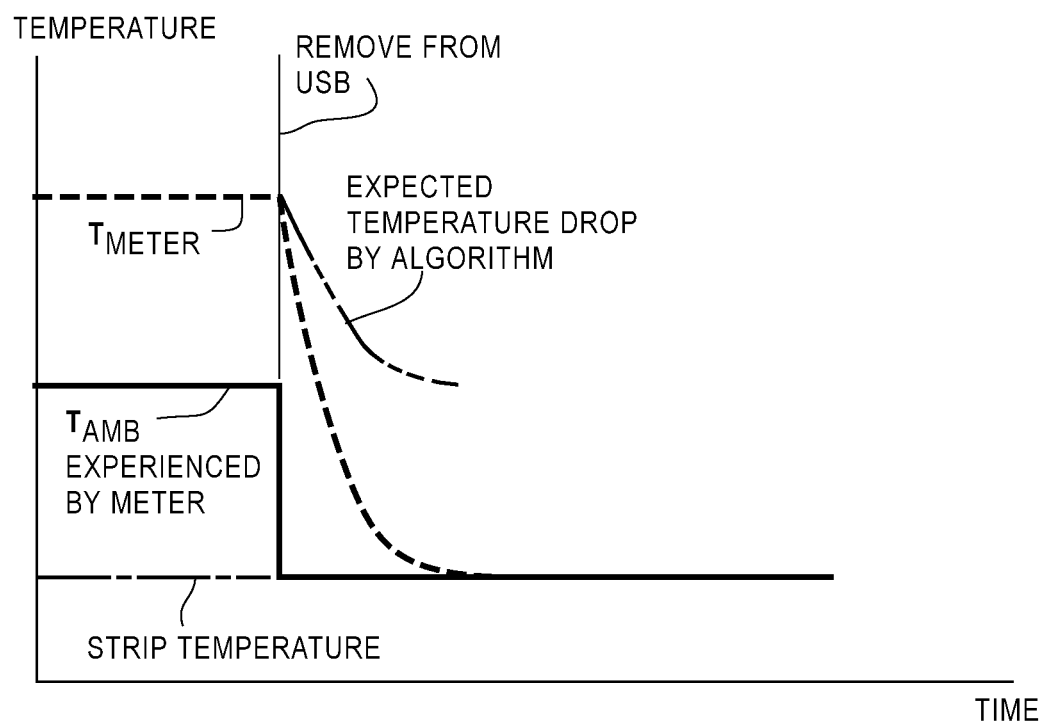
FIG. 18 illustrates temperature changes following charging of a meter directly connected to a power source according to an embodiment.

It is contemplated that it would be desirable to implement a method for assessing temperature rise due to external heat sources (e.g., PC port) through the monitoring and determining rates of temperature drop after a meter has been removed or unplugged from a direct connection to a PC. For example, FIG. 18 is a continuation of FIG. 16 and illustrates temperature drop after the meter is removed from the direct connection to a heat source (e.g., a USB port of a PC). As illustrated in FIG. 18, the actual temperature drop observed for $T_{METER}$ after the removal of the meter from the USB port is greater than the expected temperature drop that would be determined according to the algorithms illustrated elsewhere herein. Therefore, it is desirable for the method to determine the difference in the temperature drop actually experienced by the meter after removal from the direct connection to the heat source and the expected temperature drop determined by methods described elsewhere herein. The difference can be determined at the time a sample strip is inserted into the meter for assessing a fluid analyte concentration. It is contemplated that in certain embodiments a warning or suspect-concentration notice can be provided to a user of the meter depending on the magnitude of the difference and whether a calculated value of analyte concentration is prone to errors of clinical significance.

Figure 19:
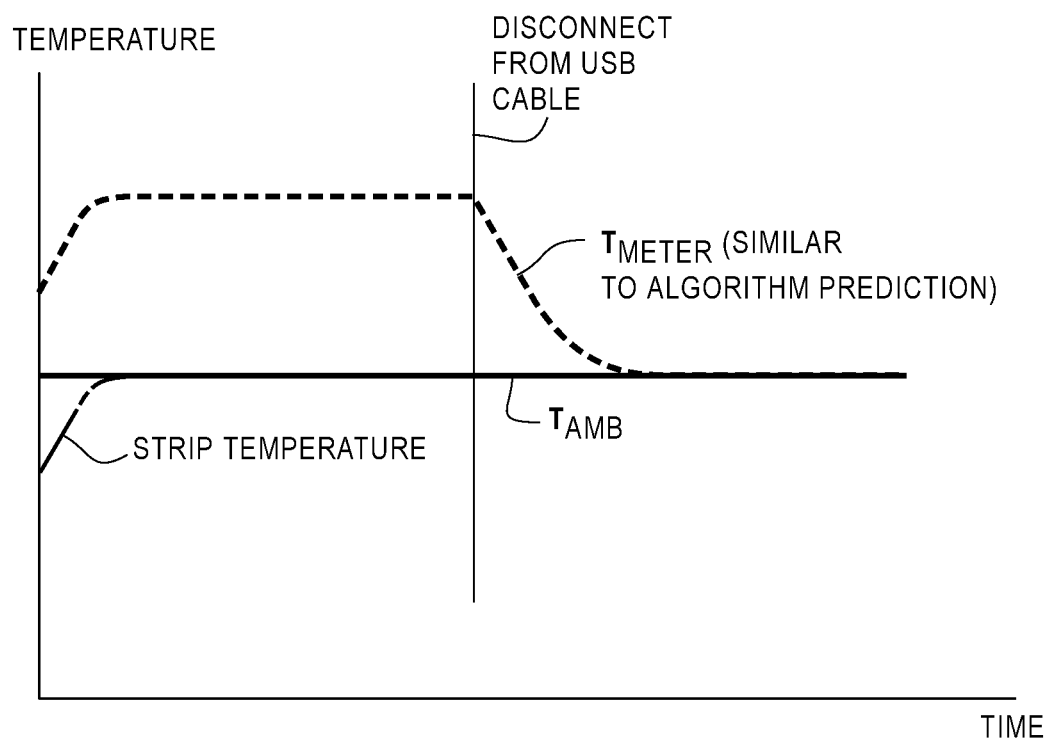
FIG. 19 illustrates temperature changes following charging of a meter indirectly connected to a power source according to an embodiment.

FIG. 19 is a continuation of FIG. 17 and illustrates temperature drop where a cable is used to indirectly connect the meter to a device such as a power source or USB port on a PC. The temperature drop for this embodiment is expected or predicted to be similar to the actual temperature observed for the meter, $T_{METER}$. That is, no error of clinical significance is expected for the scenario presented in FIG. 19 because the meter is physically separated from the heat source via the cable, and thus, unlike the scenario of FIGS. 16 and 18, the meter is not expected to experience a temperature rise due to an external heat source.

It is contemplated that a fluid analyte meter can include a processor or microcontroller for implementing an ambient temperature prediction algorithm residing in a memory associated with the meter. It is further contemplated that in certain embodiments, an ambient temperature prediction algorithm operating on a processor in the meter or otherwise can include three separate components or routines for addressing different fluid analyte meter states. The first component includes the meter discharge state or situations in which repetitive analyte concentration tests are completed. Temperature corrections associated with the first component take into account temperature rise due to meter operation other than those of the second and third components and more generally associated with normal analyte concentration testing operations (i.e., a single test) or where multiple analyte concentration tests are conducted in succession. The second component includes the meter charging state and the mass storage state and is intended to handle heat generated within the meter when, for example, the meter is charging, used for mass storage or read/write operations, or engaged in any other significant heat-producing operations (e.g., causing a temperature increase of 0.5 degrees Celsius). The third component of predicting the ambient temperature includes monitoring for heating effects caused by direct connection to a personal computer or other power source or charger. The third component includes logging events related to an analyte concentration test that is suspect or of interest. Such an event may occur, for example, for a test conducted immediately after charging.

Figure 20:
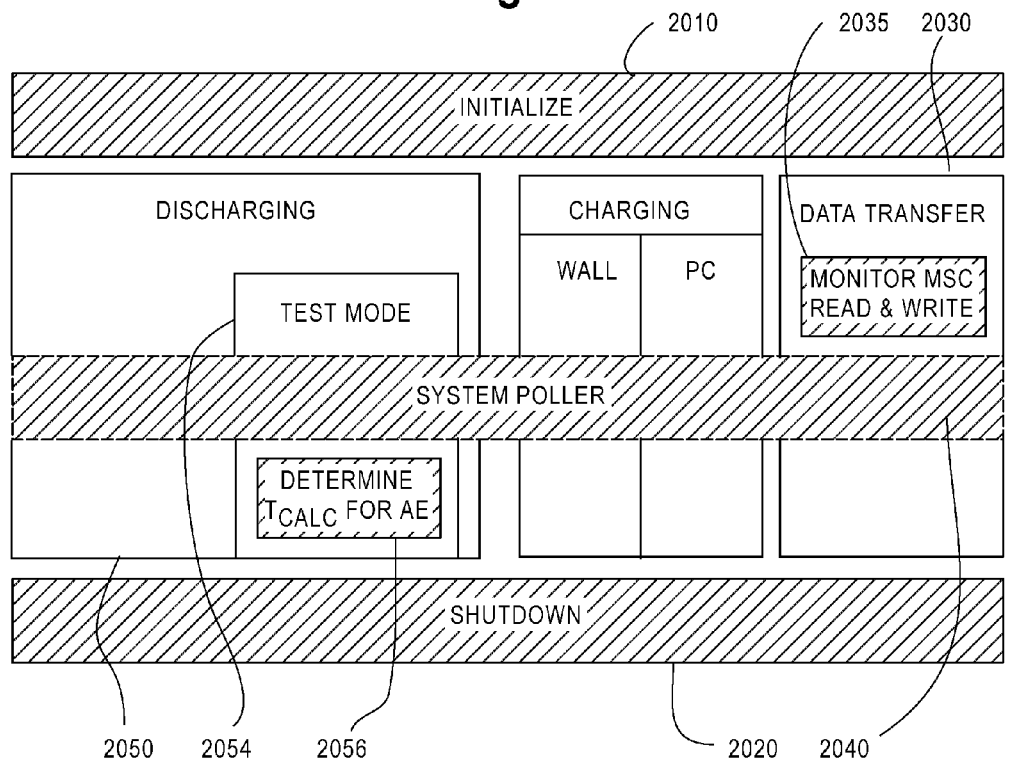
FIG. 20 illustrates various meter states for temperature prediction methods according to an embodiment.

In certain exemplary embodiments, the ambient temperature prediction algorithm is configured to be stored in a memory and/or processed on a processor such that information can be shared by the various components of the algorithm and such that the algorithm can be executed in a fluid analyte meter. FIG. 20 illustrates an exemplary architecture that may be used for the ambient temperature prediction methods for the various operational meter states described herein. An initialize routine 2010 is configured to update values, such as temperature or time values, that are stored in Electrically Erasable Programmable Read-Only Memory (EEPROM), or other forms of non-volatile memory that are known in the art, so that the values may be retrieved after the meter has been turned off or so that values may be retrieved after the meter has changed modes or states. A shutdown routine 2020 is configured to stored values related to the ambient temperature prediction algorithm in non-volatile memory (e.g., EEPROM). The shutdown routine 2020 is also configured to store any special events (e.g., suspect-value events, events of interest, etc.). Within the data transfer operations 2030, a Monitor-MSC-Read&Write routine 2035 can be configured for controlling the operations associated with reading and writing to a flash memory associated with the meter and used for mass storage including monitoring the length of time and type of mass storage operation that were performed. A system poller routine 2040 can be configured for monitoring the length of time the meter is in the charge state or the length of time mass storage operations are active. The system poller routine 2040 can also be configured to monitor temperature-related special events that may occur. A calculation temperature routine 2056 is also included for tracking meter temperature for analyte concentration testing and determining what value of temperature (i.e., predicted ambient temperature) will for used to determine analyte concentration. The calculation temperature routine 2056 can reside within a test mode application 2054, which may be a part of the discharge applications 2050 associated with the ambient temperature prediction algorithm. It is contemplated that the calculation temperature, $T_{CALC}$, may be determined using a digital engine associated with the fluid analyte meter. The value of $T_{CALC}$ may, however, be provided to an analog engine that is responsible for determining an analyte concentration (e.g., a blood glucose measurement).

It is contemplated that in certain embodiments, a first component of an ambient temperature prediction method includes processes for handling a meter discharge state or situations in which repetitive analyte concentration tests are completed. Therefore, one purpose of the first component can be to address temperature rise internal to the meter during the discharge state. This may be done by applying a correction to the temperature value used in analyte (e.g., blood glucose) concentration calculation based on whether the meter was recently operated. In certain embodiments, the influence of heat generated by operations internal to the meter can add approximately a zero to one degree Celsius temperature bias into the meter during the charge and discharge states. It may therefore be desirable in certain embodiments to apply an offset when the meter has recently been in use to balance the bias so that it is ±0.5 degrees Celsius. Thus, a 0.5 degree Celsius correction can be used when the meter was operated within a certain period of time, such as the length of time it takes a meter to reach temperature stability. In certain embodiments, the correction may be applied if the meter was operated in the last twenty minutes. It is further contemplated that the correction value can be higher or lower than ±0.5 degrees Celsius and should be based on the individual temperature rise characteristics of a given fluid analyte meter.

A second purpose of the first component is to maintain consistency between multiple subsequent analyte concentration tests. It may therefore be desirable to lock in a temperature value for a predetermined period of time on the assumption that analyte concentration tests that occur within a predetermined period of time occur in the same or similar environment. In certain embodiments, a temperature value may be locked in for five minutes. However, in addition to locking in a temperature value, it is also contemplated that the method continues to monitor temperature and may further respond as the latest temperature reading varies from the locked temperature.

Figure 22A:
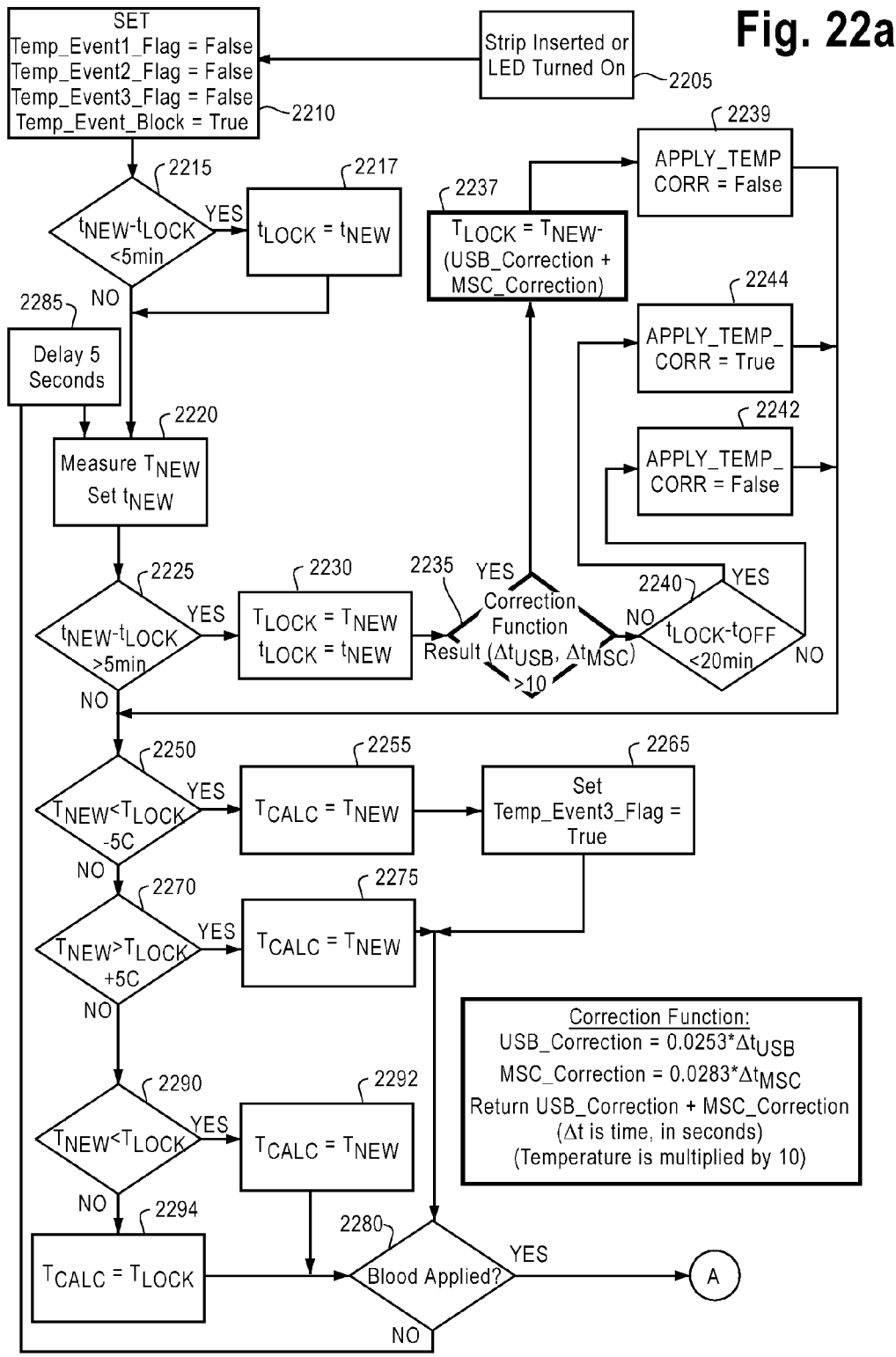
FIGS. 22a and 22b illustrate a logical flow diagram of a method for predicting temperature during a test mode according to an embodiment.

Turning now to FIG. 22a, a detailed flow diagram provides additional detail of certain embodiments for predicting ambient temperature in a fluid analyte meter. At step 2205, the ambient temperature prediction algorithm may start when a user first indicates that they want to perform an analyte concentration test (e.g., a blood glucose test). For example, a user may insert a sample strip into a meter, provide some type of user input, or turn on a strip port LED so that the strip may be inserted in the dark. At step 2210, several logic operators associated with various temperature events can be set to false and then at step 2215, an assessment is made of whether the last temperature lock, $t_{LOCK}$, occurred within five minutes, or some other predetermined interval, of the time that the algorithm started. The term, $t_{LOCK}$, can be defined as a stored time value that is retained through resets, which marks the most recent time that $T_{LOCK}$ has been set and is useful for timing in the diagram. The term, $T_{LOCK}$, can be defined as a temperature value, measured when the meter is on, but stored and retained through resets to determine a temperature for analyte concentration measurements and also track temperature changes to see if there has been an environmental change. If a period longer than the predetermined interval has lapsed, value of $t_{LOCK}$ can be reset at step 2217 to the present time, and effectively re-lock in the current value of $T_{LOCK}$ for the next five minutes. Thus, in the case where a user performs multiple tests close to each other, the same $T_{LOCK}$ value can be applied to both tests. If more than five minutes or some other predetermined time interval have lapsed, then at step 2220 the current temperature, $T_{NEW}$ is recorded along with the time, $t_{NEW}$, at which, $T_{NEW}$ was recorded. The term, $t_{NEW}$, can be defined as a time value that marks when $T_{NEW}$ was recorded and the term, $T_{NEW}$, can be defined as the most recent temperature value taken that will be compared to $T_{LOCK}$. Next, at step 2225, another assessment can be made of the difference between $t_{NEW}$ and $t_{LOCK}$. If the difference exceeds a predetermined time interval (e.g., five minutes), then the flow diagram proceeds to step 2230 where $T_{LOCK}$ is set equal to the latest temperature value, $T_{NEW}$, as recorded by a temperature sensor and $t_{LOCK}$ is set equal to the time, $t_{NEW}$, which is the time at which the latest temperature value, $T_{NEW}$, was recorded. Whenever a new temperature measurement is made, the time of the temperature measurement is also recorded. Next, at step 2235, the logic diagram assesses whether a correction function result exceeds a value of ten, the value representing a temperature value of one degree Celsius because of temperature being multiplied by 10 (see, e.g., Correction Function box in FIG. 22a). The Correction Function box includes equations for the USB_Correction and MSC_Correction that include correction factors of 0.0253 and 0.0283, respectively, which were determined for an exemplary embodiment. Such correction factors could be determined for other embodiments using the methods disclosed elsewhere herein. If the correction function exceeds ten (i.e., one degree Celsius), then at step 2237 $T_{LOCK}$ is set equal to $T_{NEW}$ minus the quantity established by the USB correction function (USB_Correction) plus the mass storage correction function (MSC_Correction), which are based on time tracking variables that each respectively track the length of time of charge, $\Delta t_{USB}$, and the length of time of data transfer, $\Delta t_{MSC}$. The term, $\Delta t_{USB}$, can be defined as a timer that monitors the length of time of charge or a period of time that is saved, through resets, and stores a length of time for which USB or meter has been active. The term, $\Delta t_{MSC}$, can be defined as a timer that monitors the length of time of data transfer or a period of time that is preserved through resets and holds the length of time for which Mass Storage has been active. Correction factors are also applied to $\Delta t_{USB}$ and $\Delta t_{MSC}$ that are specifically developed using meter specific data such as the exemplary data in Tables 1 and 2 or FIGS. 14-15. The flow diagram then proceeds to step 2239 where the logical operator, Apply_Temp_Corr is set equal to false. If the correction function does not exceed 10, then at step 2240, as assessment of the difference between $t_{LOCK}$ and $t_{OFF}$ is made and if the difference is less than twenty minutes, then at step 2244, the Apply_Temp_Corr operator is set to true. The term, $t_{OFF}$, can be defined as the time at which the meter was last turned off. Otherwise, the Apply_Temp_Corr logic operator is set to False. The Apply_Temp_Corr logic operator in steps 2239, 2242, 2244 are then later evaluated to determine if the temperature correction is to be applied (i.e., true) or not be applied (i.e., false).

Figure 21:
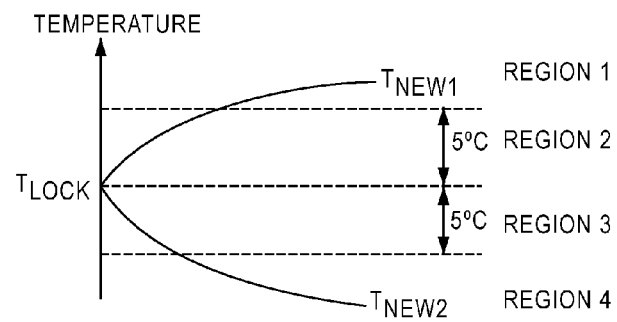
FIG. 21 illustrates temperature thresholds for predicting ambient temperature according to an embodiment.

Next, the flow diagram then proceeds to step 2250 where in a series of steps the values of $T_{LOCK}$ and $T_{NEW}$ are compared along with upper and lower thresholds to determine which value is to be use in the analyte concentration calculation and to further determine if ambient temperature has changed. FIG. 21 provides a graphical illustration of how $T_{LOCK}$ and $T_{NEW}$ are processed to determine $T_{CALC}$, the predicted ambient temperature for use in the analyte concentration calculation. If the value of $T_{NEW}$ is greater than $T_{LOCK}$ plus five degrees Celsius, this is likely due to a change in environmental temperature. The heat generated within the meter cannot generally increase the meter temperature by more than five degrees Celsius under normal operating conditions. When this threshold is breached (see step 2270 and Region 1), $T_{CALC}$ is set to be $T_{NEW}$ (see step 2275) because $T_{NEW}$ will most likely be closer to ambient temperature. In Region 2, the temperature value for $T_{NEW}$ is greater than or equal to $T_{LOCK}$, but does not breach the upper threshold (see step 2290). This can be considered an expected amount of temperature rise, and $T_{LOCK}$ is the closest to ambient. Thus, for situations in Region 2, $T_{CALC}$ is set to be equal to $T_{LOCK}$. (see step 2294). In Region 3, the temperature value of $T_{NEW}$ is less than $T_{LOCK}$ (see step 2290). Heat generated internally to the meter is expected to increase the temperature measured relative to the ambient temperature, so a measured temperature below $T_{LOCK}$ indicates a change in meter environment. Thus, the temperature value of $T_{NEW}$ is closer to true ambient, so $T_{CALC}$ is set to be equal to $T_{NEW}$ (see step 2292). Finally, in Region 4, the temperature value of $T_{NEW}$ is less than $T_{LOCK}$ minus five degrees Celsius (see step 2250), which would be expected to be caused by an environmental change. Therefore, $T_{CALC}$ is set to be $T_{NEW}$ (see step 2255). Additionally, the Temp_Event3_Flag (e.g., a special event not necessarily warranting an error that relates to temperature) at step 2265 is set to true. Event operators such as the Temp_Event3_Flag operator at step 2265 will be explained in greater detail in the discussion of FIG. 24.

Next, the flow diagram proceeds to step 2280 where an assessment is made of whether a fluid (e.g., blood) has been applied and/or a test strip has been inserted into the meter. If the answer is no, the flow diagram proceeds to step 2285 where there is a delay of a predetermined duration (e.g., 5 seconds) before the flow diagram cycles. If a fluid is applied or a sample strip has been inserted into the meter, the analog engine signals the digital engine of this occurrence and then the analog engine waits for the digital engine to return the value of $T_{CALC}$ to use in calculating analyte concentration.

Figure 22B:
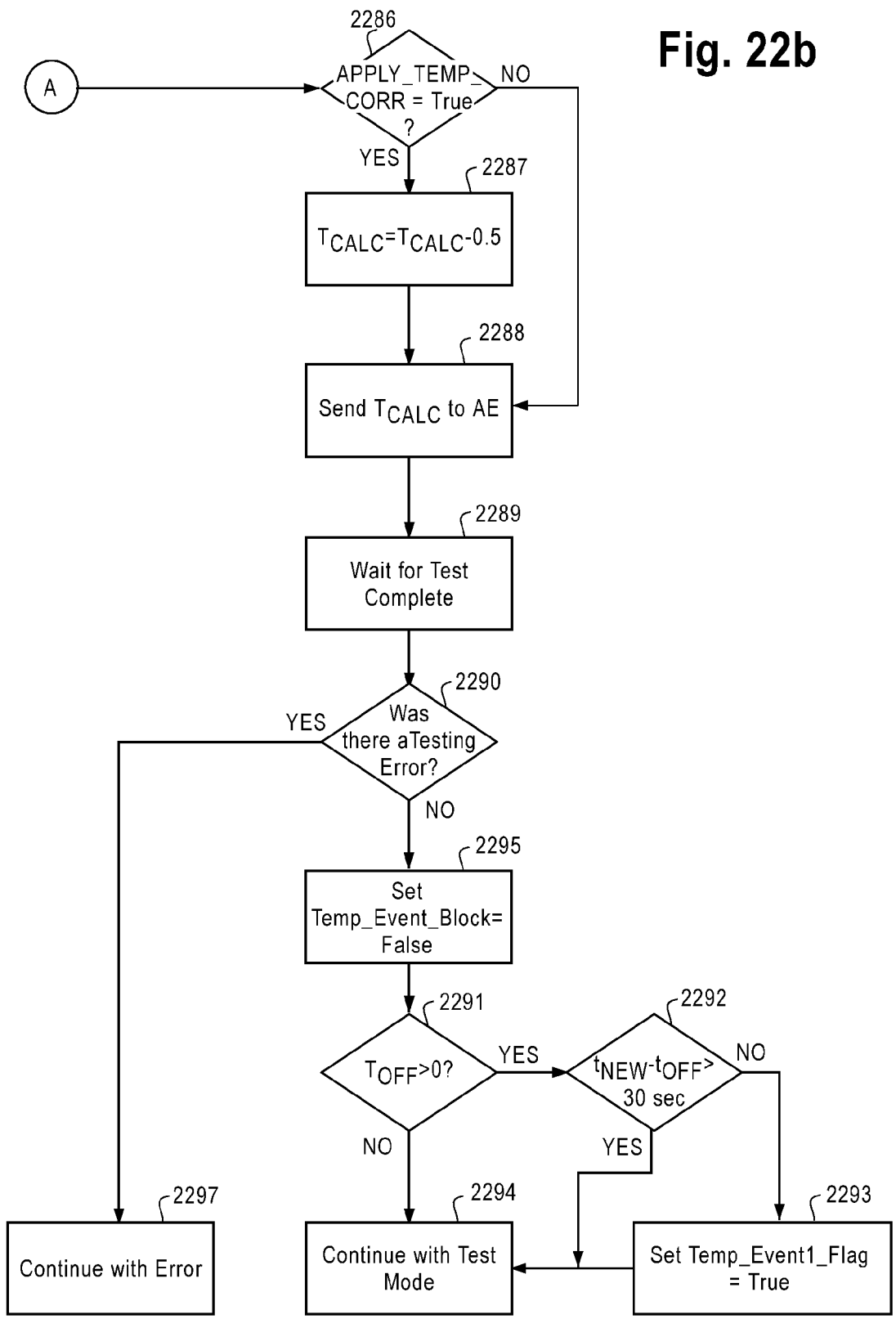

Referring now to FIG. 22b, if the Apply_Temp_Corr operator was set to True (see step 2286) at step 2244, then $T_{CALC}$ is adjusted with a 0.5 degree Celsius offset (or as otherwise determined for a given meter) at step 2287. However, if the Apply_Temp_Corr operator was set to False at step 2239 or 2242, then $T_{CALC}$ is sent to the analog engine for the determination of analyte concentration using $T_{CALC}$.

It is contemplated that in certain embodiments, a second component of a method for predicting ambient temperature includes processes for correcting temperature due to charge state activities and mass storage or data transfer activities of a meter. In certain embodiments, a meter may be charged through direct connection to a PC such as via a USB port for which a temperature correction can at least partially be made using the second component. In other embodiments, a meter may be charged through an indirect connection to a charging device and in such scenarios, the first component of the ambient temperature prediction method provides an acceptable temperature correction.

The second component for correcting temperature and predicting ambient temperature in a fluid analyte meter includes a separate assessment of the temperature rise associated with the direct connection to the PC and related charging, and the temperature rise associated with the mass storage or data transfer activities. In certain embodiments described herein, it is desirable to use separate timers for tracking connection time to the PC and mass storage time. The timers can be regulated by the system poller 2040 (see, e.g., FIGS. 20 and 23), and may be incremented using time tracking variables, $\Delta t_{USB}$ and $\Delta t_{MSC}$, which may be incremented at a predetermined interval (e.g., fifteen seconds or otherwise) similar to the exemplary embodiments illustrated in FIGS. 12 and 13. The timers can also include maximum or threshold values that adjust as the timer is incremented or decremented over the predetermined time interval. For example to compensate for the temperature drop observed when battery charging is complete, the maximum allowed value changes. In this case, the value of $\Delta t_{USB}$ will be decremented every fifteen seconds (e.g., predetermined time interval), until it reaches a modified, lower maximum. The purpose of adjusting or modifying the maximum or threshold values is to account for temperature changes during the various phases of the charge cycle.

Figure 23A:
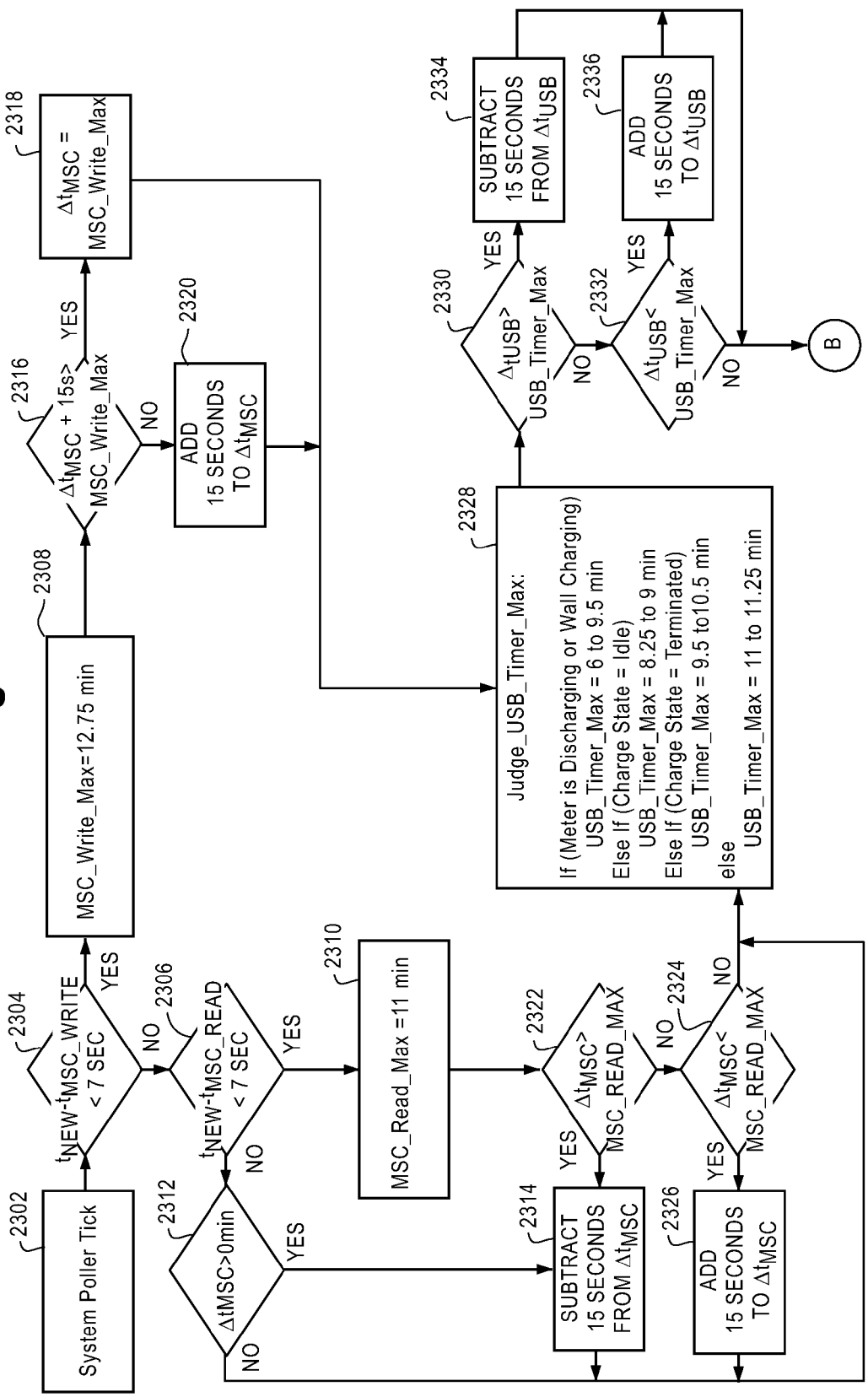
FIGS. 23a and 23b illustrate a logical flow diagram of a method for monitoring time for certain temperature-related operations according to an embodiment.

Reading and writing to and from mass storage of the meter can operate within the system poller. Referring now to FIG. 23a, an exemplary embodiment for the second component of the algorithm begins with a system poller tick 2302 followed by assessing at steps 2304 and 2306 whether the difference between the current time, $t_{NEW}$, and the time for a mass storage write, $t_{MSC\_WRITE}$, or mass storage read, $t_{MSC\_READ}$, is less than seven seconds (or another predetermined time interval). The time for reading from and writing to mass storage is stored in $\Delta t_{MSC}$. The mass storage timer maximum is based on whether the meter recently performed a read or write operation. If the operation occurred within seven seconds prior to the system poller 2040 running, the timer will be moved towards the appropriate maximum at either steps 2308 or 2310. If no data transfer operation is detected at steps 2304 or 2306, the flow diagram proceeds to step 2312 where a check is made whether the timer is greater than zero. If the answer is yes, the time tracking variable, $\Delta t_{MSC}$, is decreased by a predetermined time increment (e.g., fifteen seconds) at step 2314. At steps 2308 and 2310, maximum or threshold times are established which the time tracking variable, $\Delta t_{MSC}$, is not allowed to exceed. The maximum or threshold values are predetermined for a meter based on the meter's heat generation and dissipation properties. Following step 2308, the flow proceeds to step 2316 where it is determined if $\Delta t_{MSC}$ plus a predetermined time interval (e.g., fifteen seconds) exceeds the mass storage write maximum threshold established in step 2308. If it does, $\Delta t_{MSC}$ can be reset to be equal to the write maximum threshold (e.g., MSC_Write_Max) at step 2318. Otherwise, at step 2320, $\Delta t_{MSC}$ is increased by a predetermined time increment (e.g., fifteen seconds). Following step 2310, the flow proceeds to steps 2322 and 2324 where it is determined if $\Delta t_{MSC}$ is greater than or less than the mass storage read maximum threshold established in step 2310. If greater, $\Delta t_{MSC}$ is decreased by a predetermined time increment (e.g., fifteen seconds) at step 2314. Otherwise, at step 2326 $\Delta t_{MS}$ is increased by a predetermined time increment (e.g., fifteen seconds).

Next the flow in FIG. 23a proceeds to step 2328 where threshold or maximum values for the charging timer, $\Delta t_{USB}$, are established based on the charge state that the meter battery may be in that includes discharging or wall charging (e.g., cable connection) and the various phases of a battery charge cycle such as idle, terminated, or fast charging. For certain embodiments, the threshold or maximum value falls within the range of maximum values identified in step 2328. The flow diagram then proceeds to steps 2330 and 2332 where it is determined if $\Delta t_{USB}$ is greater than or less than the charge timer maximum established in step 2328. If it does, $\Delta t_{USB}$ has a predetermined time increment (e.g., eleven seconds, fifteen seconds, or otherwise) subtracted from it at step 2334. Otherwise, at step 2336 $\Delta t_{USB}$ is increased by a predetermined time increment (e.g., fifteen seconds). If neither result from step 2330 or 2332 is true, then the method proceeds to FIG. 23b.

It is contemplated that the value of $\Delta t_{USB}$ can be used to monitor temperature rise during charging and can also remain active while the meter is in the discharge state. Thus, the corrections for temperature behavior of the meter in use situations where the meter is operated immediately before or immediately after charging can be accounted for.

As discussed elsewhere herein, whenever the meter is turned on the length of time the meter was off is calculated. This length of time is then subtracted from the time at which the meter was turned on to account for any cooling in the meter while it is off. It is contemplated that the timer or time tracking variables are not allowed to have a value less than zero.

Figure 23B:
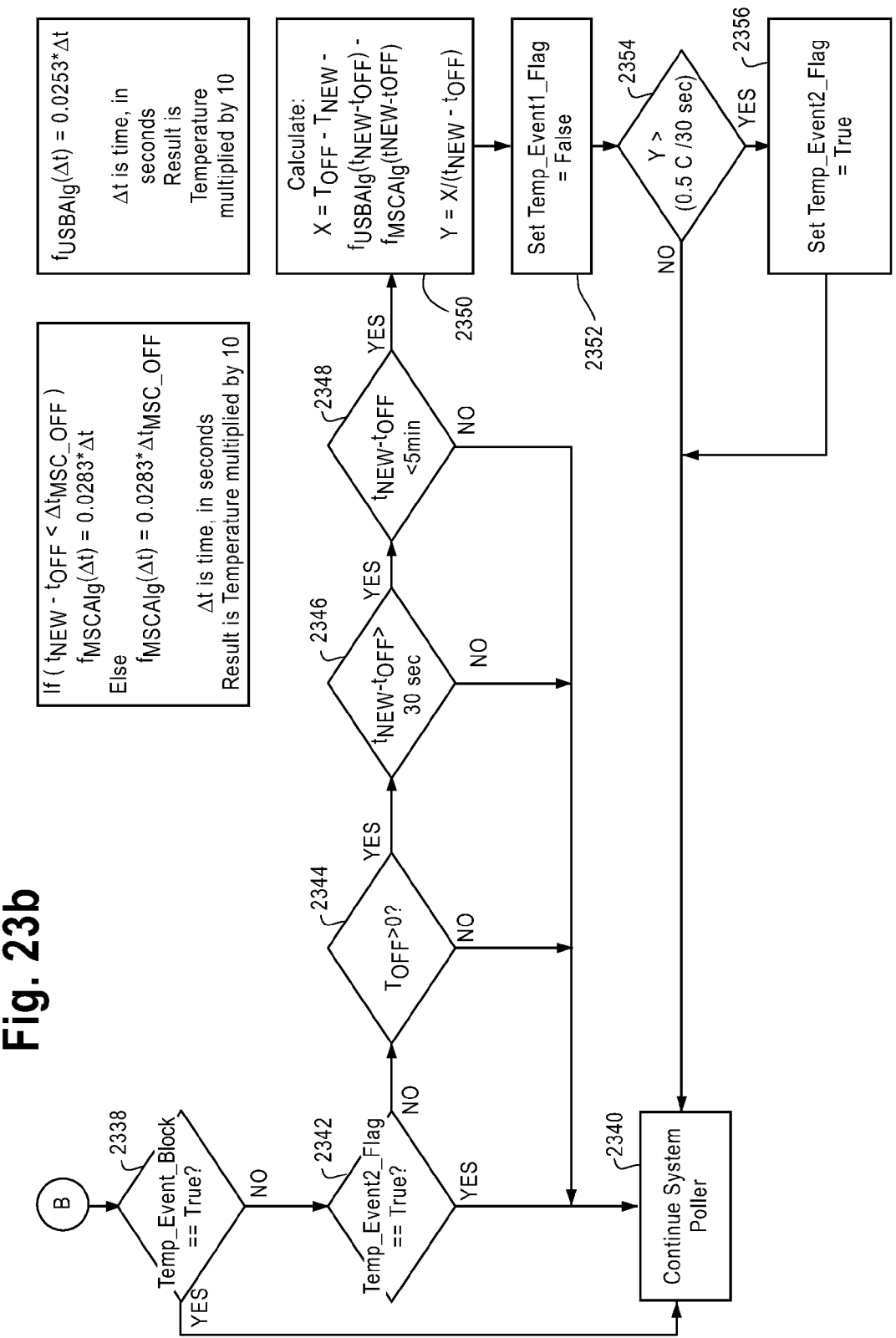

Referring now to FIG. 23b, the flow continues from FIG. 23a to step 2338 where the meter can assess if the Temp_Event_Block logical operator is set to true. If yes, the meter flow proceeds to step 2340, which continues the system poller operation. If no temperature event block is present, the method proceeds to step 2342 to assess whether an event, Temp_Event2, has occurred or whether the flag has been set to true (see step 2356). If Temp_Event2 is true, then the method proceeds to the system poller at step 2340 because an attempt is being made to conduct the test during a period when the meter has detected that it was directly connected to a PC or other charging device which contributes a significant temperature difference relative to the room in which the test has been performed. If Temp_Event2 is not true, then the method proceeds to step 2344 to check if $T_{OFF}$, the temperature value at which the meter was last turned off, is greater than zero. The term, $T_{OFF}$, can also be defined as a stored temperature value that is saved when the meter is removed from a PC or wall charger or as a reference temperature, measured before the meter is turned off at the end of charging, but stored and retained to estimate whether there has been an environmental change. If $T_{OFF}$ is not greater than zero, the method proceeds to step 2340. If $T_{OFF}$ is greater than zero the method proceeds to steps 2346 and 2348 to determine if the meter was turned off for more than thirty seconds but less than five minutes (e.g. within a predetermined time period or range). In certain embodiments, the range may be thirty seconds to twenty minutes. As discussed elsewhere herein, such values or ranges of values are exemplary only for purposes of illustrating non-limiting embodiments of the disclosed ambient temperature prediction methods. If the meter was not turned off within the predetermined time period, then the method proceeds from step 2346 or 2348 to the system poller at step 2340.

In the exemplary embodiment of a USB meter, which is equipped with a male USB connector, a meter can be connected to a PC for the purpose of charging, saving personal files, backing up blood glucose data, or running software that resides on the meter. If the user plugs the meter directly into a PC or other device that transfers heat to the meter, some error may be introduced in calculating analyte concentrations. In the absence of being able to detect how the connection is made by some electrical signal, a method detects these situations by monitoring and applying temperature data.

The third component of the ambient temperature prediction algorithm implements a method for monitoring temperature drop after the meter has been charged. After a meter is removed or disconnected from a charging element, a temperature value, $T_{OFF}$, is stored which serves as the reference, end-of-charging temperature. The associated timing reference, $t_{OFF}$, is set at the moment that the meter is removed or disconnected from the charging source (e.g., unplugged from the PC). The time, $t_{OFF}$, can be stored as a real-time clock value or stored as a reference time zero from which the time after the meter has been unplugged from the PC is tracked.

At step 2346, a determination is made on whether the meter was turned off for more than thirty seconds (e.g., more than a predetermined time). In certain embodiments, the time period from $t_{OFF}$ to $t_{OFF}$ plus a predetermined interval of time (e.g., thirty seconds or otherwise depending on the meter configuration) and a direct connection to a PC or other direct charging device can be difficult to detect using temperature data. Once the meter has had the opportunity to measurably cool there can be confidence that a temperature drop was due to a removal or disconnection from the PC or direct charging device. Returning to FIG. 22b, at step 2289, a user waits for an analyte concentration test to be completed. Next, the flow diagram proceeds to step 2290 to determine if there were any testing errors. If there were no errors, the method first proceeds to step 2295 to set Temp_Event_Block to false and then proceeds to step 2291 to determine if $T_{OFF}$ is greater than zero, similar to step 2344 in FIG. 23b. If $T_{OFF}$ is greater than zero then the meter proceeds to check if a result was obtained within thirty seconds of the meter being unplugged from the PC at step 2292. If the result was obtained within such time period, the Temp_Event1 flag is set to True at step 2293 and the occurrence of the event (e.g., a special event or a suspect-value event) may be stored immediately or at a later time in a log that associates the event with the time it occurred. The method then proceeds to continue with the test mode at step 2294. If a testing error results at step 2290, then the method continues with an error at step 2297.

Referring back to steps 2346 and 2348 of FIGS. 23b, a determination is made on whether the meter was turned off for a predetermined time interval (e.g., more than thirty second but less than five minutes). Within the predetermined time interval, a meter can be configured to detect a direct connection to a PC based on the monitoring of temperature data. It is contemplated that in certain embodiments, the meter will make a periodic direct connection determination (e.g., every 15 seconds or at other preselected time intervals) from the system poller task if both of the following conditions are true: (i) the meter is in test mode, and the current time falls within $t_{OFF}$ plus a preselected range determined according to the heat dissipation properties of the fluid analyte meter (e.g., $t_{OFF}$ plus thirty seconds to five minutes for the Contour® USB meter). The determination of a direct connection to a PC or other charging source can be made using the following equations, which are also illustrated in steps 2350 and 2354, that estimate the temperature:

$$X=T_{OFF}-T_{NEW}-f_{USBAlg}(t_{NEW}-t_{OFF})-f_{MSCAlg}(t_{NEW}-t_{OFF})$$ (Equation 6)

$$Y=X/(t_{NEW}-t_{OFF})$$ (Equation 7)

where
X=difference between the actual temperature drop and the expected temperature drop;
Y=rate of change of the difference between actual and experienced temperature drops;
$f_{USBAlg}(t)$=correction value or factor of the ambient temperature prediction algorithm for charging where $\Delta t_{USB}=(t_{NEW}-t_{OFF})$; and
$f_{MSCAlg}(t)$=correction value or factor of the ambient temperature prediction algorithm for mass storage where $\Delta t_{MSC}=(t_{NEW}-t_{OFF})$.

Referring back to FIGS. 18 and 19, Equations 6 and 7 relate to the comparison of observed temperature drop and expected temperature drop and determining if the rates of change are similar. In the exemplary embodiment of FIG. 23b, the term X is calculated at step 2350 and Temp_Event1 Is set to False in step 2352. At step 2354, the rate of change of the difference between actual and observed temperature drop (e.g., Y) is made. For an exemplary meter (e.g., Contour® USB), X is determined to be 0.5 degrees Celsius and ($t_{NEW}-t_{OFF}$) is determined to be thirty seconds. If Y is greater than one degree per minute, then the meter will then set Temp_Event2 to True at step 2354. Once Temp_Event2 has been reset, the meter may stop doing determinations, until the next time a strip is inserted. If Y is less than one degree per minute, Temp_Event1 is not stored and the algorithm proceeds to step 2340. Additional determinations may continue to occur at periodic time intervals (e.g., every fifteen seconds), until the meter is turned off, moves to menu mode, the meter has been removed for a predetermined period of time (e.g., five minutes) from a direct connection to a charge source (e.g., PC USB port), or a Temp_Event 2 is detected.

It is contemplated that the third component of the ambient temperature prediction algorithm relates to detecting charging or heat-generation within the meter in heightened—temperature environments. The occurrence of such an event can be identified and logged in a memory as a special event or suspect-value event that includes an identifier so that the logged event can be correlated with an analyte concentration result. Logged events may be used by a servicer to assess the performance of a meter. Special event can be stored similar to errors. Examples of special event or suspect-value events include: (i) Temp_Event1 which indicates that a test has been conducted and the analyte concentration result was reviewed before the meter had sufficient time to determine whether the meter was directly connected to a PC or other charging device contributing to a significant temperature difference between the meter and the room in which the test was being performed—see, e.g., FIGS. 22b and 23b; (ii) Temp_Event2 which indicates that a test has been conducted during time period when the meter detected a connection to a PC or other charging device that contributed to a significant temperature difference between the meter and the room in which the test was being performed—see, e.g., FIG. 23b; and (iii) Temp_Event3 which indicates that a test has been conducted during a time period when the meter detected a rapid temperature drop that is not definitively associated with charging the meter—see, e.g., FIG. 22a and first component of ambient temperature prediction algorithm.

Figure 24:
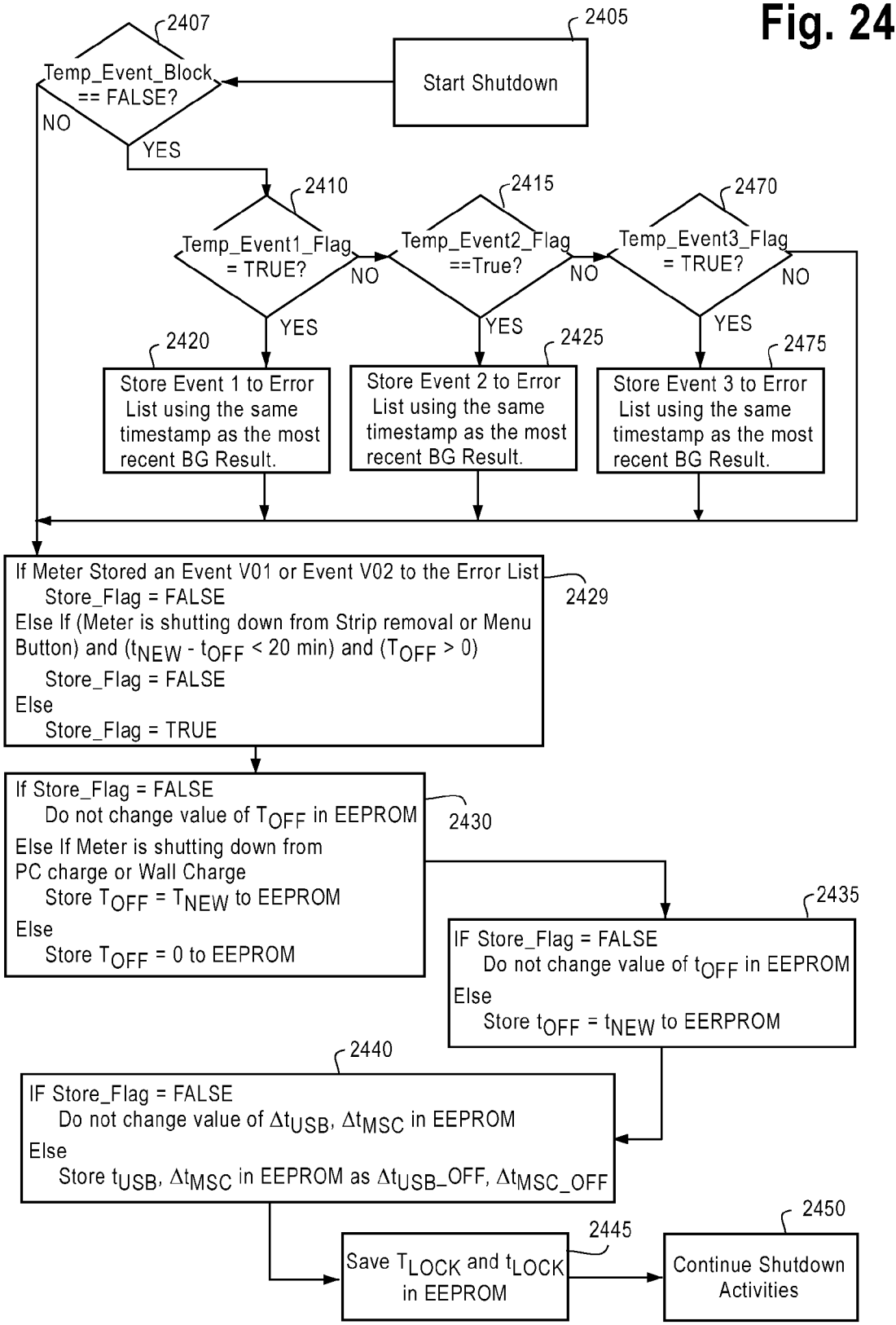
FIG. 24 illustrates a logical flow diagram for storing temperature-related data according to an embodiment.

Referring now to FIG. 24, aspects of the shutdown routine described in FIG. 20 are illustrated in more detail according to certain embodiments of the present disclosure. Furthermore, additional details are provided on the various special events that may be recorded or logged by the meter. At step 2405, shutdown is initiated by the meter. At steps 2410 and 2415, assessments are made regarding whether Temp_Event1, Temp_Event2, and/or Temp_Event3 are true. If the answer to these conditions is no, the method proceeds to step 2429. However, if Temp_Event1 is true then Temp_Event1 is stored or logged with the same timestamp as the most recent analyte concentration test result (e.g., blood glucose test result). Similarly, if Temp_Event2 or Temp_Event3 are true, then Temp_Event2 or Temp_Event3 are respectively stored or logged with the same timestamp as the most recent analyte concentration test result. The method then proceeds to step 2429 where a logical operator, Store_Flag is set which determines in subsequent steps what data are stored in non-volatile memory. Next, at step 2430, a determination is made as to what temperature value should be stored in the non-volatile memory for $T_{OFF}$ based on the value of Store_Flag and whether the meter is shutting down from a direct or indirect charge state. At step 2435, a logical operator determines what values of $t_{OFF}$ should be stored in non-volatile memory. The shutdown process continues with steps 2440 and 2445, which include saving the recent values for $\Delta t_{USB}$, $\Delta t_{MSC}$, $T_{LOCK}$, and $t_{LOCK}$ to a non-volatile memory before continuing with shutdown activities at step 2450 and shutting down the meter.

It is contemplated that in certain embodiments the temperature corrections determined for PC or direct charging and for mass storage are based on linear models or relationships. Different correction factors are determined based on the individual models developed for each heat generating element associated with a fluid analyte meter. It is contemplated that it may be desirable for the ambient temperature prediction process to check if the sum of correction values associated with the PC charging and the mass storage activity is greater than one degree Celsius. If so, the 0.5 degree Celsius correction from the first component of the algorithm or process described above may not be a sufficient correction. Furthermore, the value of $T_{LOCK}$ can then be corrected by subtracting the sum of the correction values for PC charging and mass storage activity from the from the second component of the ambient temperature prediction algorithm. If temperature correction takes place according to the second component of the ambient temperature prediction algorithm, the flag or event for a 0.5 degree Celsius correction from the first component is reset, so that both corrections are not applied. If the sum of the two corrections is not greater than one degree Celsius, the algorithm will proceed with the first component of the ambient temperature prediction algorithm.

Figure 25:
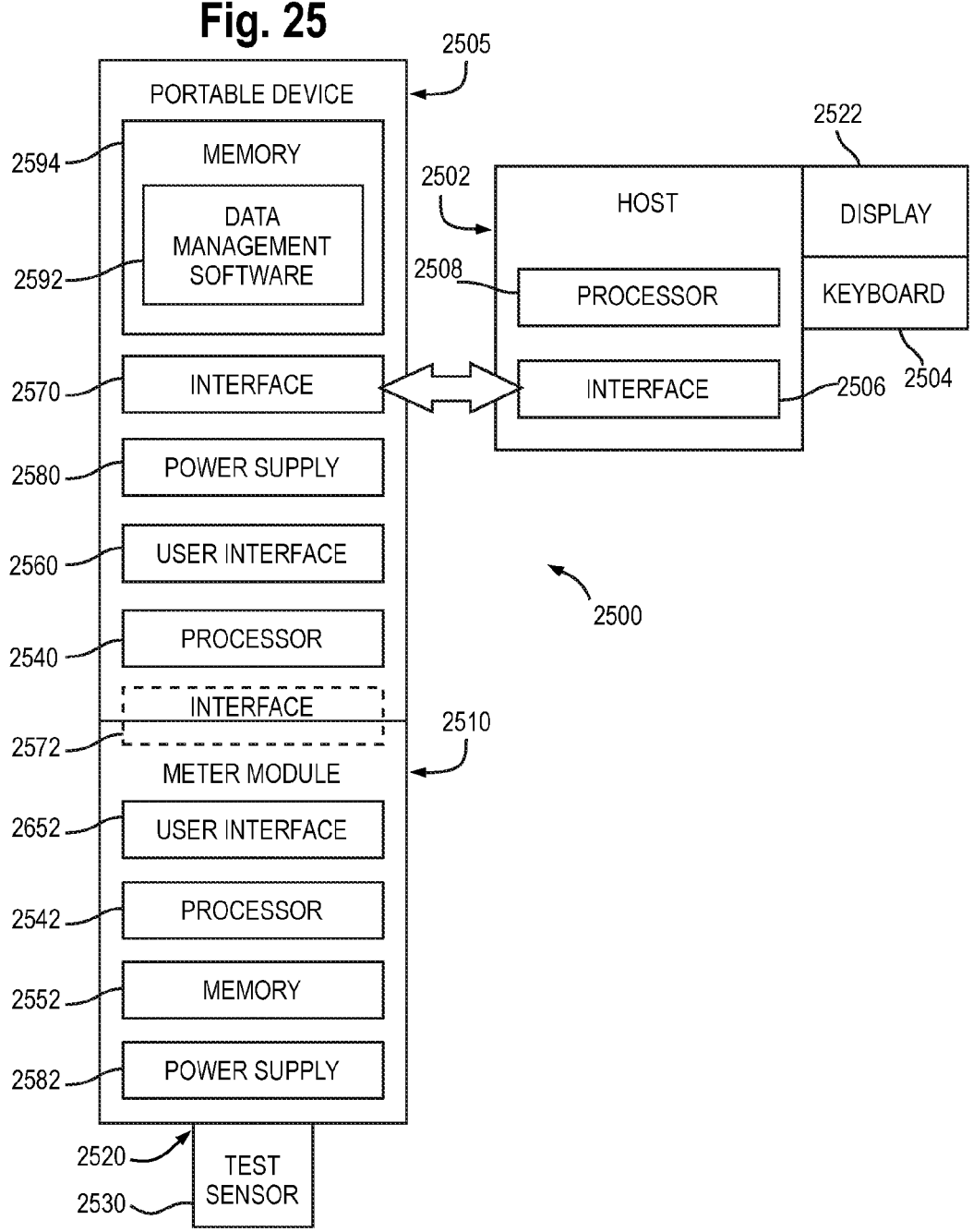
FIG. 25 illustrates a fluid analyte system including an integrated device that provides a measurement system and a user interface according to another embodiment.

It is contemplated that in certain embodiments an integrated fluid analyte system 2500, as illustrated in FIG. 25, can incorporate the components and functions of the portable device 2505 with the components and functions of the meter module 2510. Portable device 2505 and meter module 2510 may be connected, such as via a physical connection, through an interface 2572. The integrated device 2500 can receive an analyte-test sensor 2530 via a port 2520. The integrated device 2500 can also include processors 2540, 2542 that can calculate, for example, the concentration of analyte in the sample collected by the test sensor 2530. The processors 2540, 2542 in the integrated device 2500 can also process information from the detection of a reaction between the sample and a reagent on the test sensor 2530. The test results are stored in at least one of memories 2552, 2594 of the integrated device 2500. As such, the memories 2552, 2594 may have a capacity in the range of about 500 MB to about 2 GB. The integrated fluid analyte device 2500 can also include one or more user interfaces 2560, 2562 that are used to display the test results and to enter input for various display options.

In certain embodiments, the integrated system 2500 can be a portable blood glucose meter that provides data processing and display features. Users can employ the integrated device 2500 to provide a blood sample via the test sensor 2530 and can further access more sophisticated presentations of blood glucose test data from the integrated device 2500 without launching data-management application on a separate processing device 2502. However, as hardware limitations may still prevent all desired functionality to be incorporated into the integrated device 2500, the integrated device 2500 retains the ability to launch the data-management application on a larger processing device 2502 and to provide the user with functionality not available on the integrated device.

It is contemplated that the integrated device 2500 can connect wirelessly to more than one type of processing device 2502, including a laptop PC and mobile communication devices. In certain embodiments, interface element 2570 associated with the integrated device 200 connects with interface element 2506 of the processing device 2502 to allow data transfer from the integrated device 2500 to the processing device 2502. The processing device 2502 may already include data management software or the data management software 2592 from the integrated device 2500 can be used to analyze collected data. The processing device 2502 can further include a processor, a user input device 2504, and a display 2522 to assist with the downloading and/or analysis of data, for example, blood glucose readings and time-stamp information, retrieved from the integrated device 2500. In general, the portable device 2505 may be integrated with varying levels of functionalities, such as user interface features and measurement system capabilities. However, any device employing components and functions of the portable device 2505 may include a user interface, even if it does not incorporate components and functions of the meter module 110.

Figure 26:
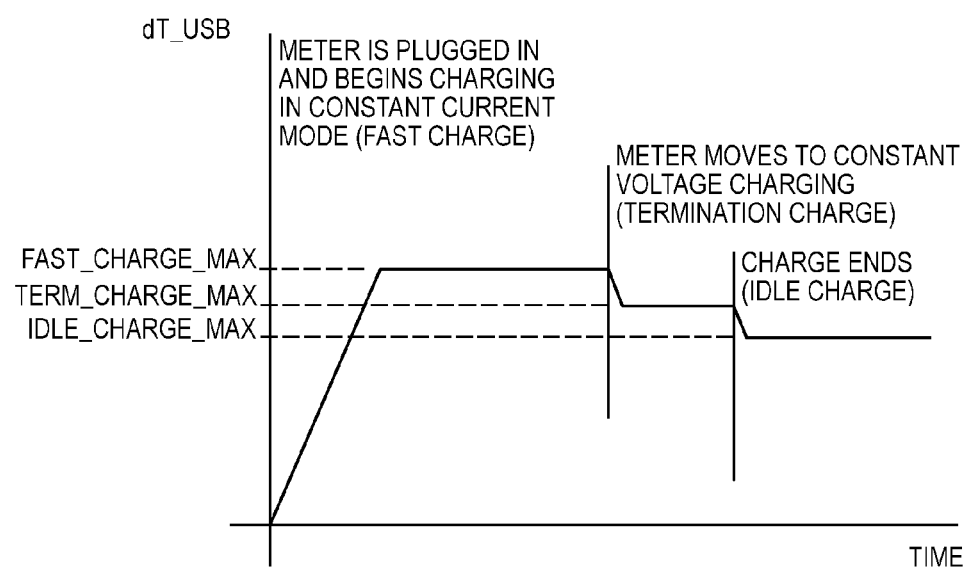
FIG. 26 illustrates the tracking of time based on the charge state of a battery for determining a temperature target based on power consumption according to one embodiment.

Referring now to FIG. 26, an illustration is made of an embodiment in which a length of time is maintained to record the length of charging of a battery in a fluid analyte system. This length of time, $\Delta t_{USB}$ (e.g., dt_USB), has a cap or upper boundary that is based on the charge state of the battery. In the example of FIG. 26, as the fast charge of a battery nears completion the upper level decreases for each lower state as the battery charge nears and reaches completion. This length of time, $\Delta t_{USB}$, can be used in temperature prediction algorithms since heat generation in a system can be approximated based on a charge state (e.g., fast, termination, idle) and the length of the charge state. It is contemplated that measurement of temperature rise based on a length of time can be desirable for predicting temperature changes because it can factor in the time that a meter is off and the temperature recovers. It is further contemplated that each of the charge state upper levels (e.g., fast charge max, termination charge max, idle charge max) can be useful for establishing a target temperature rise level within a fluid analyte system, such as the systems described herein, including a meter module.

Similar to the temperature rise that may be calculated based on a length of time as described above for FIG. 26 for a charge state of a fluid analyte system (and as discussed elsewhere herein), it is contemplated that ambient temperature predictions based on temperature rise can also be made for a fluid analyte system in a discharge state. This can be accomplished by maintaining a value for the fluid analyte system that represents Temperature Rise ($T_{Rise}$). It is contemplated that predicting ambient temperature using such a method can include determining a Temperature Target ($T_{Target}$) based on power consumption of the elements associated with, for example, a meter module. For example, a Temperature Target may be determined based on the power consumption of a portable device interfaced with a meter module.

Determining $T_{Target}$ is beneficial because it can guide how $T_{Rise}$ changes over time. $T_{Target}$ is determined using the power from a battery or other power supply as calculated from the power supply current and voltage. It is desirable to update $T_{Target}$ at regular time intervals. In certain embodiments, $T_{Target}$ can be updated every fifteen seconds. In another embodiment, $T_{Target}$ can be updated every minute. Shorter (e.g., <15 seconds, <1 minute) and longer (e.g., >15 seconds, >1 minute) time intervals are contemplated for updating $T_{Target}$. It is desirable to update $T_{Rise}$ at regular time intervals because $T_{Rise}$ is used in the ambient temperature calculation. I certain embodiments, $T_{Target}$ and $T_{Rise}$ are updated at the same or similar time intervals.

The ambient temperature prediction methods include several symbols that can be defined for certain embodiments as follows:

| Symbol | Definition |
| --- | --- |
| $P_{Now}$ | Calculated power from Battery Current/Voltage Data |
| $T_{Target}$ | Target Temperature Rise (above ambient) |
| $T_{Rise}$ | Expected temperature rise above ambient, value is obtained from last temperature history update |
| $T_{Diff}$ | is the difference between the target temperature rise ($T_{Target}$) and expected temperature rise (RBG) |
| $T_{Shift}$ | is the predicted temperature shift in RBG from the last update as it approaches the target |
| $\Delta t_{USB}$ | A period of time that is saved, through resets, and stores a length of time for which USB has been active. |

Figure 29:
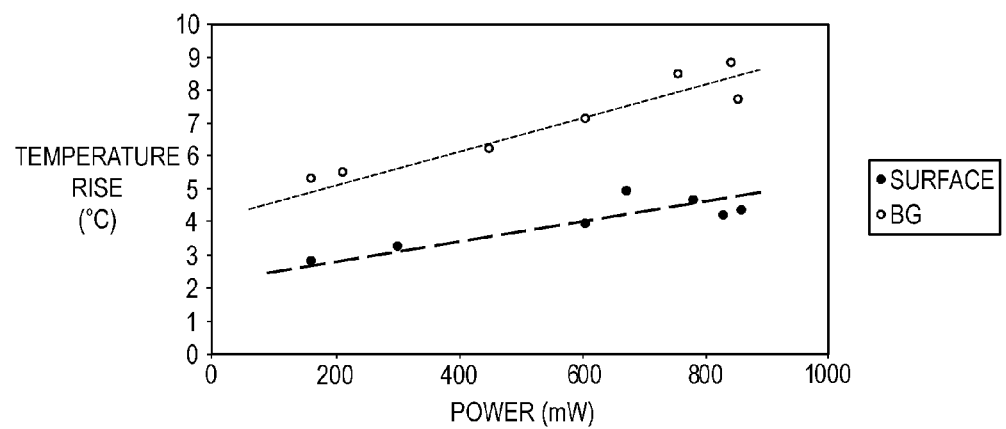
FIG. 29 illustrates linear approximations of temperature rise targets for a fluid analyte meter in a charge state according to another embodiment.
Figure 30:
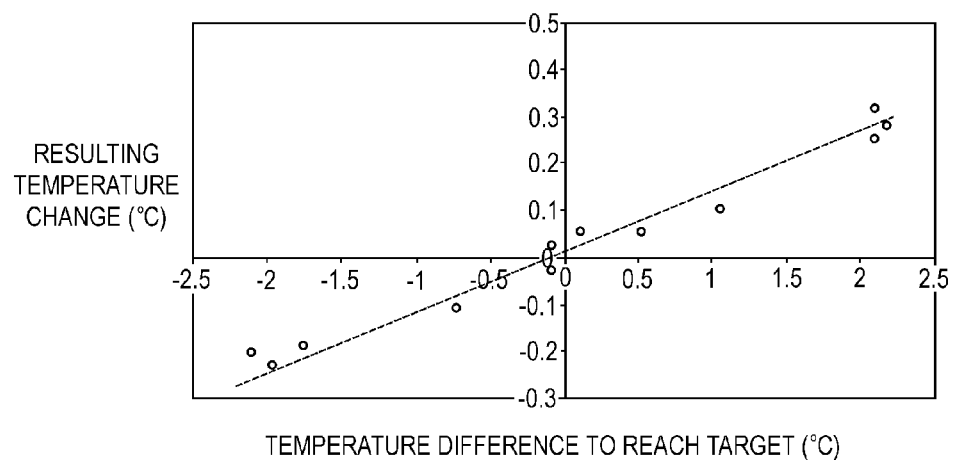
FIG. 30 illustrates a linear approximation of temperature rise change according to another embodiment.
Figure 31:
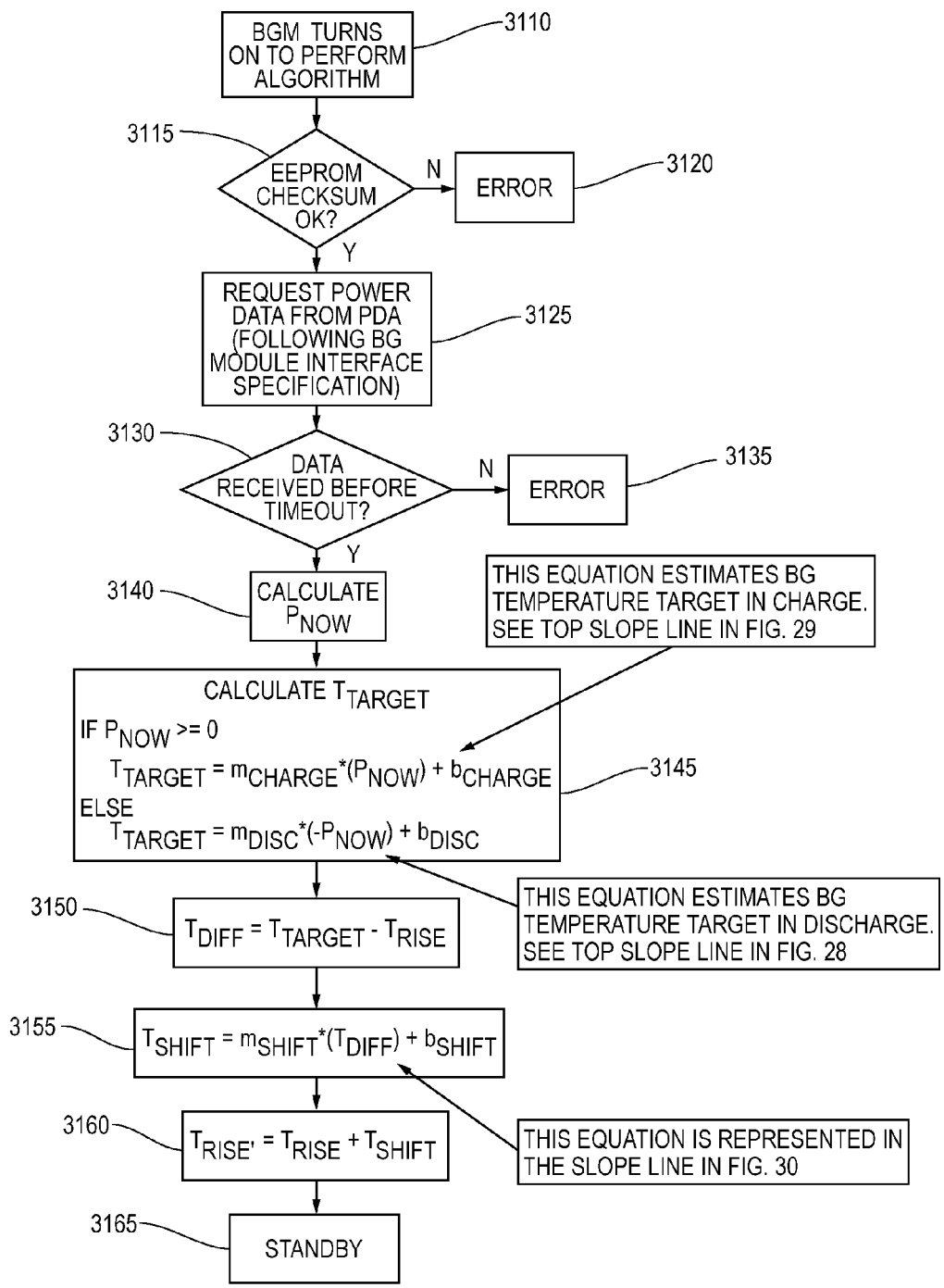
FIG. 31 illustrates a logical flow diagram of a method for tracking temperature rise in a meter during a low-power consumption state according to another embodiment.
Figure 32:
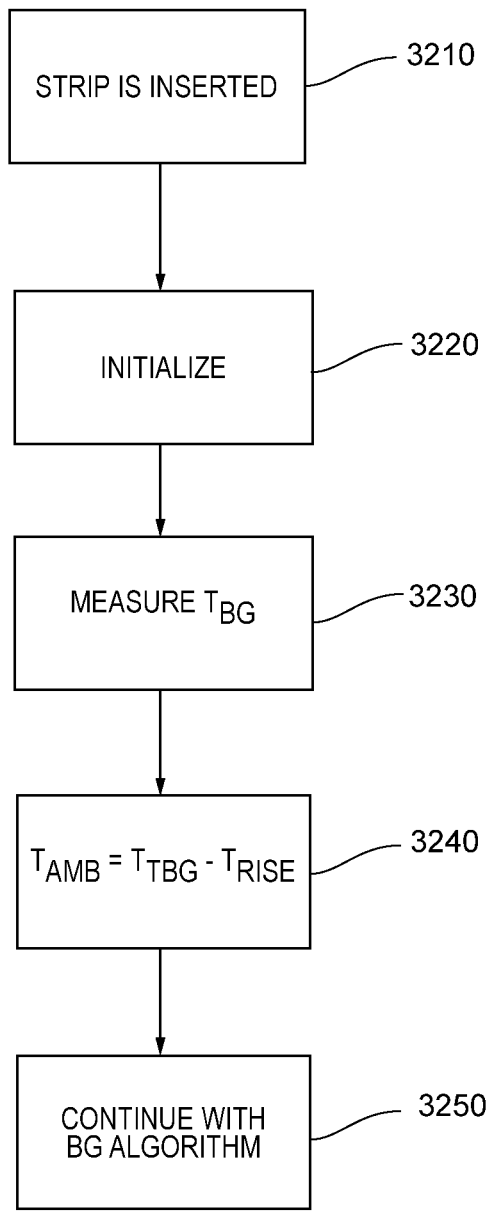
FIG. 32 illustrates a logical flow diagram of a method for predicting temperature during a testing state of a meter according to another embodiment.

Referring now to FIGS. 27-30, exemplary embodiments are illustrated for methods used to determine parameters for the ambient temperature prediction algorithms discuss in FIGS. 31 and 32. The exemplary embodiments of FIGS. 27-30 are based on experimental data collected to reflect an advanced portable electronic device (e.g., a personal digital assistant, Pocket PC, Smart Phone, etc.) configured to operate a variety of tasks via an operating system and various software applications. The advanced portable electronic device can be of the type that consume large amounts of power (e.g., up to 1,300 milliwatts or more) and may include, for example, a color graphical display, a keyboard, a touch screen interface, a rechargeable battery, a camera, an interface for connecting to other devices, and/or an audio interface. Such a device could generate significant amounts of heat that exceed the tolerances associated with determining fluid analyte concentrations, and thus, may necessitate a correction of the ambient temperature used in the concentration determination. It is also contemplated that the portable electronic device may be a simple device that consume less power, and thus, generate less heat. Similar to the configurations illustrated in FIGS. 1, 2, and 25, the advanced portable electronic device can be interfaced with a meter module.

Figure 27:
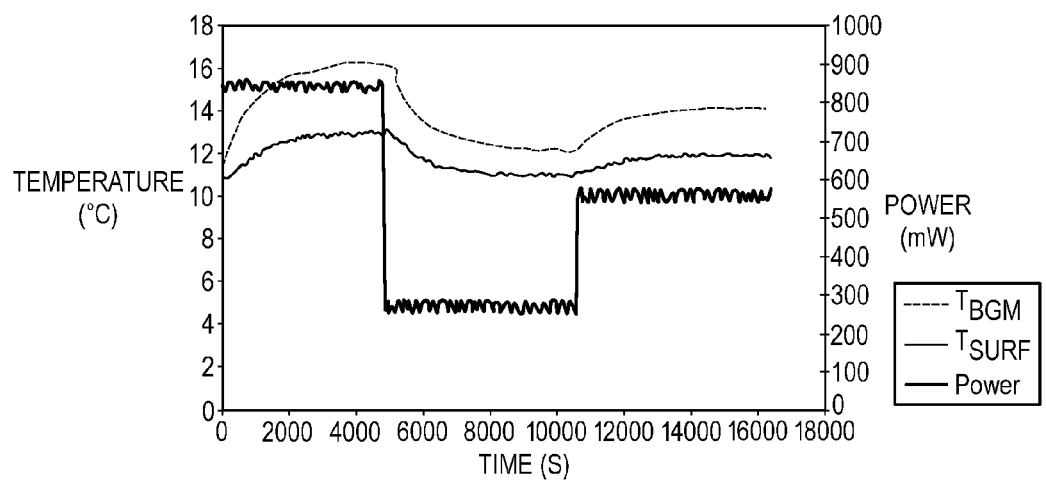
FIG. 27 illustrates a temperature profile for different discharge states of a battery for a fluid analyte meter according to another embodiment.

FIG. 27 illustrates an embodiment for the discharge from a power hungry portable device interfaced to a meter module. Multiple plots are illustrated for power (e.g., Power) over several periods of time and the associated raw temperatures measured over the same time periods by temperature sensors located on the interior (e.g., $T_{BGM}$) of a meter module and on the surface (e.g., $T_{SURF}$) of the same meter module. In certain embodiments, the temperature sensor may be located on a printed circuit board within the housing of a meter module or on an unhoused printed circuit board. In certain embodiments, the temperature sensor is a thermistor embedded near the exterior surface but within the housing of a meter module. The primary source of heat in FIG. 27 is from the power output of a portable device, such as the portable advanced electronic device discussed in the previous paragraph. FIG. 27 illustrates a portable device in various discharge states, including a high power consumption discharge state (e.g., from Time=0 to approximately Time=4,500 seconds), a low power consumption discharge state (e.g., from approximately Time=4,500 to approximately Time=10,500 seconds), and a medium power consumption state (e.g., from approximately Time=10,500 seconds to approximately Time=16,000 seconds). The data was collected in a stable temperature chamber to minimize the influence of outside environmental factors on the collected temperature data. The meter module with no battery was allowed to settle to the chamber temperature. Next the battery was inserted, the meter booted up, and data collection software was used to cycle through the high, low, and medium discharge states. The plotted data also reflect the meter module being allowed to settle for at least 1.5 hours after changing discharge states, so that equilibrium could be achieved. As the data associated with Tbgm and Tsur was sent from the meter module to the advanced portable electronic device, battery current and voltage information was also recorded to allow calculation of power in FIG. 27.

While the data illustrated in FIG. 27 shows positive power values, it is noted that the data is actually negative because the device and meter are in a discharge state with the battery expending energy. It is further noted that in certain embodiments, all the power values are positive (see, e.g., FIG. 36). FIG. 27 is particularly useful because it illustrates that the temperature on the surface or within a meter module for a portable meter and meter module arrangement will settle to a steady-state value for a given amount of power consumed. Thus, a steady-state temperature can be achieved, but the value changes as the power consumption changes.

Figure 28:
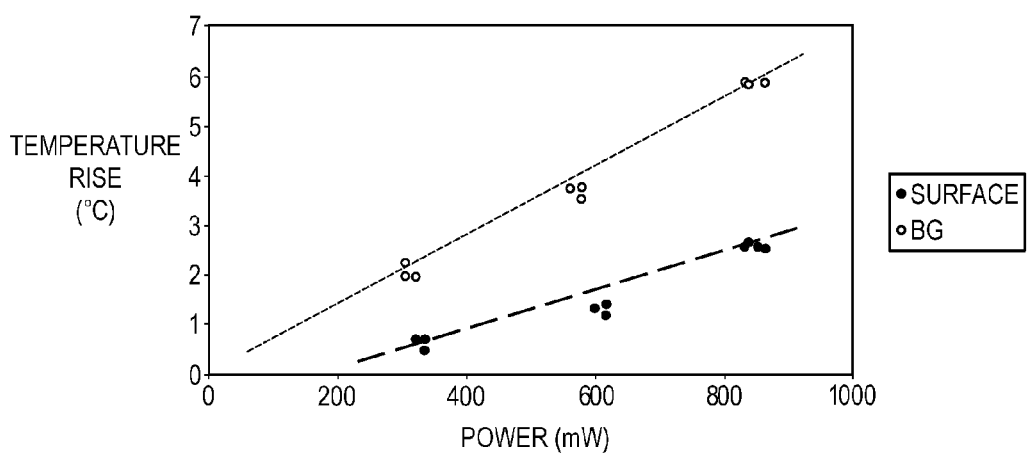
FIG. 28 illustrates linear approximations of temperature rise targets for a fluid analyte meter at different battery discharge states according to another embodiment.

Referring now to FIG. 28, an exemplary target temperature rise plot is illustrated based on data from both the temperature sensor located on the interior of the meter module and the temperature sensor located on the surface of the housing of the meter module. The exemplary target temperature rise values can be determined of a specific meter by developing a similar plot to that presented in FIG. 27 for various power consumption states (e.g., low, medium, high). Looking at some of the data illustrated in FIG. 28, the low, medium, and high power consumption values were approximately 300 milliwatts, 600 milliwatts, and 850 milliwatts, respectively. The final plot of temperature rise for each of the surface and interior temperature sensors was based on the temperature reaching the steady state value for the respective discharge power consumption state. Combining the methods illustrated in FIGS. 27 and 28, the slope of target temperature rise versus power consumption can be readily determined for a given fluid analyte system, including, for example, a portable meter and meter module arrangement. The slope of the lines for each temperature sensor readily allows the determination of target temperature rise for a wider range of power consumption levels for the fluid analyte system.

Referring now to FIG. 29, an exemplary target temperature rise plot can also be determined using temperature sensor data collected during various charge states for a fluid analyte system arrangement. The difference between the charge state and discharge state are that the battery for the fluid analyte system results in positive currents when charging, whereas negative currents result during the discharge state. While the negative and positive values make it easy to distinguish between charge and discharge states, the data is generally reviewed as absolute values. FIG. 29 illustrates an exemplary single charge state based on a medium amount of power consumption in the fluid analyte system. The charging was completed from a PC connected to the fluid analyte system (e.g., a USB portable device). FIG. 29 illustrates that in the charge state the relationship of target temperature rise and power (while generally linear, similar to the discharge state of FIG. 28), the slope profile is different from the discharge relationships.

FIGS. 27-29 illustrate the development of the relationship of target temperature rise for various power consumption states within the charge and discharge modes of an exemplary fluid analyte meter embodiment. The methods to develop the relationship can be applied to various fluid analyte system configurations such as those illustrated in FIGS. 1-4, 25, and identified elsewhere herein. However, development of parameters for an ambient temperature prediction algorithm applicable to the systems identified herein would benefit from a model of the behavior of temperature rise (e.g. $T_{Rise}$) as it approaches the target temperature rise (e.g., $T_{Target}$). FIG. 30 illustrates embodiments of a predictive model for temperature change over a preselected period of time (e.g., approximately 15 second interval, approximately 1 minute interval, etc.) based on the difference between temperature rise and target temperature rise.

The horizontal (x) axis of FIG. 30 is the temperature difference between the target temperature rise, $T_{Target}$, calculated using the power data such as illustrated in FIGS. 27-29, and the actual temperature rise in the meter determined at the immediately prior time interval (e.g., approximately 15 seconds prior, approximately 1 minute prior, other predetermined time interval[s]). The vertical (y) axis of FIG. 30 is the resulting change in the temperature rise in the meter, calculated by subtracting the temperature rise measured 1 minute in the past (e.g., at the immediately prior time interval) from the measured present temperature rise. Both measurements can be made using a temperature sensor, such as a sensor located within the meter module or on the surface of the meter module or a housing associated with a portable device.

FIG. 30 illustrates an exemplary linear approximation based on temperature data collected for a temperature sensor located within a meter module near the test sensor. The linear approximation allows for a good approximation of the change in temperature rise with any target temperature rise. The methods used to determine the key parameters for predicting ambient temperature described herein can be readily adapted to any meter and can also be developed to accommodate the entire power range of the meter. With the ability to model temperature rise in the meter across the entire power range, the predictive model can handle the contemplated use scenarios for the meter and remain independent of the environment and handling.

It is contemplated that in certain embodiments, a meter module and/or the entire fluid analyte system may be subject to a power range from approximately 0 up to approximately 1,300 milliwatts, where the lower end of the range represents the meter module in a standby mode and the higher end of the range represents a charging or extreme load discharge state. Ranges higher than 1,300 milliwatts are also contemplated. It is further contemplated that the meter module may operate in varying temperature ranges. In one embodiment, the meter module may be subject to temperatures ranging from approximately 5 degrees Celsius to 45 degrees Celsius. In another embodiment, the meter module may be subject to temperatures of up to approximately 55 degrees Celsius.

It is contemplated that in certain embodiments the term, target temperature or $T_{TARGET}$ will be understood to refer to a long-term temperature settling point or threshold that given a fixed amount of power consumption or a regularly repeating pattern of power consumption, a fluid analyte meter or meter module will reach within a predetermined period of time (e.g., twenty to thirty minutes, less than twenty minutes, greater than thirty minutes). Such a target temperature can then determined using the equations at steps 3145 or 3645 of FIG. 31 or 36 and by measuring power consumption and determining constants as illustrated, for example, in FIGS. 28 and 29.

FIG. 31 illustrates an example for determining a temperature rise value for a blood glucose meter module (e.g., a type of fluid analyte meter) in a low power consumption mode (e.g., low state). At step 3110, the meter module turns on to perform the temperature rise determination. In one exemplary embodiment, the meter module may turn on or wake up every minute to perform the temperature rise determination. Other time intervals are also contemplated such that that the needs of the meter are met to accurately predict ambient temperature for the fluid analyte concentration determination. At step 3115, the meter module performs an EEPROM checksum determination. If there is an error, the algorithm proceeds to step 3120 and reports an error. If the EEPROM checksum is okay, the algorithm proceeds to step 3125 and the meter module requests power data from a portable device (e.g., a PDA or other advance portable electronic device). At step 3130, the meter checks if data was received before a timeout. If portable device does not respond, an error may be reported at step 3135 and the meter module may assume it is in a standby mode with no temperature rise. If the portable device does respond, the meter module determines power from the battery current and voltage data received from the PDA in step 3125.

At step 3145, the target temperature rise is estimated for both the charge mode and the discharge mode. As illustrated in FIGS. 28 and 29, the slope for the linear approximations for the charge and discharge modes varies, and thus, the equation used to estimate the target temperature rise depends on whether the calculated power in step 3140 is positive (charge mode) or negative (discharge mode). The variables $m_{disc}$ and $b_{disc}$ represent the slope and y-axis intercept for the slope of the discharge target temperature rise approximation, such as the one determined in FIG. 28. The variables $m_{charge}$ and $b_{charge}$ represent the slope and x-axis intercept for the slope of the charge target temperature rise approximation, such as the one determined in FIG. 29.

At step 3150, the difference is determined between the target temperature rise calculated in step 3145 and the actual temperature rise in the meter module from an immediately prior measurement time period. Then at step 3155, a predicted temperature shift in the meter module is determined using the slope and y-axis intercept of a linear approximation determined according to the procedures discussed for FIG. 30. The predicted temperature shift is also based on the difference between the target temperature rise and the expected temperature rise in the meter module, determined in step 3150.

At step 3160, the temperature rise value is then reset for the present time interval to equal the previous value of temperature rise plus the predicted temperature shift determined in step 3155. The temperature rise value can be stored in a memory associated with the meter module. Next, at step 3165, the meter module can then go into a standby mode until prompted to again perform the steps outlined in FIG. 31 at the next predetermined time interval. The predetermined time interval can vary as necessary to meet the parameters for accurately predicting ambient temperature while balancing the need to reasonably conserve battery power.

If a test strip is inserted into the meter module, the meter module then transitions to a test state following the algorithm illustrated in FIG. 32. At step 3210, the test strip is inserted into the meter module. At step 3220, the meter module and/or system then initializes as it exits the standby or sleep mode. At step 3230, the meter module measures the value at the temperature sensor on the meter module. In the exemplary embodiment of FIG. 32, the temperature value in the interior of the housing of the meter module can be determined at step 3230. Then, at step 3240, a prediction of ambient temperature is made based on the difference of the temperature value determined at step 3230 and the latest value of temperature rise determined in the algorithm illustrated in FIG. 31. At step 3250, a determination of fluid analyte concentration is then made using an algorithm that includes the predicted ambient temperature determined in step 3240.

Figure 33:
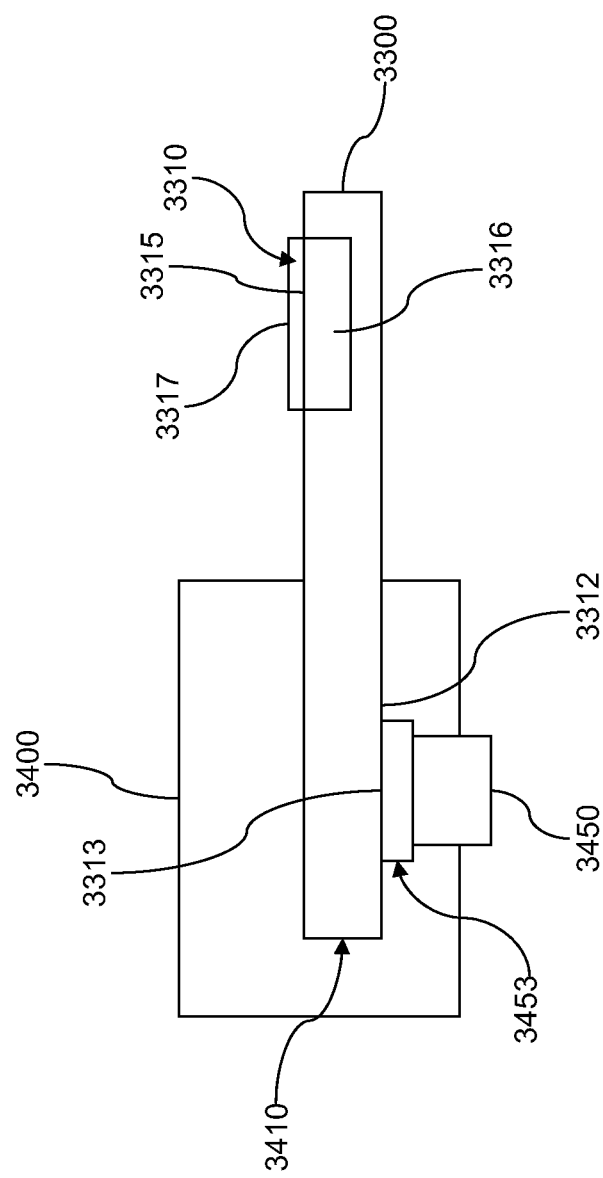
FIG. 33 illustrates a test sensor inserted into a meter according to aspects of the present invention.

The temperature effects of heat transfer between a test sensor 3300 and a meter 3400 are further described with reference to the configuration shown in FIG. 33. In particular, FIG. 33 shows a test-sensor opening 3410 of a meter 3400 that receives and engages a received area 3312 of a test sensor 3300. A temperature measuring system 3450 determines the temperature T from a measured area 3313, i.e., a part of the received area 3312 that is positioned proximate to the temperature measuring system 3450. The temperature measuring system 3450, for example, may employ an infrared thermopile sensor or an optical-sensing system. In addition, an insulating air pocket 3453 may be formed by a gap between the temperature measuring system 3450 and the measured area 3313. Due to the temperature changes that may occur specifically at the measured area 3313, the temperature T at the measured area 3313 may be different from the temperature $T_s$ generally associated with the test sensor 3300.

In general, the temperature measuring system 3450 in the meter 3400 may be able to measure the temperature $T_s$ of the test sensor 3300 with a very short response time, i.e., almost as soon as the test sensor 3300 is inserted into the test-sensor opening 3410 at time $t_1$. However, the temperature $T_m$ of the meter 3400 at the time $t_1$ may be different from the temperature of the test sensor $T_s$, and this temperature difference between the meter 3400 and the test sensor 3300 may cause the received area 3312 to experience temperature changes via heat transfer. For example, as discussed previously, the received area 3312 may receive heat from sources associated with the meter 3400. Although the test sensor 3300 may be formed from a plastic that is a poor thermal conductor, the thermal mass of the test sensor 3300 may be so small that heat transfer with the meter 3400 may produce significant and relatively rapid temperature changes in areas of the test sensor 3300. In some cases, the temperature measuring system 3450 may not be able to measure the temperature $T_s$ of the test sensor 3300 before the received area 3312 experiences the effects of heat transfer with the meter 3400. As such, a simple measurement from the received area 3312 by the temperature measuring system 3450 may not accurately reflect the temperature $T_s$ of the test sensor at time $t_1$. Without a more accurate determination of the temperature $T_s$ and thus the temperature of the reagent 3315, the determination of the analyte concentration cannot accurately account for the temperature of the reagent during the reaction.

If the temperature $T_m$ of the meter 3400 is greater than the temperature $T_s$ of the test sensor 3300, the measured area 3313 may come into contact with the hotter meter 3400 when the test sensor 3300 is initially inserted into the test-sensor opening 3410. As a result, the measured area 3313 may experience rapid heat transfer from the meter 3400, and the temperature T at the measured area 3313 may increase initially. However, once the test sensor 3300 is fully received into the test-sensor opening 3410, the measured area 3313 is positioned proximate to the temperature measuring system 3450 and becomes insulated by the air pocket 3453. At this stage, there is no direct contact, and corresponding heat transfer, between the meter 3400 and the measured area 3313. On the one hand, the measured area 3313 may start to cool due to heat transfer from the measured area 3313 to the bulk material of the test sensor 3300, which generally remains at the lower temperature $T_s$. On the other hand, other areas of the received 3312 are now in contact with, or otherwise exposed to, the hotter meter 3400, so the measured area 3313 may experience heat transfer from the meter 3400 according to different pathways, i.e., without direct contact with the meter 3400.

Figure 34:
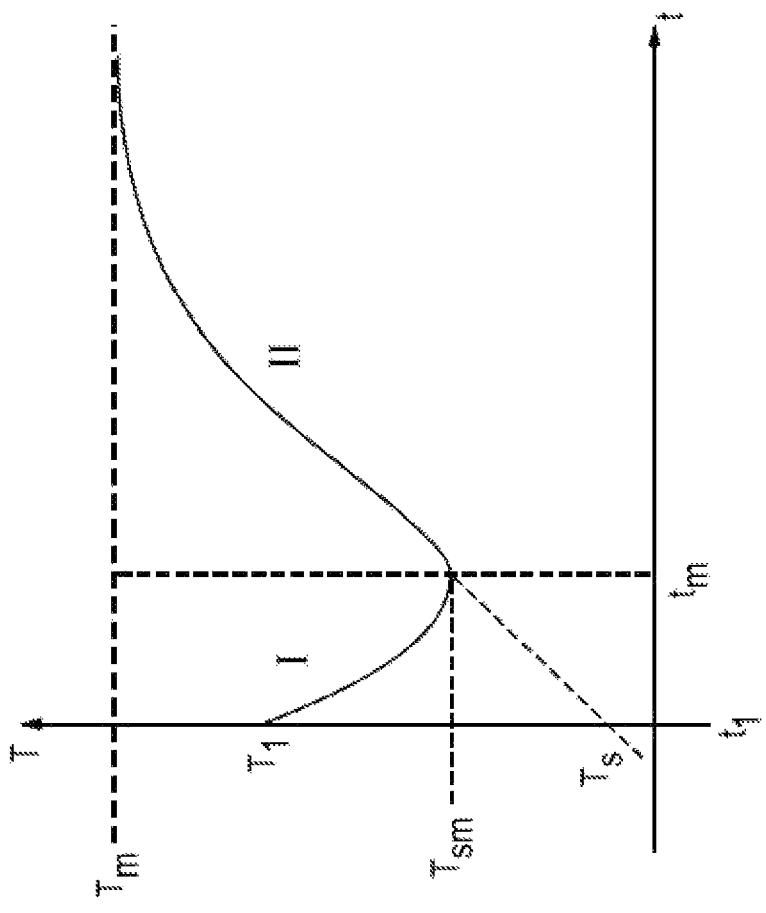
FIG. 34 illustrates a graph of the temperature T at the measured area of a test sensor as a function of time t after the test sensor inserted into a meter according to aspects of the present invention.

FIG. 34 illustrates a graph of the temperature T at the measured area 3313 as a function of time t, where $T_m$ is the meter temperature; $T_s$ is the general test sensor temperature; and $T_1$ is the first temperature measured at measured area 3313 when the test sensor 3300 is fully inserted into the test-sensor opening at time $t_1$. Part I of the graph in FIG. 34 illustrates the effect of the cooling that the measured area 3313 experiences when it is first positioned over the temperature measuring system 3450 and is no longer in direct contact with the hotter meter 3400. Meanwhile, part II of the graph illustrates the effect of the heat transfer from the meter 3400 to the measured area 3313 due to the exposure of other areas of the received 3312 to the hotter meter 3400.

The cooling represented by part I of the graph may be modeled according to the following equation:

$$T(t) = (T_1 - T_s)e^{-t/T_C} + T_s \quad \text{(Equation 8)},$$

where $T_C$=time constant for part I. The heating represented by part II of the graph may be modeled according to the following equation:

$$T(t) = (T_m - T_s)(1 - e^{-t/T_H}) \quad \text{(Equation 9)}$$

where $T_H$=time constant for part II. Thus, the overall temperature curve in FIG. 34 may be modeled according to the following equation:

$$T(t) = T_m + (T_1 - T_s)e^{-t/T_C} - (T_m - T_s)e^{-t/T_H} \quad \text{(Equation 10)}.$$

Alternatively, where $a=1/T_C$, $b=1/T_H$, $c=T_m$, $d=T_1-T_s$, and $f=T_m-T_s$, Equation 10 may be expressed as:

$$T(t) = c + de^{-at} - fe^{-bt} \quad \text{(Equation 11)}.$$

As $T_s = c - f$ and $d = T_1 - c + f$, Equation 11 may also be expressed as:

$$T(t) = c + (T_1 - c + f)e^{-at} - fe^{-bt} \quad \text{(Equation 12)}.$$

The values a and b are system parameters, i.e., time constants, that may be determined and calibrated with system design and configuration. Thus, c and f may be determined by fitting Equation 12 to a series of temperature measurements from the temperature measurement system 3450. $T_s$ can then be calculated as the difference between c and f.

In some instances, the temperature $T_m$ of the meter 3400 may be lower than the temperature $T_s$ of the test sensor 3300. In these instances, the d and f in Equation 11 are negative. Thus, a negative value for f from the fitting of Equation 12 to the temperature measurements T indicates that the meter 3400 is cooler than the test sensor 3300.

Figure 35:
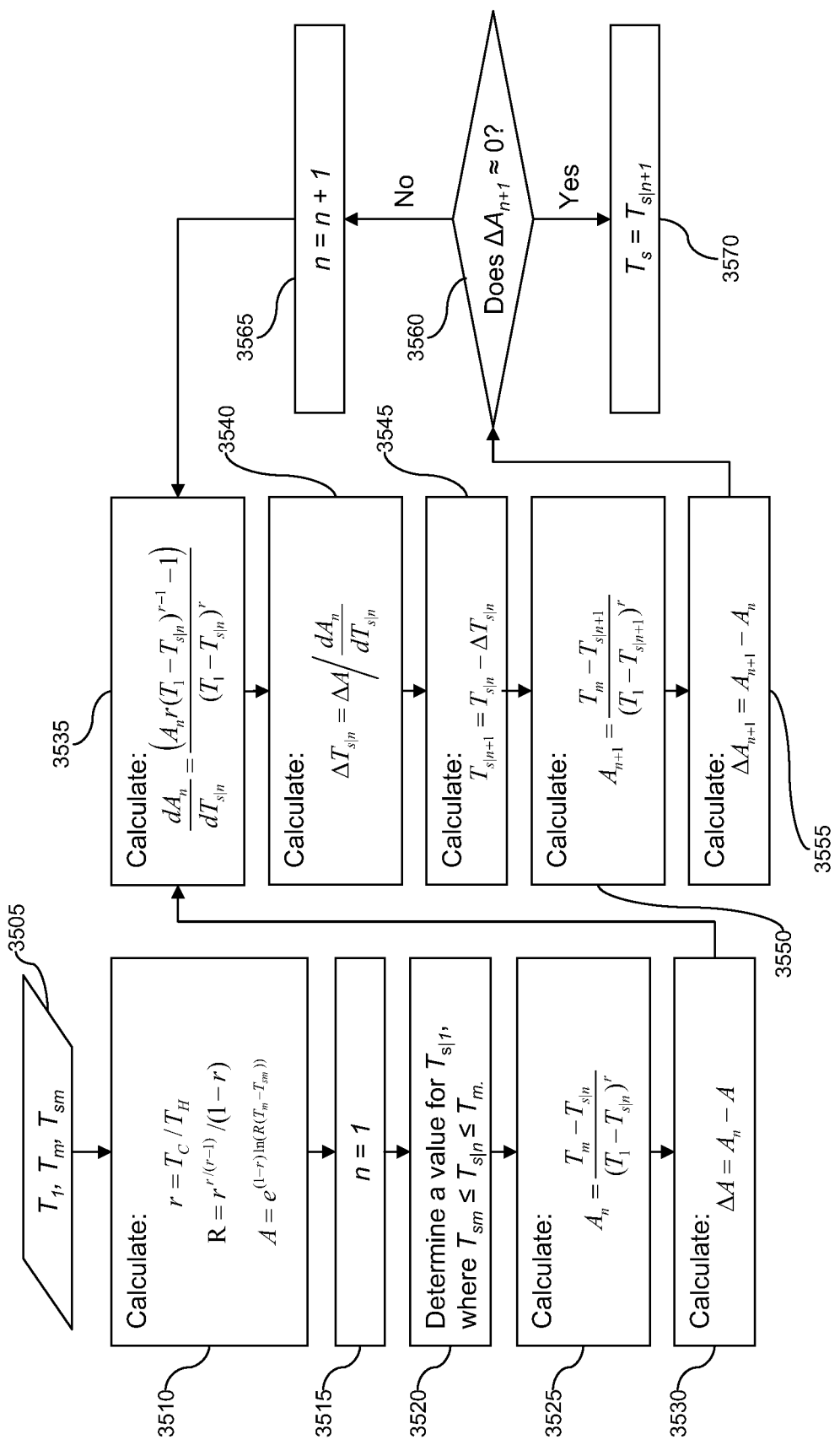
FIG. 35 illustrates an iteration method for determining a test-sensor reaction temperature according to aspects of the present invention.

The graph of FIG. 34 also shows a minimum temperature $T_{sm}$ of the measured area 3313 at a time $t_m$. If the temperature $T_m$ of the meter 3400 is lower than the temperature $T_s$, the value $T_{sm}$ represents a maximum temperature rather than a minimum temperature as shown in FIG. 34. The temperature measuring system 3450 can readily obtain the minimum temperature for $T_{sm}$ as well as the meter temperature $T_m$ and temperature $T_1$ of the measured area 3313 at time $t_1$. Accordingly, in an alternative approach, a curve is fitted to the three points corresponding to the temperatures $T_{sm}$, $T_m$, and $T_1$. As shown in APPENDIX A, the following equation may be derived from Equation 10 above:

$$T_m = T_s + A(T_1 - T_s)^r \quad \text{(Equation 13)},$$

where $A = e^{(1-r)ln(R(T_m - T_{sm}))}$, $r = T_C/T_H$, and $R = r^{r/(r-1)}/(1-r)$. Using the known values for $T_{sm}$, $T_m$, and $T_1$, a value for $T_s$ can be determined iteratively as illustrated in steps 3505, 3510, 3515, 3520, 3525, 3530, 3535, 3540, 3545, 3550, 3555, 3565, 3560, and 3570 in FIG. 35, according to the following equation:

$$\frac{dA}{dT_s} = \frac{(Ar(T_1 - T_s)^{r-1} - 1)}{(T_1 - T_s)^r}. \quad \text{(Equation 14)}$$

Table 3 provides results for experimental trials 1-9 conducted in a system with a configuration as shown in FIG. 33. As the results of Table 3 show, the value calculated for $T_s$ according to Equation 13 compares favorably to the value of (c−f) calculated according to Equation 12. Although the value of (c−f) may provide a higher confidence, calculating a value for $T_s$ according to Equation 13 provides a more efficient approach that only requires the measurement of three values, $T_{sm}$, $T_m$, and $T_1$, rather than 100 or more data points for example. As such, less computing effort is required and simpler electronics may be employed.

TABLE 3

Results for Experimental Trials 1-9 with System of FIG. 33

|     | 1 | 2 | 3 | 4 | 5 | 8 | 9 |
|-----|---|---|---|---|---|---|---|
| a | 2.799 | 2.248 | 2.534 | 2.324 | 1.777 | 1.849 | 2.965 |
| b | 0.4826 | 0.5396 | 0.5039 | 0.4976 | 0.5779 | 0.5742 | 0.4522 |
| c | 45.88 | 43.67 | 42.84 | 41.95 | 40.48 | 37.47 | 37.11 |
| f | 23.37 | 28.67 | 24.02 | 22.85 | 29.35 | 27.48 | 20.48 |
| c−f | 22.1100 | 15.0000 | 18.8200 | 19.1000 | 11.1300 | 9.9900 | 16.6300 |
| $T_m$ | 45.6861 | 44.4103 | 43.0971 | 41.9714 | 41.1459 | 37.9941 | 37.4688 |
| $T_1$ | 36.1748 | 33.9693 | 33.0568 | 32.6104 | 32.1691 | 29.3132 | 28.6133 |
| $T_{sm}$ | 30.4936 | 27.7163 | 28.0789 | 27.4915 | 26.5792 | 24.1677 | 23.3211 |
| $T_{st}$ | 21.87801 | 14.26804 | 18.52811 | 18.91284 | 9.575633 | 9.078628 | 16.21705 |

As discussed previously, a curve corresponding to Equation 10 is fitted to the three points corresponding to the temperatures $T_{sm}$, $T_m$, and $T_1$, where $T_1$ is measured by the temperature measuring system 3450 at the time $t_1$ when the test sensor 3300 is first received by the meter 3400. In a more general approach, however, the temperature measuring system 3450 may obtain a temperature $T_2$ at a time $t_2$ that may not necessarily be equal to the time $t_1$. For example, it may be easier and more practical to configure a system to measure a temperature $T_2$ at any time $t_2$ than to measure a temperature $T_1$ at the specific time $t_1$.

As shown further in APPENDIX B, the following equation may be derived from Equation 10:

$$T_m = T_s + A' g^r \quad \text{(Equation 15)},$$

where $A' = [R(T_m - T_{sm})]^{1-r} \cdot e^{t_2 r / T_C}$, $g' = T_2 - T_m + (T_m - T_s) e^{-t_2/T_H}$, $r = T_C / R_H$, and $R = r'^{(r-1)}/(1-r)$. Using the known values for the known temperatures $T_{sm}$, $T_m$, and $T_2$, a value for $T_s$ can be determined numerically in a technique similar to the iteration shown in FIG. 35. In this case, however, the following equation is employed:

$$\frac{dA'}{dT_s} = \frac{(rg'^{r-1} e^{-t_2/T_H} A' - 1)}{g'^r}. \quad \text{(Equation 16)}$$

Accordingly, determining the temperature of the test sensor 3300 can be obtained more generally from temperatures $T_{sm}$, $T_m$, as well as a temperature $T_2$ measured at any time $t_2$.

Typically, the thermal time constant for a plastic test sensor 3300 to reach equilibrium with the ambient during air cooling may be on the order of 40 seconds. Correspondingly, after the test sensor 3300 is inserted into the test-sensor opening 3410, the temperature of the reagent 3315, for example at a fluid-receiving area 3310 disposed at the end of the test sensor 3300, may remain substantially equal to the test sensor temperature $T_s$ for a relatively long period of time. For example, if the ambient temperature is 2° C. higher than the test sensor temperature $T_s$, it may take 40 seconds for the test sensor temperature $T_s$ to approach equilibrium with the ambient. It may take approximately 5 seconds to measure the reaction between the reagent and a sample and determine an analyte concentration once the test sensor 100 is inserted into the test-sensor opening 3410. During at least this first 5 seconds, the temperature of the reagent 3315 remains approximately equal to the test sensor temperature $T_s$. Moreover, the thermal time constant for heat to be transferred from the core of the test sensor 3300 to its surface may be approximately 0.4 seconds, which is short compared to the time to measure the reagent reaction. Therefore, the temperature of the sample collected at the fluid-receiving area 3310 should rapidly approach equilibrium with the test sensor temperature $T_s$ even if the sample initially retains some residual body heat, for example. This may be especially true as the sample volume is normally small compared to the volume of the test sensor 3300, e.g., at a ratio of 1 to 100.

Accordingly, the test sensor temperature $T_s$ may provide a very good approximation of the temperature for the temperature for the reaction between the reagent 3315 and the sample. To ensure the validity of this approximation, a thermal buffer 3316 surrounding the fluid-receiving area 3310 may be employed to promote the transfer of heat between the fluid-receiving area 3310 and the core of the test sensor 3300. A large core thermal mass may be disposed proximate to the fluid-receiving area 3310 and sandwiched with the fluid-receiving area 3310 by highly insulating material. An insulating window 3317 may be employed to cover the fluid-receiving area 3310 and minimize any heat transfer between the fluid-receiving area 3310 and the air which may have different temperature. In combination with an appropriate thermal profile design for the test sensor 3300, the methods described herein provide a very good approximation of the temperature of the reagent 3315 at the time of reaction with the analyte. Advantageously, aspects of the present invention allow a user to use the test sensor 3300 and the meter 3400 right after the user has entered a new environment with a different ambient temperature, while conventional systems require users to wait, e.g., 15 minutes, for the test sensor 3300 and the meter 3400 to reach equilibrium with a new ambient temperature before an accurate measurement can be obtained.

Although the approaches for rapid temperature measurement are described herein with regard to a system including a test sensor 3300 and a meter 3400, the approaches may be employed in other systems that must account for temperature differences. For example, instead of using a test sensor body in particular, an embodiment may use a more general small mass temperature probe. To determine the temperature of the ambient, for example, such a temperature probe may be exposed to the ambient and then read by a device according to the approaches described herein.

Moreover, although the temperature changes in the embodiments described herein were modeled according to Equation 10 above, other embodiments may employ other models to account for heat transfer with a test sensor, or temperature probe. The particular models employed depend on the sources of heat transfer that may change the temperature of the area of the test sensor, or temperature probe, being measured.

Figure 36:
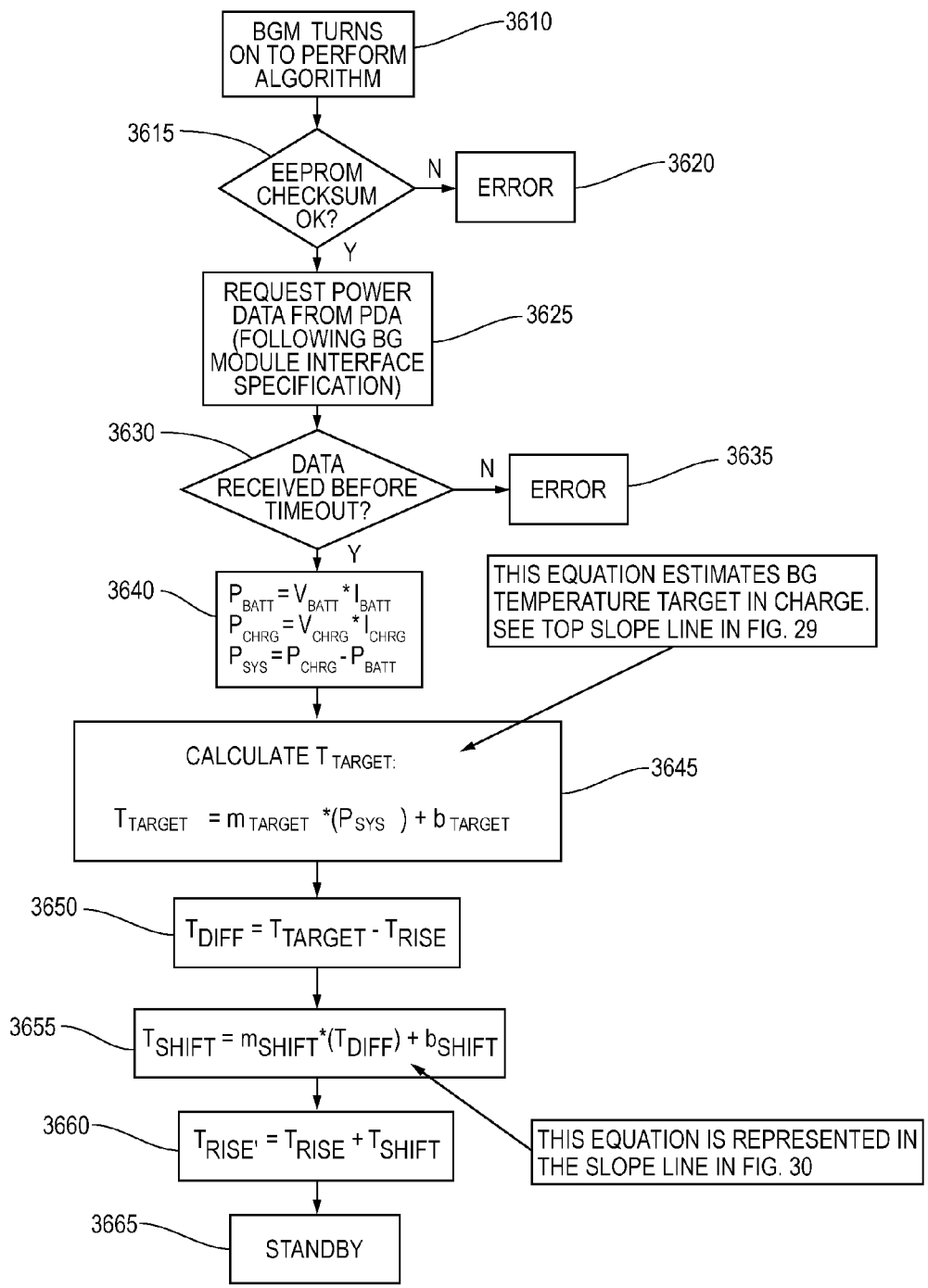
FIG. 36 illustrates logical flow diagram of a method for tracking temperature rise in a meter during a low-power consumption state according to another embodiment.

FIG. 36 illustrates another embodiment, similar to FIG. 31, for determining a temperature rise value for a blood glucose meter module (e.g., a fluid analyte meter) in a low power consumption mode (e.g., low state). At step 3610, the meter module turns on to perform the temperature rise determination. In one exemplary embodiment, the meter module may turn on or wake up every minute to perform the temperature rise determination. Other time intervals are also contemplated such that that the needs of the meter are met to accurately predict ambient temperature for the fluid analyte concentration determination. At step 3615, the meter module performs an EEPROM checksum determination. If there is an error, the algorithm proceeds to step 3620 and reports an error. If the EEPROM checksum is okay, the algorithm proceeds to step 3625 and the meter module requests power data from a portable device (e.g., a PDA or other advance portable electronic device). At step 3630, the meter checks if data was received before a timeout. If portable device does not respond, an error may be reported at step 3635 and the meter module may assume it is in a standby mode with no temperature rise. If the portable device does respond, the meter module determines power from the battery current and voltage data received from the PDA in step 3625.

At step 3640, the process begins to differ from the process illustrated in FIG. 31. Instead of having a separate accommodation for charge and discharge, the system power, $P_{SYS}$, is calculated as follows in Equation 17 and as shown in step 3640:

$$P_{SYS} = P_{CHRG} - P_{BATT} \quad \text{(Equation 17)}$$

where $P_{SYS}$=power associated with running the meter including, for example, the processor, the display, audio, fluid analyte measurements, etc.

$P_{CHRG}$=the product of the current and voltage measurements associated with the charging integrated circuit $P_{BATT}$=the product of the current measurements associated with the charging integrated and the voltage measurements associated with the battery; the value may be measured by a fuel gauge and is positive when charging and negative when discharging.

At step 3645, the target temperature rise is estimated based on the calculated value of system power. As generally illustrated, for example, in FIG. 29, the slope for the linear approximations for the system power can be made. The variables $m_{TARGET}$ and $b_{TARGET}$ represent the slope and x-axis intercept for the slope of the target temperature rise approximation.

At step 3150, the difference is determined between the target temperature rise calculated in step 3645 and the actual temperature rise in the meter module from an immediately prior measurement time period. Then at step 3655, a predicted temperature shift in the meter module is determined using the slope and y-axis intercept of a linear approximation determined according to the procedures discussed for FIG. 30. The predicted temperature shift is also based on the difference between the target temperature rise and the expected temperature rise in the meter module, determined in step 3650.

At step 3660, the temperature rise value is then reset for the present time interval to equal the previous value of temperature rise plus the predicted temperature shift determined in step 3655. It is contemplated that in certain embodiments, that temperature rise (e.g., $T_{RISE'}$) is updated at a predetermined time interval (e.g., approximately every minute or otherwise) by the calculated amount of temperature shift. The temperature rise value can be stored in a memory associated with the meter module. Next, at step 3665, the meter module can then go into a standby mode until prompted to again perform the steps outlined in FIG. 36 at the next predetermined time interval. The predetermined time interval can vary as necessary to meet the parameters for accurately predicting ambient temperature while balancing the need to reasonably conserve battery power.

It is contemplated that in certain embodiments, a host device (e.g., a PC, portable device, non-portable device) can enter into a low power or sleep mode that is not off. During this period, it is desirable for the meter module to not wake up and request power information, which otherwise would bring the host out of a low power or sleep state. During the low power or sleep state, certain embodiments described elsewhere herein can perform updates based on assumed system power values (e.g., zero, approximately zero) for the sleep state or low power state. The updates can be performed similar to steps 3140-3160 or 3640-3660 of FIGS. 31 and 36. It can be assumed that a zero power or low power value will generally lead to an internal cooling of the meter or meter module. An estimate of cooling can be made where the meter module wakes up, knows the host device is sleeping, and thus, does not communicate with a sleeping host device. An estimate of cooling can also be made where the meter module remains asleep during the time period the host device is asleep. Then upon the host device waking up, a determination is made of the number of time intervals that are missed (e.g., asleep for ten minutes yields ten calculations if the time interval is one minute) and running through iterations of steps 3640-3660 of FIG. 36 for each missed time intervals or by using equation 18 which consolidates steps 3640, 3645, 3650, 3655, and 3660 from FIG. 36 into a single calculation rather than as an iterative or recursive operation:

$$T_{RISE'} = T_{RISE} * (1-m_{SHIFT})^n + (P_{SYS} * m_{TARGET} * m_{SHIFT}) + (b_{TARGET} * m_{SHIFT}) + b_{SHIFT} \quad \text{(Equation 18)}$$

where n=the number of time intervals that were missed

Reference is made throughout this disclosure to specific values of time, temperature, and correction factors (see, e.g., FIGS. 7-9, 11-15, 21-23b, and 27-30). These values or factors are exemplary only and are intended to illustrate broader concepts for predicting ambient temperature in a fluid analyte meter. It would be understood by one of ordinary skill in the art that different values or factors could be determined using the examples disclosed herein for different types of fluid analyte meters. It would further be understood that the specific values and factors disclosed herein relate only to the described non-limiting exemplary embodiments.

Alternate Embodiment A

It is contemplated that according to certain embodiments, a meter module or a meter that may be a portable or non-portable device is configured to determine an analyte concentration of a fluid sample. The device can comprise a housing, a temperature sensor disposed within the housing, and a processor configured to receive temperature data obtained from the temperature sensor upon the meter entering at least one of a battery charge state or a battery discharge state. The processor is further configured to predict at least one temperature value that approximates the ambient temperature outside of the housing. The at least one predicted temperature value is based on stored historical temperature data associated with a temperature sensor such that the predicted temperature value remains constant if a recently received temperature value remains within predetermined upper and lower temperature thresholds and the recently received temperature value exceeds the at least one predicted temperature value.

According to certain embodiments, the above processor can further receive temperature data obtained from the temperature sensor at a predetermined periodic intervals.

According to certain embodiments, the above upper threshold is based on a previous predicted temperature value plus a predetermined value.

According to certain embodiments, the above lower threshold is based on a previous predicted temperature value minus a predetermined value.

According to certain embodiments, the above meter or meter module further comprises a sample port disposed within the housing. The device can enter the discharge state upon a sample strip being inserted into the sample port.

According to certain embodiments, the above the predicted temperature value is reset to a recently received temperature value if the recently received temperature value is outside a predetermined upper and lower temperature threshold values.

According to certain embodiments, the above analyte concentration of the fluid sample is determined based on the predicted temperature value.

According to certain embodiments, the above meter or meter module can further comprises a display disposed on the housing. The display is operable to display the analyte concentration of a fluid sample.

According to certain embodiments, the above meter or meter module further comprises a battery compartment disposed within the housing. The battery compartment is configured to store a rechargeable battery that provides power to the meter or module.

According to certain embodiments, an offset value is applied to the above at least one predicted temperature value prior to determining the analyte concentration of the fluid sample.

Alternate Embodiment B

It is contemplated that according to certain embodiments, a meter module or a meter that may be a portable or non-portable device is configured to determine an analyte concentration of a fluid sample. The meter or module includes a housing having a display thereon. The display is operable to display the analyte concentration of the fluid sample. A data transfer interface is configured to transmit data out of the meter or module. A first temperature sensor and a second temperature sensor are disposed within the housing. A processor is configured to receive temperature data obtained from the first temperature sensor and the second temperature sensor upon the meter or module commencing a transfer of data through the data transfer interface. The processor is further configured to predict at least one temperature value that approximates the ambient temperature outside of the housing. The at least one predicted temperature value is based on stored historical temperature data associated with the first temperature sensor and the second temperature sensor such that the at least one predicted temperature value is based on a determination of the temperature rise differences between the first temperature sensor and the second temperature sensor.

According to certain embodiments, the above predicted temperature is determined after the completion of the transmission of data through the data transfer interface.

According to certain embodiments, the above temperature value from the first temperature sensor that is associated with the predicted temperature is based on an average of a predetermined number of prior temperature values from the first temperature sensor.

According to certain embodiments, the above second temperature sensor is disposed near a sample port of the meter or module.

According to certain embodiments, the above data transfer interface is a USB connector.

According to certain embodiments, the above meter further comprises a battery compartment disposed within the housing. The battery compartment is configured to store a rechargeable battery that provides power to the meter or module.

According to certain embodiments, the above battery is recharged during the transfer of data through the data transfer interface.

Alternate Embodiment C

It is contemplated that according to certain embodiments, a meter module or a meter that may be a portable or non-portable device is configured to determine an analyte concentration of a fluid sample. The meter or module includes a housing having a display thereon. The display is operable to display the analyte concentration of the fluid sample. A temperature sensor is disposed within the housing. A processor is configured to receive temperature data obtained from the temperature sensor during a charge state of the meter or module. The processor is further configured to predict the ambient temperature external to the housing based on the received temperature data and an estimate of heating of the meter due to heat generated during the charge state of the meter or module. The estimate of heating is associated with a charge current.

According to certain embodiments, the above estimate of heating further includes determining an estimate heat dissipation of the meter or module.

According to certain embodiments, the above estimate of heat dissipation is based on an initial temperature value received at the commencement of charging or an end temperature value received at the end of charging.

According to certain embodiments, the above temperature sensor is disposed near a sample port located on the housing.

According to certain embodiments, the above meter further comprises a battery compartment disposed within the housing. The battery compartment is configured to store a rechargeable battery that provides power to the meter or module.

Alternate Embodiment D

It is contemplated that according to certain embodiments, a meter or meter module may be configured to determine an analyte concentration of a fluid sample. The meter or meter module includes a housing, a temperature sensor disposed within the housing, and a processor configured to receive temperature data obtained from the temperature sensor upon the meter or meter module entering at least one of a battery charge state or a battery discharge state. The processor is further configured to predict at least one temperature value that approximates the ambient temperature outside of the housing. The at least one predicted temperature value can be based on one or more or two or more of a first period of time associated with the meter or meter module being connected to an external charge source, a second period of time immediately after the meter or meter module is disconnected from the external charge source, a third period of time based on variable activity states associated with components within the meter or meter module; or any combination thereof.

According to certain embodiments, the above variable activity states include mass storage activity associated with the meter or meter module.

According to certain embodiments, the above variable activity states include an output interface associated with the meter or meter module.

According to certain embodiments, the above variable activity states include a display component associated with the meter or meter module.

According to certain embodiments, the above external charge source is directly connected to the meter or meter module.

According to certain embodiments, a cable connects the above external charge source to the meter or meter module.

Alternate Embodiment E

It is contemplated that according to certain embodiments, a meter or meter module may be configured to determine an analyte concentration of a fluid sample. The meter or meter module can include a printed circuit board having a temperature sensor disposed thereon, and a processor disposed within the printed circuit board. The processor can be configured to receive temperature data obtained from the temperature sensor during a battery charge state and a discharge state as determined by state data received by the processor. The processor can further be configured to predict a temperature value that approximates an ambient temperature surrounding the meter or meter module. The predicted temperature value can be determined at least partially from the received temperature data and a temperature correction value. The temperature correction value is based on a first period of time associated with the meter or meter module being in the charge state. The first period of time can have a predetermined upper time threshold such that if the first period of time exceeds the predetermined upper time threshold the temperature correction value is based on the predetermined upper time threshold and if the first period of time is less than the predetermined upper time threshold the temperature correction value is based on the first period of time.

According to certain embodiments, the above temperature correction value is further based on a second period of time associated with the meter being in a discharge state.

According to certain embodiments, the above temperature correction value is substantially proportional to at least one of the first period of time or the second period of time.

According to certain embodiments, the above temperature correction value is based on a time tracking variable associated with a data transfer state of the meter or meter module.

According to certain embodiments, the above time tracking variable increases in value if the data transfer state is in an active mode and the time tracking variable decreases in value if the data transfer state is in an inactive mode.

According to certain embodiments, the above temperature correction value is substantially proportional to a first time period immediately following the data transfer state entering the active mode. The temperature correction value can further be substantially proportional to a second time period immediately following the data transfer state entering the inactive mode.

Alternate Embodiment F

It is contemplated that according to certain embodiments, a meter or meter module may be configured to determine an analyte concentration of a fluid sample. The meter or meter module can include a printed circuit board having a temperature sensor disposed thereon, and a processor disposed within the printed circuit board. The processor can be configured to receive temperature data obtained from the temperature sensor during a battery charge state and a discharge state as determined by state data received by the processor. The processor can further be configured to predict a temperature value that approximates an ambient temperature surrounding the meter or meter module. The predicted temperature value can be determined at least partially from the received temperature data and a temperature correction value. The temperature correction value can be based on a predetermined rate of temperature decrease for the meter or meter module such that if the received temperature data decreases at a rate similar to the predetermined rate of temperature decrease then the processor remains in a standard operating mode and if the received temperature data decreases at a rate that exceeds the predetermined rate of temperature decrease then the processor implements a suspect-value routine.

According to certain embodiments, the above suspect-value routine is implemented upon the received temperature data decreasing below a predetermined temperature-decrease threshold.

According to certain embodiments, the above suspect-value routine is configured to record a suspect-value event in a memory associated with the meter module, the suspect-value event being associated with a time that the suspect-value event occurs.

Alternate Embodiment G

It is contemplated that according to certain embodiments, a meter or meter module may be configured to determine an analyte concentration of a fluid sample. The meter or meter module can include a printed circuit board having a temperature sensor disposed thereon, and a processor disposed within the printed circuit board. The processor is configured to receive temperature data obtained from the temperature sensor during a discharge state as determined by state data received by the processor. The processor is further configured to receive a discharge time associated with an instance at which the meter or meter module entered the discharge state. The processor can further be configured to predict a temperature value that approximates an ambient temperature surrounding the meter or meter module. The predicted temperature value is determined at least partially from the received temperature data. The received temperature data can include a first temperature value recorded at a first time and a second temperature value recorded at a second time. The predicted temperature value is based on the second temperature value if the difference between the first time and the second time exceeds a predetermined first threshold and is further based on a temperature correction value applied to the second temperature value if the difference between the second time and the discharge time is below a predetermined second threshold.

According to certain embodiments, the above predicted temperature value is the second temperature value with the applied temperature correction value if the second temperature value with the applied temperature correction value exceeds a third threshold value based on the first temperature value plus a predetermined temperature value.

According to certain embodiments, the above predicted temperature value is the first temperature value if the second temperature value with the applied temperature correction value is below a third threshold value, the third threshold value based on the first temperature value plus a predetermined temperature value.

According to certain embodiments, the above predicted temperature value is the second temperature value with the applied temperature correction value if the second temperature value with the applied temperature correction value is below the first temperature value.

Alternate Embodiment H

It is contemplated that according to certain embodiments, a meter or meter module may be configured to determine an analyte concentration of a fluid sample. The meter or meter module can include a printed circuit board having a temperature sensor disposed thereon, and a processor disposed within the printed circuit board. The processor can be configured to receive temperature data obtained from the temperature sensor during a discharge state as determined by state data received by the processor. The processor can be further configured to receive a discharge time associated with an instance at which the meter module entered the discharge state. The processor can be further configured to predict a temperature value that approximates an ambient temperature surrounding the meter or meter module. The predicted temperature value can be determined at least partially from the received temperature data. The received temperature data can include a first temperature value recorded at the discharge time and a second temperature value recorded at a second time after the first time. The processor can be further configured to determine the difference between the first time and the second time, and if the difference exceeds a predetermined threshold time, determine a rate of temperature decrease from temperature data recorded at predetermined time intervals subsequent to the second time. A first event subroutine is implemented by the processor if the rate of temperature decrease exceeds a predetermined rate threshold. The determination of the rate of temperature decrease is continued if the determined rate of temperature decrease is below the predetermined rate threshold such that the determination of the rate of temperature decrease continues until the occurrence of a predetermined event.

According to certain embodiments, the above predetermined event is the lapse of a predetermined period of time.

According to certain embodiments, the above predetermined event is the meter module entering into one of a sleep mode or a standby mode.

Alternate Embodiment I

It is contemplated that according to certain embodiments, a meter or meter module may be configured to determine an analyte concentration of a fluid sample. The meter or meter module can include a printed circuit board having a temperature sensor disposed thereon and a processor disposed within the printed circuit board. The processor can be configured to receive temperature data from the temperature sensor during a battery charge state and a discharge state as determined by state data received by the processor. The processor can be further configured to predict a temperature value that approximates an ambient temperature surrounding the meter module. The predicted temperature value is based on a temperature value received from the temperature sensor, one or more predetermined target temperature rise values associated with power consumption data received by the processor, and a first temperature rise value associated with one of the predetermined target temperature rise values.

According to certain embodiments, the above processor is further configured to determine a series of temperature rise values. The series of values includes at least the first temperature rise value and a prior second temperature rise value. The first temperature rise value is based on the prior second temperature rise value.

According to certain embodiments, the above predetermined target temperature rise value is based on a fraction of a net power consumption as determined by the processor and a predetermined constant.

According to certain embodiments, the above meter or meter module further includes an interface configured to transmit data from the meter or meter module.

According to certain embodiments, the above meter or meter module further includes an interface configured to receive power data from an interfaced device.

According to certain embodiments, the above predicted temperature value is the difference between the temperature value received from the temperature sensor and the first temperature rise value.

According to certain embodiments, the above predicted temperature value is associated with a fluid analyte concentration determination.

According to certain embodiments, the above the power data is received through the interface at predetermined time intervals.

According to certain embodiments, the above temperature sensor is disposed within the printed circuit board.

According to certain embodiments, the above meter or meter module further includes a second temperature sensor. The processor is configured to receive temperature data from the second temperature sensor. The processor is further configured to predict a second temperature value approximating ambient temperature outside of the housing. The second predicted temperature value is based on a temperature value received from the second temperature sensor, one or more predetermined target temperature rise values associated with the received power consumption data and associated with the second temperature sensor, and a second temperature rise value associated with one of the predetermined target temperature rise values.

Alternate Embodiment J

It is contemplated that according to certain embodiments, a meter or meter module may be configured to determine an analyte concentration of a fluid sample. The meter or meter module includes a printed circuit board having an interface for receiving information including temperature data associated with a temperature sensor and a processor disposed within the printed circuit board. The processor is configured to receive the temperature data during a battery charge state and a discharge state as determined by state data received by the processor. The processor is further configured to predict a temperature value that approximates an ambient temperature surrounding the meter module. The predicted temperature value is based on a temperature value associated with the received temperature data, one or more predetermined target temperature rise values associated with power consumption data received by the processor, and a first temperature rise value associated with one of the predetermined target temperature rise values.

Alternate Embodiment K

It is contemplated that according to certain embodiments, a portable or non-portable device may be configured to determine an analyte concentration of a fluid sample. The module includes a housing, a temperature sensor disposed on or within the housing, and a processor configured to receive temperature data from the temperature sensor during a battery charge state and a discharge state associated with the device. The processor is further configured to predict a temperature value that approximates the ambient temperature outside of the housing. The predicted temperature value is based on a temperature value received from the temperature sensor, one or more predetermined target temperature rise values associated with power consumption data received by the processor, and a first temperature rise value associated with one of the predetermined target temperature rise values.

According to certain embodiments, the above temperature sensor is disposed within the interior of the housing.

According to certain embodiments, the above temperature sensor is embedded in the housing.

According to certain embodiments, the above device further includes a user interface disposed on the housing. The user interface is operable to display the determined fluid analyte concentration.

Alternative Embodiment L

It is contemplated that according to some embodiments, a system for determining an analyte concentration in a fluid sample includes a test sensor including a fluid-receiving area for receiving a fluid sample. The fluid-receiving area contains a reagent that produces a measurable reaction with an analyte in the sample. The test sensor has a test-sensor reaction temperature corresponding to the reaction between the reagent and the analyte. The system also includes a meter including: an opening configured to receive the test sensor; a measurement system configured to determine a measurement of the reaction between the reagent and the analyte; and a temperature-measuring system configured to determine the test-sensor reaction temperature by taking a plurality of temperature measurements after the test sensor is received into the opening and fitting the plurality of temperature measurements to a model that accounts for heat transfer between the meter and the test sensor. In the system, the meter determines a concentration of the analyte in the sample using the measurement of the reaction and the measurement of the test-sensor reaction temperature.

Alternative Embodiment M

It is contemplated that according to some embodiments, a method for determining an analyte concentration in a sample of body fluid includes placing a test sensor into an opening of a meter. The test sensor includes a fluid-receiving area for receiving a sample of body fluid. The fluid-receiving area contains a reagent that produces a measurable reaction with an analyte in the sample. The test sensor has a test-sensor temperature and the reagent has a reagent temperature. The method also includes determining a measurement of the test-sensor temperature when the test sensor is received into the opening by taking a plurality of temperature measurements after the test-sensor is placed into the opening and fitting the plurality of temperature measurements to a model that accounts for heat transfer between the meter and the test sensor. The method further includes determining a concentration of the analyte in the sample according to the measurement of the reaction and the measurement of the test-sensor reaction temperature.

According to certain embodiments, the above method can be completed without, or by alternate methods in addition to, the model. For example, in certain situations, the actual temperature measured at or near the time of an analyte concentration reaction may be used. If necessary, correction factors can then be applied to the measured temperature.

It is contemplated that any of the systems, modules, or devices from the above-recited embodiments A-M may be combined and such combinations are contemplated to fall within the scope of the present disclosure. It is further contemplated that a fluid analyte meter, system, or module can include one, two, three, or more temperature sensors with all or some of the temperature sensors located at or near port(s) or sample port(s) of the apparatus. For example, a meter, system, or module can be configured to accept one or more samples or strips in one or more port(s). An apparatus can have one, two, three, or more ports. Each port can have one or more associated temperature sensors located at or near the port. It would be understood by one of ordinary skill in field of the present disclosure that the ambient temperature prediction methods and systems disclosed herein can be used with multi-port and/or multi-temperature sensor configurations (e.g., one, two, three, or more).

While the invention has been described with reference to details of the illustrated embodiments, these details are not intended to limit the scope of the invention as defined in the appended claims. For example, the rapid charge system for the blood glucose battery may be used in other heat-sensitive applications. The disclosed embodiments and obvious variations thereof are contemplated as falling within the spirit and scope of the claimed invention.

Appendix A

The cooling represented by part I of the graph shown in FIG. 34 may be modeled according to the following equation:

$$T(t)=(T_1-T_s)e^{-t/T_C}+T_s \quad (A1),$$

where $T_C$=time constant for part I, $T_m$=meter temperature; $T_s$=general test sensor temperature; and $T_1=T(t_1)$, temperature measured at time $t_1$.

The heating represented by part II of the graph may be modeled according to the following equation:

$$T(t)=(T_m-T_s)(1-e^{-t/T_H}) \quad (A2),$$

where $T_H$=time constant for part II.

The overall temperature curve in FIG. 34 may be modeled according to the following equation:

$$T(t)=T_m+(T_1-T_s)e^{-t/T_C}-(T_m-T_s)e^{-t/T_H} \quad (A3).$$

The following temperature measurements are obtained:

$$T(\infty)=T_m \quad (A4).$$

$$T(t_1)=T_1 \quad (A5).$$

$$T(t_m)=T_{sm} \quad (A6),$$

where $T_{sm}$=minimum temperature value measured at time $t_m$. Accordingly, $$\left.\frac{dT}{dt}\right|_{t_m}=0. \quad (A7)$$

$$\frac{T_1-T_s}{T_C}e^{-\frac{t_m}{T_C}}-\frac{T_m-T_s}{T_H}e^{-\frac{t_m}{T_H}}=0. \quad (A8)$$

$$\frac{T_1-T_s}{T_C}e^{-\frac{t_m}{T_C}}=\frac{T_m-T_s}{T_H}e^{-\frac{t_m}{T_H}}. \quad (A9)$$

$$e^{t_m\left(\frac{1}{T_H}-\frac{1}{T_C}\right)}=\frac{T_m-T_s}{T_1-T_s}\cdot\frac{T_C}{T_H}. \quad (A10)$$

$$t_m=\left[\ln\left(\frac{T_m-T_s}{T_1-T_s}\cdot\frac{T_C}{T_H}\right)\right]\cdot\frac{T_CT_H}{T_C-T_H} \quad (A11)$$
$$=\ln\left[\left(\frac{T_m-T_s}{T_1-T_s}\cdot\frac{T_C}{T_H}\right)^{\frac{T_CT_H}{T_C-T_H}}\right].$$

Applying $T(t_m)=T_{sm}$ to equation (A3):

$$T(t_m)=T_m+(T_1-T_s)e^{-t_m/T_C}-(T_m-T_s)e^{-t_m/T_H}=T_{sm}. \quad (A12)$$

$$T_m+(T_1-T_s)\cdot\left[\left(\frac{T_m-T_s}{T_1-T_s}\cdot\frac{T_C}{T_H}\right)^{\frac{T_H}{T_H-T_C}}\right]- \quad (A13)$$
$$(T_m-T_s)\cdot\left[\left(\frac{T_m-T_s}{T_1-T_s}\cdot\frac{T_C}{T_H}\right)^{\frac{T_C}{T_H-T_C}}\right]=T_{sm}.$$

Setting $x=T_m-T_s$; $y=T_1-T_s$; $z=T_m-T_{sm}$; and $r=T_C/T_H$:

$$z+y\cdot\left[\left(\frac{xr}{y}\right)^{\frac{1}{1-r}}\right]-x\cdot\left[\left(\frac{xr}{y}\right)^{\frac{r}{1-r}}\right]=0. \quad (A14)$$

$$\left(\frac{xr}{y}\right)^{\frac{1}{1-r}}-\frac{x}{y}\cdot\left(\frac{xr}{y}\right)^{\frac{r}{1-r}}+\frac{z}{y}=0. \quad (A15)$$

$$\left(\frac{x}{y}\right)^{\frac{1}{1-r}}\cdot r^{\frac{1}{1-r}}-\left(\frac{x}{y}\right)^{\frac{1}{1-r}}\cdot r^{\frac{r}{1-r}}=-\frac{z}{y}. \quad (A16)$$

$$\left(\frac{x}{y}\right)^{\frac{1}{1-r}}\cdot\left(r^{\frac{1}{1-r}}-r^{\frac{r}{1-r}}\right)=-\frac{z}{y}. \quad (A17)$$

$$\frac{\left(\frac{x}{y}\right)^{\frac{1}{1-r}}}{\frac{z}{y}}=-\frac{1}{r^{\frac{1}{1-r}}-r^{\frac{r}{1-r}}}=-\frac{1}{r^{\frac{r}{1-r}}(r-1)}=\frac{r^{\frac{r}{1-r}}}{1-r}. \quad (A18)$$

Setting $$R = \frac{r^{\frac{r}{1-r}}}{1-r}:$$

$$\left(\frac{x}{y}\right)^{\frac{1}{1-r}} \cdot \frac{y}{z} = R. \tag{A19}$$

$$\left(\frac{T_m - T_s}{T_1 - T_s}\right)^{\frac{1}{1-r}} \cdot (T_1 - T_s) = R \cdot (T_m - T_{sm}). \tag{A20}$$

$$\frac{1}{1-r}\ln\left(\frac{T_m - T_s}{T_1 - T_s}\right) + \ln(T_1 - T_s) = \ln[R \cdot (T_m - T_{sm})]. \tag{A21}$$

$$\ln\left(\frac{T_m - T_s}{T_1 - T_s}\right) + (1-r) \cdot \ln(T_1 - T_s) = (1-r) \cdot \ln[R \cdot (T_m - T_{sm})]. \tag{A22}$$

Setting $B = (1-r) \cdot \ln[R \cdot (T_m - T_s)]$:

$$\ln\left(\frac{T_m - T_s}{T_1 - T_s}\right) = B - (1-r) \cdot \ln(T_1 - T_s). \tag{A23}$$

$$\frac{T_m - T_s}{T_1 - T_s} = e^B \cdot (T_1 - T_s)^{r-1}. \tag{A22}$$

$$T_m - T_s = e^B \cdot (T_1 - T_s)^r. \tag{A23}$$

As $e^B = [R \cdot (T_m - T_{sm})]^{1-r} = R^{1-r} \cdot (T_m - T_{sm})^{1-r}$: (A24)
$$T_m - T_s = R^{1-r} \cdot (T_m - T_{sm})^{1-r} \cdot (T_1 - T_s)^r.$$

$$(T_m - T_{sm}) + (T_{sm} - T_s) = R^{1-r} \cdot (T_m - T_{sm})^{1-r} \cdot (T_1 - T_s)^r. \tag{A25}$$

$$(T_{sm} - T_s) = R^{1-r} \cdot (T_m - T_{sm})^{1-r} \cdot (T_1 - T_s)^r - (T_m - T_{sm}). \tag{A26}$$

$$T_{sm} - T_s = (T_m - T_{sm}) \cdot \left[R^{1-r} \cdot \left(\frac{T_1 - T_s}{T_m - T_{sm}}\right)^r - 1\right]. \tag{A27}$$

Using equation (A27), $T_{sm} - T_s$ may be plotted as a function of $T_m - T_{sm}$ (or $T_1 - T_s$ for varying $T_1$).
Setting $A = e^B$ in equation (A23):

$$T_m = T_s + A(T_1 - T_s)^r \tag{A28}.$$

Setting $g = (T_1 - T_s)$,
$$T_m = T_s + Ag^r \tag{A29}$$

Equation (A28) can be solved numerically to find $T_s$. From equation (A28):

$$0 = dT_s + dA(T_1 - T_s)^r - Ar(T_1 - T_s)^{r-1} dT_s. \tag{A29}$$

$$[Ar(T_1 - T_s)^{r-1} - 1]dT_s = dA(T_1 - T_s)^r. \tag{A30}$$

$$\frac{dA}{dT_s} = \frac{[Ar(T_1 - T_s)^{r-1} - 1]}{(T_1 - T_s)^r}, \tag{A31}$$

$$\frac{dA}{dT_s} = \frac{[Arg^{r-1} - 1]}{g^r}, \tag{A32}$$

Setting $\Delta T = T_{s|n+1} - T_{s|n}$ and $\Delta A = A_{n+1} - A_n$, where n and n+1 denote successive iterations:

$$\Delta T_s \approx \Delta A \bigg/ \frac{dA}{dT_s}. \tag{A33}$$

For a given $\Delta A$, the next $\Delta T_s$ is given by:

$$\Delta T_s \approx \Delta A \bigg/ \frac{dA}{dT_s}\bigg|_{(T_{s|n+1}, T_1, T_{sm}, T_m)}. \tag{A34}$$

Thus, $$T_{s|n+2} = T_{s\,n+1} - \Delta T_s \tag{A35}.$$

Appendix B

The overall temperature curve in FIG. 34 may be modeled according to the following equation:

$$T(t) = T_m + (T_1 - T_s)e^{-t/T_C} - (T_m - T_s)e^{-t/T_H} \tag{B1}.$$

The following temperature measurements are obtained:

$$T(\infty) = T_m \tag{B2}.$$

$$T(t_2) = T_2 \tag{B3}.$$

$$T(t_m) = T_{sm} \tag{B4},$$

where $T_{sm}$ = minimum temperature value measured at time $t_m$.
Thus, $$T_2 = T_m + (T_1 - T_s)e^{-t_2/T_C} - (T_m - T_s)e^{-t_2/T_H} \tag{B5}.$$

$$T_2 - T_m = (T_1 - T_s)e^{-t_2/T_C} - (T_m - T_s)e^{-t_2/T_H} \tag{B6}.$$

$$(T_1 - T_s)e^{-t_2/T_C} = T_2 - T_m + (T_m - T_s)e^{-t_2/T_H} \tag{B7}.$$

$$T_1 - T_s = [T_2 - T_m + (T_m - T_s)e^{-t_2/T_H}] \cdot e^{t_2/T_C} \tag{B8}.$$

$$T_1 = T_s + [T_2 - T_m + (T_m - T_s)e^{-t_2/T_H}] \cdot e^{t_2/T_C} \tag{B8}.$$

As derived in APPENDIX A:

$$T_m = T_s + A(T_1 - T_s)^r \tag{B9},$$

where $A = e^B$, $B = (1-r) \cdot \ln[R \cdot (T_m - T_{sm})]$, $r = T_C/T_H$, and $$R = \frac{r^{\frac{r}{r-1}}}{1-r}.$$

Combining equations (B8) and (B9):

$$T_m = T_s + A \cdot \{[T_2 - T_m + (T_m - T_s)e^{-t_2/T_H}] \cdot e^{t_2/T_C}\}^r \tag{B10}.$$

$$T_m = T_s + A \cdot e^{t_2 r/T_C} \cdot [T_2 - T_m + (T_m - T_s)e^{-t_2/T_H}]^r \tag{B11}.$$

Setting $A' = A \cdot e^{t_2 r/T_C}$ and $g' = T_2 - T_m + (T_m - T_s)e^{-t_2/T_H}$ $$T_m = T_s + A' g'^r \tag{B12}.$$

From equation (B12), $$0 = dT_s + g'^r dA' - \tag{B13}$$
$$A' \cdot r \cdot [T_2 - T_m + (T_m - T_s)e^{-t_2/T_H}]^{r-1} \cdot e^{-t_2/T_H} dT_s.$$

$$0 = dT_s + g'^r dA' - rg'^{r-1} e^{-t_2/T_H} A' dT_s. \tag{B14}$$

$$(1 - rg'^{r-1} e^{-t_2/T_H} A') dT_s = -g'^r dA'. \tag{B15}$$

$$dT_s = \frac{g'^r dA'}{(rg'^{r-1} e^{-t_2/T_H} A' - 1)}. \tag{B16}$$

$$\frac{dA'}{dT_s} = \frac{(rg'^{r-1} e^{-t_2/T_H} A' - 1)}{g'^r}. \tag{B17}$$

Equation (B17) can be used to solve equation (B12) numerically to find $T_s$.

Setting $g=(T_1-T_s)$ in equation (B9):

$$T_m = T_s + Ag^r \quad (B18),$$

As expected, when $t_2=t_1=0$, i.e., the time when the test sensor is first received by the meter, and $T_2=T_1$, $$A' = A \cdot e^{t_2 r/T_C} = A \cdot e^{0 \cdot r/T_C} = A. \quad (B19)$$

$$\begin{aligned}g' &= T_2 - T_m + (T_m - T_s)e^{-t_2/T_H} \\ &= T_2 - T_m + (T_m - T_s)e^{-0/T_H} \\ &= T_1 - T_s \\ &= g.\end{aligned} \quad (B20)$$

$$dT_s = \frac{g'^r dA'}{(rg'^{r-1}e^{-0/T_H}A' - 1)} = \frac{g^r dA}{rg^{r-1}A - 1}. \quad (B21)$$

Equation (B20) corresponds with the results shown in APPENDIX A, e.g, equation (A31). Thus, the temperature $T_2$ at time $t_2$ may represent the measured temperature at any time, including $t_1=0$.

What is claimed is:

1. A meter configured to predict a temperature value associated with an analyte concentration determination of a fluid sample, the meter comprising:
   a housing defining an interior and an exterior of the meter;
   a temperature sensor disposed within the interior defined by the housing;
   a processor disposed within the interior defined by the housing, the processor configured to determine a new predicted temperature value that approximates an ambient temperature for the exterior defined by the housing, the new predicted temperature value based on a first stored prior predicted temperature value and received prior temperature data that is at least partially associated with the temperature sensor such that the new predicted temperature value is set equal to the first stored prior predicted temperature value if recently received prior temperature data from the temperature sensor represents a measured temperature value that (i) is within predetermined upper and lower temperature thresholds, and (ii) exceeds the first stored prior predicted temperature value.

2. The meter of claim 1, wherein the processor receives temperature data obtained from the temperature sensor at predetermined periodic intervals.

3. The meter of claim 1, wherein the predetermined upper threshold is based on a second stored prior predicted temperature value plus a predetermined value.

4. The meter of claim 1, wherein the predetermined lower threshold is based on a second stored prior predicted temperature value minus a predetermined value.

5. The meter of claim 1, wherein the housing forms a sample port therein, and wherein the meter enters the discharge state upon a strip being inserted into the sample port.

6. The meter of claim 1, wherein the new predicted temperature value is set to equal the measured temperature value if the measured temperature value is outside the predetermined upper and lower temperature thresholds.

7. The meter of claim 1, wherein the analyte concentration of the fluid sample is determined based on the new predicted temperature value.

8. The meter of claim 1, further comprising a display disposed on the housing, the display operable to display the analyte concentration of a fluid sample.

9. The meter of claim 1, further comprising a battery compartment disposed within the interior defined by the housing, the battery compartment configured to store a rechargeable battery that provides power to the meter.

10. The meter of claim 1, wherein an offset value is applied to the new predicted temperature value prior to determining the analyte concentration of the fluid sample.

11. The meter of claim 6, wherein the new predicted temperature value is set to equal the measured temperature value if the measured temperature value is less than the first stored prior predicted temperature value.

12. A meter configured to predict a temperature value associated with an analyte concentration determination of a fluid sample, the meter comprising:
   a housing having a display thereon, the display operative to display the analyte concentration of the fluid sample;
   a temperature sensor disposed within the housing;
   a battery compartment disposed within the housing, the battery compartment configured to store a rechargeable battery operative to power the meter during a battery charge state and a battery discharge state;
   a processor configured to receive temperature data obtained during the battery charge state, the received temperature data at least partially associated with the temperature sensor, the processor further configured to predict an ambient temperature external to the housing based on the received temperature data and an estimate of heating of the meter due to heat generated during the battery charge state, the estimate of heating associated with a variable battery charge current.

13. The meter of claim 12, wherein the estimate of heating further includes determining an estimate heat dissipation of the meter.

14. The meter of claim 13, wherein the estimate of heat dissipation is based on an initial temperature value received at the commencement of charging.

15. The meter of claim 13, where the estimate of heat dissipation is based on an end temperature value received at the end of charging.

16. The meter of claim 12, wherein the temperature sensor is disposed near a sample port located on the housing.

17. A method for predicting a temperature value in a meter for determining an analyte concentration of a fluid sample, the method comprising:
   receiving temperature data obtained from one or more temperature sensors;
   storing the temperature data in one or more memories associated with a processor;
   upon the meter entering at least one of a charge state or a discharge state, predicting via the processor a new temperature value that approximates an ambient temperature outside of a housing associated with the meter, the predicted temperature value based on a first stored prior predicted temperature value and the received temperature data,
   wherein the predicted new temperature value is equal to one of the following:
   (i) the first stored prior predicted temperature value if recently received temperature data represents a measured temperature value that is within predetermined upper and lower temperature thresholds and if the measured temperature value exceeds the first stored prior predicted temperature value,
   (ii) the measured temperature value if the measured temperature value is outside the predetermined upper and lower temperature thresholds, and (iii) the measured temperature value if the measured temperature value is less than the first stored prior predicted temperature value.

18. The method of claim 17, wherein the processor receives temperature data obtained from the one or more temperature sensors at predetermined periodic intervals.

19. The method of claim 17, wherein the predetermined upper threshold is based on a second stored prior predicted temperature value plus a predetermined value.

20. The method of claim 17, wherein the predetermined lower threshold is based on a second stored prior predicted temperature value minus a predetermined value.

21. The method of claim 17, wherein an offset value is applied to the predicted new temperature value prior to determining the analyte concentration of the fluid sample.

22. The method of claim 17, wherein the housing forms a sample port therein, and wherein the meter enters the discharge state upon a strip being inserted into the sample port.

* * * * *

UNITED STATES PATENT AND TRADEMARK OFFICE
CERTIFICATE OF CORRECTION

PATENT NO. : 8,649,997 B2
APPLICATION NO. : 13/122098
DATED : April 15, 2014
INVENTOR(S) : John Farrell et al.

It is certified that error appears in the above-identified patent and that said Letters Patent is hereby corrected as shown below:

Title Page (75), under "Inventors", in Column 1, Line 10, delete "IL (US)" and insert -- IN (US) --, therefor.

IN THE SPECIFICATION

In Column 4, Line 4, delete "an the" and insert -- the --, therefor.

In Column 4, Line 21, delete "an the" and insert -- the --, therefor.

In Column 6, Line 36, delete "illustrates logical" and insert -- illustrates a logical --, therefor.

In Column 45, Line 52, in (Equation 12), delete "$T(t)=c+(T_1-c+f)e_{-at}-fe^{-bt}$" and insert -- $T(t) = c + (T_1 - c + f)e^{-at} - fe^{-bt}$ --, therefor.

In Column 60, Line 9, delete "$T_{s\,n+1}$" and insert -- $T_{s|n+1}$ --, therefor.

In Column 60, Line 49, delete "$g'=T_2-T_m+(T_m-T_s)e^{t_2/T_H}$" and insert -- $g' = T_2 - T_m + (T_m - T_s)e^{-t_2/T_H}$ --, therefor.

Signed and Sealed this
Twenty-sixth Day of May, 2015

Michelle K. Lee
*Director of the United States Patent and Trademark Office*